(12) United States Patent
Elmaleh et al.

(10) Patent No.: US 11,679,095 B2
(45) Date of Patent: Jun. 20, 2023

(54) MACROPHAGES/MICROGLIA IN NEURO-INFLAMMATION ASSOCIATED WITH NEURODEGENERATIVE DISEASES

(71) Applicant: The General Hospital Corporation, Boston, MA (US)

(72) Inventors: David R. Elmaleh, Newton, MA (US); Rudolph E. Tanzi, Milton, MA (US); Timothy M. Shoup, Franklin, MA (US); Ana Griciuc, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 15 days.

(21) Appl. No.: 17/323,514

(22) Filed: May 18, 2021

(65) Prior Publication Data

US 2022/0079914 A1 Mar. 17, 2022

Related U.S. Application Data

(63) Continuation of application No. 16/328,956, filed as application No. PCT/US2017/049702 on Aug. 31, 2017, now abandoned.

(60) Provisional application No. 62/382,192, filed on Aug. 31, 2016.

(51) Int. Cl.
| | |
|---|---|
| *A61K 31/352* | (2006.01) |
| *C07D 311/24* | (2006.01) |
| *C07D 311/22* | (2006.01) |
| *A61P 25/28* | (2006.01) |
| *A61K 9/00* | (2006.01) |
| *A61K 45/06* | (2006.01) |

(52) U.S. Cl.
CPC .......... *A61K 31/352* (2013.01); *A61K 9/0019* (2013.01); *A61K 9/0073* (2013.01); *A61P 25/28* (2018.01); *C07D 311/22* (2013.01); *C07D 311/24* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,419,578 A | 12/1968 | Fitzmaurice et al. |
| 3,634,582 A | 1/1972 | Hartley et al. |
| 3,686,412 A | 8/1972 | Fitzmaurice et al. |
| 3,957,965 A | 5/1976 | Hartley et al. |
| 4,405,598 A | 9/1983 | Brown |
| 4,405,735 A | 9/1983 | Wiezer et al. |
| 4,429,545 A | 2/1984 | Steinberg |
| 4,481,206 A | 11/1984 | Spiegel et al. |
| 4,996,296 A | 2/1991 | Pecht et al. |
| 5,376,386 A | 12/1994 | Ganderton et al. |
| 5,567,720 A | 10/1996 | Averback |
| 5,594,142 A | 1/1997 | Gaa et al. |
| 5,655,523 A | 8/1997 | Hodson et al. |
| 5,830,920 A | 11/1998 | Chucholowski et al. |
| 5,904,937 A | 5/1999 | Augello et al. |
| 6,168,776 B1 | 1/2001 | Klunk et al. |
| 6,197,963 B1 | 3/2001 | Hirschmann et al. |
| 6,309,623 B1 | 10/2001 | Weers et al. |
| 6,696,039 B2 | 2/2004 | Kung et al. |
| 6,911,466 B2 | 6/2005 | Koo et al. |
| 6,946,116 B2 | 9/2005 | Kung et al. |
| 6,972,127 B2 | 12/2005 | Schenk |
| 7,160,559 B1 | 1/2007 | McGee et al. |
| 7,186,401 B2 | 3/2007 | Keller et al. |
| 7,858,803 B2 | 12/2010 | Elmaleh et al. |
| 8,381,454 B1 | 2/2013 | Robinson |
| 8,613,920 B2 | 12/2013 | Lieberburg et al. |
| 8,617,517 B2 | 12/2013 | Elmaleh et al. |
| 8,765,742 B2 | 7/2014 | Hilfiker et al. |
| 9,283,230 B2 | 3/2016 | Clunas et al. |
| 9,855,276 B2 | 1/2018 | Elmaleh |
| 9,861,608 B2 | 1/2018 | Elmaleh et al. |
| 9,913,847 B2 | 3/2018 | Elmaleh |
| 9,918,992 B2 | 3/2018 | Elmaleh |
| 9,925,282 B2 | 3/2018 | Elmaleh et al. |
| 9,968,618 B1 | 5/2018 | Elmaleh |
| 10,058,530 B2 | 8/2018 | Elmaleh |
| 10,092,564 B2 | 10/2018 | Moussy et al. |
| 10,188,757 B2 | 1/2019 | Elmaleh |
| 10,238,628 B2 | 3/2019 | Gerhart et al. |
| 10,245,331 B2 | 4/2019 | Elmaleh |
| 10,251,961 B2 | 4/2019 | Elmaleh |
| 10,398,704 B2 | 9/2019 | Elmaleh |

(Continued)

FOREIGN PATENT DOCUMENTS

| | | |
|---|---|---|
| CA | 2408793 A1 | 12/2001 |
| CN | 101754746 A | 6/2010 |

(Continued)

OTHER PUBLICATIONS

"Stages of ASL" ALS Association Texas Chapter, Retrieved online <https://www.alstexas.org/understanding-als/stages/>: 4 pages (2019).
Abraham et al., "Mast cell-orchestrated immunity to pathogens," Nat Rev Immunol, 10: 440-452 (2010).
Aisen et al., "Effects of rofecoxib or naproxen vs placebo on Alzheimer disease progression: a randomized controlled trial," JAMA, 289(21):2819-2826 (2003).
Akiyama et al., "Inflammation and Alzheimer's Disease," Neurobiol Aging, 21(3): 383-421 (2000).

(Continued)

*Primary Examiner* — My-Chau T. Tran
(74) *Attorney, Agent, or Firm* — Foley Hoag LLP; Janine S. Ladislaw; Lawrence P. Tardibono

(57) ABSTRACT

Described herein are methods of treating neuron inflammation conditions, for example, Alzheimer's disease, Parkinson's disease, Huntington's disease, ischemic stroke, and prion disease, comprising administering a therapeutically effective amount of cromolyn or a cromolyn derivative compound.

17 Claims, 15 Drawing Sheets

(56) References Cited

U.S. PATENT DOCUMENTS

| | | | |
|---|---|---|---|
| 10,406,164 B2 | 9/2019 | Elmaleh | |
| 10,413,551 B2 | 9/2019 | Elmaleh | |
| 10,525,005 B2 | 1/2020 | Elmaleh | |
| 10,561,612 B2 | 2/2020 | Elmaleh et al. | |
| 10,576,171 B2 | 3/2020 | Elmaleh | |
| 11,013,686 B2 | 5/2021 | Elmaleh | |
| 11,110,097 B2 | 9/2021 | Elmaleh | |
| 11,291,648 B2 | 4/2022 | Elmaleh et al. | |
| 2002/0009491 A1 | 1/2002 | Rothbard et al. | |
| 2002/0016359 A1 | 2/2002 | Hellberg et al. | |
| 2002/0091100 A1 | 7/2002 | Lezdey et al. | |
| 2002/0107173 A1 | 8/2002 | Friedhoff et al. | |
| 2004/0176469 A1 | 9/2004 | Thomas | |
| 2004/0223918 A1 | 11/2004 | Pham et al. | |
| 2004/0259952 A1 | 12/2004 | Abbas et al. | |
| 2006/0051319 A1 | 3/2006 | Yoo | |
| 2006/0142241 A1 | 6/2006 | Yoo | |
| 2006/0159629 A1 | 7/2006 | Tarara et al. | |
| 2006/0240007 A1 | 10/2006 | Sanders | |
| 2006/0276455 A1 | 12/2006 | Lindsberg et al. | |
| 2007/0015813 A1 | 1/2007 | Carter et al. | |
| 2007/0053843 A1 | 3/2007 | Dawson et al. | |
| 2007/0071690 A1 | 3/2007 | Mueller-Walz et al. | |
| 2007/0086981 A1 | 4/2007 | Meijer et al. | |
| 2007/0093457 A1 | 4/2007 | Arber et al. | |
| 2007/0178166 A1 | 8/2007 | Bernstein et al. | |
| 2007/0193577 A1 | 8/2007 | Keller | |
| 2007/0249644 A1 | 10/2007 | Pearson et al. | |
| 2007/0293538 A1 | 12/2007 | Hobden | |
| 2008/0021085 A1 | 1/2008 | Koo et al. | |
| 2009/0110679 A1 | 4/2009 | Li et al. | |
| 2009/0155256 A1 | 6/2009 | Black et al. | |
| 2010/0113613 A1 | 5/2010 | McLaurin et al. | |
| 2010/0143251 A1 | 6/2010 | Tamagnan et al. | |
| 2010/0173960 A1 | 7/2010 | Cruz et al. | |
| 2010/0234295 A1 | 9/2010 | Chen | |
| 2010/0236550 A1 | 9/2010 | Zeng et al. | |
| 2010/0266531 A1 | 10/2010 | Hsieh et al. | |
| 2010/0298389 A1 | 11/2010 | Elmaleh et al. | |
| 2011/0060138 A1 | 3/2011 | Elmaleh et al. | |
| 2011/0129530 A1 | 6/2011 | Venkatesh et al. | |
| 2011/0262442 A1 | 10/2011 | Hamilton et al. | |
| 2012/0058049 A1 | 3/2012 | Elmaleh et al. | |
| 2012/0082727 A1 | 4/2012 | Cocconi et al. | |
| 2012/0118991 A1 | 5/2012 | Keller et al. | |
| 2012/0121656 A1 | 5/2012 | Watson et al. | |
| 2012/0134929 A1 | 5/2012 | McGrath et al. | |
| 2012/0165366 A1 | 6/2012 | Ibrahim et al. | |
| 2012/0308613 A1 | 12/2012 | Staniforth et al. | |
| 2013/0197105 A1 | 8/2013 | Pipkin et al. | |
| 2014/0140927 A1 | 5/2014 | Elmaleh et al. | |
| 2014/0228304 A1 | 8/2014 | Jones et al. | |
| 2015/0224077 A1 | 8/2015 | Gerhart et al. | |
| 2015/0224078 A1 | 8/2015 | Gerhart et al. | |
| 2015/0274680 A1 | 10/2015 | Ueda et al. | |
| 2015/0283113 A1 | 10/2015 | Elmaleh | |
| 2016/0106704 A1 | 4/2016 | Elmaleh et al. | |
| 2016/0158150 A1 | 6/2016 | Morton et al. | |
| 2016/0310503 A1 | 10/2016 | Elmaleh | |
| 2017/0290797 A1 | 10/2017 | Elmaleh | |
| 2018/0066039 A1 | 3/2018 | Hyde-Deruyscher et al. | |
| 2018/0153803 A1 | 6/2018 | Elmaleh | |
| 2018/0169277 A1 | 6/2018 | Elmaleh | |
| 2018/0177789 A1 | 6/2018 | Elmaleh | |
| 2018/0177791 A1 | 6/2018 | Elmaleh | |
| 2018/0193491 A1 | 7/2018 | Elmaleh | |
| 2018/0193492 A1 | 7/2018 | Elmaleh | |
| 2018/0344682 A1 | 12/2018 | Elmaleh | |
| 2019/0022006 A1 | 1/2019 | Elmaleh et al. | |
| 2019/0388568 A1 | 12/2019 | Elmaleh | |
| 2020/0022947 A1 | 1/2020 | Elmaleh et al. | |
| 2020/0078366 A1 | 3/2020 | Elmaleh | |
| 2020/0338040 A1 | 10/2020 | Elmaleh | |
| 2020/0383908 A1 | 12/2020 | Elmaleh | |
| 2021/0023010 A1 | 1/2021 | Elmaleh et al. | |
| 2021/0059977 A1 | 3/2021 | Elmaleh | |
| 2021/0085601 A1 | 3/2021 | Elmaleh | |
| 2022/0062222 A1 | 3/2022 | Elmaleh et al. | |
| 2022/0125753 A1 | 4/2022 | Elmaleh | |
| 2022/0193087 A1 | 6/2022 | Elmaleh | |
| 2022/0218652 A1 | 7/2022 | Elmaleh et al. | |

FOREIGN PATENT DOCUMENTS

| | | |
|---|---|---|
| CN | 101848733 A | 9/2010 |
| CN | 103347500 A | 10/2013 |
| CN | 108164409 A | 6/2018 |
| CN | 108403708 A | 8/2018 |
| EP | 1632242 A2 | 3/2006 |
| EP | 2322163 A1 | 5/2011 |
| EP | 2377860 A1 | 10/2011 |
| EP | 2391618 A2 | 12/2011 |
| EP | 2890788 A1 | 7/2015 |
| EP | 2911664 B1 | 5/2019 |
| GB | 1144906 A | 3/1969 |
| GB | 1257162 A | 12/1971 |
| JP | 2001-151673 A | 6/2001 |
| JP | 2005/232171 A | 9/2005 |
| JP | 2005532091 A | 10/2005 |
| JP | 2009-536918 A | 10/2009 |
| JP | 2012-515712 A | 7/2012 |
| WO | WO-90/09789 A1 | 9/1990 |
| WO | WO-1997026934 A2 | 7/1997 |
| WO | WO-98/34596 A2 | 8/1998 |
| WO | WO-1999016422 A1 | 4/1999 |
| WO | WO-1999064095 A2 | 12/1999 |
| WO | WO-02/28820 A1 | 4/2002 |
| WO | WO-03/045331 A2 | 6/2003 |
| WO | WO-2004/071532 A1 | 8/2004 |
| WO | WO-2005/063732 A1 | 7/2005 |
| WO | WO-2005/104712 A2 | 11/2005 |
| WO | WO-2006/056492 A1 | 6/2006 |
| WO | WO-2007/094718 A1 | 8/2007 |
| WO | WO-2007/102059 A1 | 9/2007 |
| WO | WO-2008/013799 A2 | 1/2008 |
| WO | WO-2008/061373 A1 | 5/2008 |
| WO | WO-2008/128981 A1 | 10/2008 |
| WO | WO-2008/131298 A2 | 10/2008 |
| WO | WO-2009/010770 A2 | 1/2009 |
| WO | WO-2009/133128 A1 | 11/2009 |
| WO | WO-2010/084767 A1 | 7/2010 |
| WO | WO-2010/088455 A2 | 8/2010 |
| WO | WO-2011/136754 A1 | 11/2011 |
| WO | WO-2013/148366 A1 | 10/2013 |
| WO | WO-2015/002703 A1 | 1/2015 |
| WO | WO-2015/061397 A1 | 4/2015 |
| WO | WO-2016/081466 A1 | 5/2016 |
| WO | WO-2016/196401 A1 | 12/2016 |
| WO | WO-2017/027387 A1 | 2/2017 |
| WO | WO-2017027402 A1 | 2/2017 |
| WO | WO-2017/072335 A1 | 5/2017 |
| WO | WO-2017/087962 A1 | 5/2017 |
| WO | WO-2017/091644 A1 | 6/2017 |
| WO | WO-2017/162884 A1 | 9/2017 |
| WO | WO-2018/045217 A1 | 3/2018 |
| WO | WO-2019/199776 A1 | 10/2019 |
| WO | WO-2020/010049 A1 | 1/2020 |
| WO | WO-2020/051322 A1 | 3/2020 |
| WO | WO-2020/123449 A1 | 6/2020 |
| WO | WO-2021/207060 A1 | 10/2021 |
| WO | WO-2021/248022 A1 | 12/2021 |
| WO | WO-2022/146914 A1 | 7/2022 |

OTHER PUBLICATIONS

Alafuzoff et al., "Lower counts of astroglia and activated microglia in patients with Alzheimer's disease with regular use of non-steroidal anti-inflammatory drugs," J Alzheimers Dis, 2(1):37-46 (2000).

Albert et al., "Effects of age on the clinical pharmacokinetics of ibuprofen," Am J Med, 77(1, Part 1):47-50 (1984).

Albert et al., "Pharmacokinetics of ibuprofen," Am J Med, 77(1A):40-46 (1984).

(56) References Cited

OTHER PUBLICATIONS

Aloisi F. "Immune function of microglia". *Glia* (2001) 36,165-179.

Aswania et al., "Relative bioavailability of sodium cromoglycate to the lung following inhalation, using urinary excretion," J Clin Pharmacol, 47:613-618 (1999).

Banati, R. B. et al., "Cytotoxicity of microglia". *Glia* (1993) 7, 111-118.

Bannwarth et al., "Stereoselective disposition of ibuprofen enantiomers in human cerebrospinal fluid.," Br J Clin Pharmacol, 40(3):266-269 (1995).

Barone, F.C. et al, "Tumor necrosis factor-α: a mediator of focal ischemic brain injury". *Stroke* (1997) 28, 1233-1244.

Basek et al., "Efficacy of an Isotonic Small Droplet Size Nebulized DSCG on Asthma Control in Children," Acta Paediatrica, 99(Suppl 462):115 (2010).

Beach et al., "Cromolyn sodium toxicity studies in primates," Toxicol Appl Pharmacol, 57(3):367-400 (1981).

Beigel JH, et al. "Remdesivir for the treatment of Covid-19—preliminary report," The New England Journal of Medicine: 1-12 (2020).

Berge et al., "Pharmaceutical salts," J Pharm Sci, 66(1):1-19 (1977).

Bodor et al., "Improved delivery through biological membranes VII. Dermal delivery of cromoglycic acid (cromolyn) via its prodrugs," International Journal of Pharmaceutics, 7(1):63-75 (1980).

Bona, E. et al, "Chemokine and inflammatory cell response to hypoxia-ischemia in immature rats". *Pediatr. Res.* (1999) 45, 500-509.

Bot et al., "Perivascular mast cells promote atherogenesis and induce plaque destabilization in apolipoprotein E-deficient mice," Circulation, 115(19):2516-2525 (2007).

Breitner et al., "Extended results of the Alzheimer's disease anti-inflammatory prevention trial," Alzheimers Dement, 7(4):402-411 (2011).

Breitner, "Alzheimer disease: The changing view," Annals Neurol, 49(3):418-419 (2001).

Broe et al., "Anti-inflammatory drugs protect against Alzheimer disease at low doses," Arch Neurol, 57:1586-1591 (2000).

Bulic et al., "Tau protein and tau aggregation inhibitors," Neuropharmacology, 59: 276-289 (2010).

Butovsky et al., "Identification of a unique TGF-β-dependent molecular and functional signature in microglia," Nat Neurosci, 17(3):131-143 (2014).

Byron et al., "Selection and Validation of Cascade Impactor Test Methods," Respiratory Drug Delivery IX, 1: 169-178 (2004).

Cacabelos, "Donepezil in Alzheimer's disease: From conventional trials to pharmacogenetics," Neuropsychiatric Disease and Treatment 3(3):303-333 (2007).

Cairns et al., "Synthesis and Structure-Activity Relationships of Disodium Cromoglycate and Some Related Compounds," Journal of Medicinal Chemistry, 15(6):583-589 (1972).

Certificate of Analysis for Lactohale LH 201, Alpha-Lactose Monohydrate EP and USP, Full Release (DFE Pharma); Jan. 18, 2016.

Chen et al., "Current experimental therapy for Alzheimer's Disease," *Curr Neuropharmacol*, 5(2): 127-134 (2007).

Cherry et al., "Neuroinflammation and M2 microglia: the good, the bad, and the inflamed," J Neuroinflammation, 11(98): 1-15 (2014).

Choi et al., "A three-dimensional human neural cell culture model of Alzheimer's disease," Nature, 515:274-278 (2014).

ClinicalTrials.gov. Phase 1 Study of ALZT-OP1 Combination Therapy in Normal Healthy Volunteers. Sponsor: AZTherapies, Inc. Identifier: NCT02482324. Retrieved Apr. 9, 2020 from: http://clinicaltrials.gov/ct/show/NCT02482324?order=1.

ClinicalTrials.gov. Safety and Efficacy of ALZT-OP1a as Adjuvant Treatment in Subjects With Post-Ischemic Stroke Cognitive Impairment (PSCI). Sponsor: AZTherapies, Inc. Identifier: NCT03202147. Retrieved Feb. 6, 2020, 2020 from: https://clinicaltrials.gov/ct2/show/NCT03202147?term=cromolyn&draw=3&rank=11.

ClinicalTrials.gov. Safety and Efficacy Study of ALZT-OP1 in Subjects With Evidence of Early Alzheimer's Disease (COGNITE). Sponsor: AZTherapies, Inc. Identifier: NCT02547818. Retrieved Apr. 9, 2020 from: https://clinicaltrials.gov/ct2/show/study/NCT02547818?term=AZTherapies&draw=2&rank=1.

ClinicalTrials.gov. Treatment of Acute Stroke With Cromolyn(Single Dose). Sponsor: Wolfson Medical Center. Identifier: NCT01175525. Retrieved Feb. 6, 2020 from: https://clinicaltrials.gov/ct2/show/NCT01175525.

Cole et al., "Mechanisms of action of non-steroidal anti-inflammatory drugs for the prevention of Alzheimer's disease," CNS Neurol Disord Drug Targets, 9(2):140-148 (2010).

Cowell, R.M. et al, "Hypoxic-ischemic injury induces macrophage inflammatory protein-1alpha expression in immature rat brain," *Stroke* (2002) 33,795-801.

Cox et al., "Disodium Cromoglycate (FPL 670) ('Intal'*): A Specific Inhibitor of Reaginic Antibody-Antigen Mechanisms," Nature, 216: 1328-1329 (1967).

Cruz M.P., "Edaravone (Radicava): A novel neuroprotective agent for the treatment of amyotrophic lateral sclerosis," P&T. (2018) 43(1):25-28.

Cummings, "Alzheimer's Disease," N Engl J Med, 351(1):56-67 (2004).

Das et al., "Importance of particle size and shape on the tensile strength distribution and de-agglomeration of cohesive powders," Powder Technology, 249: 297-303 (2013).

Davies, "Clinical pharmacokinetics of ibuprofen. The first 30 years," Clin Pharmacokinet, 34(2):101-154(1998).

Deiana et al., "Methylthioninium Chloride Versus Rivastigmine and Their Co-Administration Efficacy in Reversing Scopolamine-Induced Cognitive Deficits in a Pharmacological Mouse Model of Alzheimer's Disease," Alzheimer's and Dementia, 4 (4, Supplement): T499 (2009).

Dello Russo et al., "The human microglial HMC3 cell line: where do we stand? A systematic literature review," J Neuroinflammation, 15: 259 (24 pages) (2018).

Denes, A. et al, "Proliferating resident microglia after focal cerebral ischaemia in mice," *J. Cereb. Blood. Flow. Metab.* (2007) 27, 1941-1953.

Desmond, D.W. et al., "Frequency and clinical determinants of dementia after ischemic stroke." *Neurology* (2000), 54, 1124-1131.

Doody et al., "Donepezil treatment of patients with MCI: a 48-week randomized, placebo-controlled trial," Neurology, 72(18):1555-1581 (2009).

Du et al., "Role of Microglia in Neurological Disorders and Their Potentials as a Therapeutic Target," Mol Neurobiol, 54: 7567-7584 (2017).

Dubbelaar et al., "The Kaleidoscope of Microglial Phenotypes," Front Immunol, 9: 1753 (2018).

Dunbar et al., "Dispersion and Characterization of Pharmaceutical Dry Powder Aerosols," Kona, 16:7-45(1998).

Elmaleh, D.R. et al, "Evaluation of F-18 Radiolabeled Cromolyn as a Potential Aβ Polymerization Inhibitor and PET Tracer". Poster at *Human Amyloid Image (HAI) Conference*, Miami, Florida, Jan. 2014.

EPAR (European Public Assessment Report) Seebri Breezhaler: Retrieved online at <http://www.ema.europa.eu/ema/index.jsp?curl=pages/medicines/human/medicines/002430/human_med_001580.jsp&mid=WC0b01ac058001d124>: 6 pages (2012).

Etminan et al., "Effect of non-steroidal anti-inflammatory drugs on risk of Alzheimer's disease: systematic review and meta-analysis of observational studies," Brit Med J, 327:128-131 (2003).

European Search Report for EP Application No. 13848340 dated Feb. 11, 2016.

European Search Report for European Application No. 14819448.3 dated Feb. 2, 2017.

Extended European Search Report for EP Application No. 10736439.0 dated Jun. 12, 2012.

Extended European Search Report for EP Application No. 16867341.6 dated Jun. 13, 2019.

Extended European Search Report for EP Application No. 17934303 dated Aug. 13, 2021.

Extended European Search Report for EP Application No. EP 16869210 dated Sep. 19, 2019.

(56) References Cited

OTHER PUBLICATIONS

Extended European Search Report for EP Application No. EP 17847576 dated Jun. 30, 2020.
Extended European Search Report for EP Application No. EP 17918310 dated Mar. 12, 2021.
Extended European Search Report for EP Application No. EP 19166810 dated Sep. 23, 2019.
Extended European Search Report for EP Application No. EP 19172666 dated Jan. 10, 2020.
Extended European Search Report, EP 14855211.0, dated May 29, 2017.
Fiala, M. et al., "IL-17A is increased in the serum and in spinal cord CD8 and mast cells of ALS patients," *J Neuroinflammation*. (2010) 7:76.
Findeis et al., "Design and testing of inhibitors of fibril formation," Methods Enzymol, 309:476-488(1999).
Findeis et al., "Modified-peptide inhibitors of amyloid β-peptide polymerization," Biochemistry, 38(21):6791-6800 (1999).
Francesch et al., "Chronic inflammation (inflammaging) and its potential contribution to age-associated diseases," J Gerontol A Biol Sci Med Sci, 69(S1): S4-9 (2014).
Franzius, D., et al., "Non-specific effects of calcium entry antagonists in mast cells," *Pflugers Arch*. (1994) 428(5-6):433-438.
Gadani et al., "IL-4 in the brain: a cytokine to remember," J Immunol, 189(9): 4213-4219 (2012).
Galimberti et al., "Disease-modifying treatments for Alzheimer's disease," Ther Adv Neurol Disord, 4(4): 203-216 (2011).
Garmise, "Novel Dry Powder Preparations of Whole Inactivated Influenza Virus for Nasal Vaccination," Dissertation, University of North Carolina at Chapel Hill (2007).
Gasparini et al., "Non-steroidal anti-inflammatory drugs (NSAIDs) in Alzheimer's disease: old and new mechanisms of action," J Neurochem, 91(3):521-536 (2004).
Ghasemi. M. and Brown. R.H. Jr. "Genetics of amyotrophic lateral sclerosis," *Cold Spring Harb. Perspect. Med*. (2018) 8(5).
Gilani et al., "Influence of Formulation Variables and Inhalation Device on the Deposition Profiles of Cromolyn Sodium Dry Powder Aerosols," DARU 12(3):123-130 (2004).
Gilead Announces Approval of Veklury (remdesivir) in Japan for Patients With Severe COVID-19. The press release of Gilead Sciences. May 7, 2020. URL: <https://www.gilead.com/news-and-press/press-room/press-releases/2020/5/gilead-announces-approval-of-veklury-remdesivir-in-japan-for-patients-with-severe-covid19>. Retrieved on Jul. 14, 2021.
Gomperts et al., "Imaging amyloid deposition in Lewy body disease," Neurology, 71(12):903-910 (2008).
Gorelick, P.B. et al., "Vascular Contributions to Cognitive Impairment and Dementia, A Statement for Healthcare Professionals from the American Heart Association/American Stroke Association," *Stroke* (2011) 42, 2672-2713.
Gosselin et al., "An environment-dependent transcriptional network specifies human microglia identity," Science, 356: eaal3222 (2017).
Granucci et al., "Cromolyn sodium delays disease onset and is neuroprotective in the SOD1G93A Mouse Model of amyotrophic lateral sclerosis," Sci Rep, 9: 17728 (17 pages) (2019).
Granucci et al., "Inducible IL-2 production by dendritic cells revealed by global gene expression analysis," Nat Immunol, 2(9): 882-888 (2001).
Granucci. E.J. et al., "Cromolyn sodium delays disease onset and is neuroprotective in the SOD1G93A mouse model of amyotrophic lateral sclerosis." *Sci Rep*. (2019) 9(1):17728.
Greenhalgh et al., "Immune cell regulation of glia during CNS injury and disease," Nat Rev Neurosci, 21: 139-152 (2020).
Grenier et al., "Three-dimensional modeling of human neurodegeneration: brain organoids coming of age," Mol Psychiatry, 25: 254-274 (2020).
Griffin, "What causes Alzheimer's?" The Scientist, 25:36-40 (2011).
Guchardi et al., "Influence of fine lactose and magnesium stearate on low dose dry powder inhaler formulations," International Journal of Pharmaceutics 348:10-17 (2008).
Gudesblatt et al., "Hexosaminidase A activity and amyotrophic lateral sclerosis," Muscle and Nerve, II: 227-230 (1988).
Guo et al., "Comparison of Delivery Characteristics from a Combination Metered-Dose Inhaler Using the Andersen Cascade Impactor and the Next Generation Pharmaceutical Impactor," J Pharm Sci, 97(8): 3321-3334 (2008).
Guo, J. et al., "Evaluating the levels of CSF and serum factors in ALS," *Brain Behav*. (2017) 7:e00637.
Gwin et al., "Cromolyn sodium in the treatment of asthma associated with aspirin hypersensitivity and nasal polyps," Chest, 72(2):148-153 (1977).
Haass et al., "Soluble protein oligomers in neurodegeneration: lessons from the Alzheimer's amyloid [beta]-peptide," Nat Rev Mol Cell Biol, 8(2):101-112 (2007).
Hallenbeck, J.M. "The many faces of tumor necrosis factor in stroke". *Nat Med* (2002) 8, 1363-1368.
Hashimoto et al., "Apolipoprotein E, especially apolipoprotein E4, increases the oligomerization of amyloid β peptide," J Neurosci, 32(43):15181-15192 (2012).
He et al., "Progress of Inhaled Devices for Asthma," Journal of Applied Clinical Pediatrics, 22(4):309-311 (2007).
Hemonnot et al., "Microglia in Alzheimer Disease: Well-Known Targets and New Opportunities," Front Aging Neurosci, 11:233(20 pages) (2019).
Heneka et al., "Acute treatment with the PPARγ agonist pioglitazone and ibuprofen reduces glial inflammation and Aβl-42 levels in APPV717I transgenic mice," Brain, 128:1442-1453 (2005).
Hensley, "Neuroinflammation in Alzheimer's Disease: Mechanisms, Pathologic Consequences, and Potential for Therapeutic Manipulation," J Alzheimers Dis, 21(1):1-14 (2010).
Hirouchi, "Current status and perspectives on the development of therapeutic agents for Alzheimer's disease," Nihon Yakurigaku Zasshi, 123(6):421-427 (2004).
Holian et al., "Mechanistic aspects of cromolyn sodium action on the alveolar macrophage: inhibition of stimulation by soluble agonists," Agents Actions, 33: 318-325 (1991).
Hoozemans et al., "Soothing the inflamed brain: effect of non-steroidal anti-inflammatory drugs on Alzheimer's disease pathology," CNS Neurol Disord Drug Targets, 10(1):57-67 (2011).
Hopperton et al., "Markers of microglia in post-mortem brain samples from patients with Alzheimer's disease: a systematic review," Mol Psychiatry, 23: 177-198 (2018).
Hori et al., "A Food and Drug Administration-approved asthma therapeutic agent impacts amyloid β in the brain in a transgenic model of Alzheimer disease," J Biol Chem, 290(4):1966-1978 (2015).
Hori et al., "A Food and Drug Administration-approved asthma therapeutic agent impacts amyloid beta in the brain in a transgenic model of Alzheimer disease," J Biol Chem, 290(4):1966-1978 (2015).
Hu et al., "Increased peripheral blood inflammatory cytokine levels in amyotrophic lateral sclerosis: a meta-analysis study," Scientific Reports, 7: Article No. 9094 (2017).
Huang et al., "Acute stress induces cardiac mast cell activation and histamine release, effects that are increased in Apolipoprotein E knockout mice.," Cardiovasc Res, 55(1):150-160 (2002).
Huang et al., "Stress-induced interleukin-6 release in mice is mast cell-dependent and more pronounced in Apolipoprotein E knockout mice," Cardiovasc Res, 59(1):241-249 (2003).
Ihle-Hansen, H. et al, "Incidence and subtypes of MCI and dementia 1 year after first-ever stroke in patients without pre-existing cognitive impairment," *Dement. Geriatr. Cogn. Disord*. (2011) 32, 401-407.
Ilieva, H., et al., "Non-cell autonomous toxicity in neurodegenerative disorders: ALS and beyond," *J. Cell Biol*. (2009) 187(6):761-772.
Imbimbo et al., "Are NSAIDs useful to treat Alzheimer's disease or mild cognitive impairment?," Front Aging Neurosci, 2(19):1-14 (2010).
Imbimbo, "An update on the efficacy of non-steroidal anti-inflammatory drugs in Alzheimer's disease," Expert Opinion on Investigational Drugs, 2009; 18(8), pp. 1147-1168.

(56) References Cited

OTHER PUBLICATIONS

InnoPharmalabs, "Particle Size Distribution", Apr. 9, 2013 (Apr. 9, 2013).
Intal Approval Package, Center for Drug Evaluation and Research, application 75-175, pp. 1-5 (Dec. 12, 1997).
Intal® Nebulizer Solution (Label 2016): Retrieved online at <http://labeling.pfizer.com/ShowLabeling.aspx?id=833>: 4 pages (2016).
International Preliminary Report on Patentability for International Application No. PCT/US2019/040247 dated Jan. 14, 2021.
International Search Report and Written Opinion for International Application No. PCT/US16/63143 dated Feb. 6, 2017.
International Search Report and Written Opinion for International Application No. PCT/US16/63462 dated Feb. 1, 2017.
International Search Report and Written Opinion for International Application No. PCT/US17/65727 dated Feb. 12, 2018.
International Search Report and Written Opinion for International Application No. PCT/US19/49733 dated Jan. 13, 2020.
International Search Report and Written Opinion for International Application No. PCT/US2010/022495 dated Nov. 10, 2010.
International Search Report and Written Opinion for International Application No. PCT/US2014/061694 dated Jan. 2, 2015.
International Search Report and Written Opinion for International Application No. PCT/US2017/049702 dated Dec. 26, 2017.
International Search Report and Written Opinion for International Application No. PCT/US2019/026521 dated Jun. 14, 2019.
International Search Report and Written Opinion for International Application No. PCT/US2019/040247 dated Sep. 20, 2019.
International Search Report and Written Opinion for International Application No. PCT/US2021/025746 dated Jun. 17, 2021.
International Search Report and Written Opinion for International Application No. PCT/US2021/035936 dated Jul. 22, 2021.
International Search Report and Written Opinion for International Application No. PCT/US19/65384 dated Mar. 31, 2020.
International Search Report for International Application No. PCT/US2013/066069 dated Mar. 13, 2014.
International Search Report for International Application No. PCT/US14/39118 dated Sep. 18, 2014.
Jellinger, K.A., "Alzheimer disease and cerebrovascular pathology: an update". J. Neural. Transm. (2002) 109, 813-836.
Jin et al., "Mast cells are early responders after hypoxia-ischemia in immature rat brain," Stroke, 40(9):3107-3112 (2009).
Jin, R. et al, "Inflammatory mechanisms in ischemic stroke: role of inflammatory cells," J Leukoc Biol (2010) 87, 779-789.
Jin, Y. et al, "Mast cell stabilization limits hypoxic-ischemic brain damage in the immature rat". Dev Neurosci. (2007) 29, 373-384.
Jurga et al., "Overview of General and Discriminating Markers of Differential Microglia Phenotypes," Front Cell Neurosci, 14: 198 (18 pages) (2020).
Kamiya., "Characteristics and problems of cascade impactors in the evaluation of inhaled preparations," Journal of Pharmaceutical Science and Technology, Japan, 65(4): English Machine Translation (5 pages)(2005).
Karran et al., "The amyloid cascade hypothesis for Alzheimer's disease: an appraisal for the development of therapeutics," Nat Rev, 10(9):698-712 (2011).
Kaur et al., "Drug Therapy in Stroke: From Preclinical to Clinical Studies," Pharmacology, 92:234-334 (2013).
Kay et al., "Disodium cromoglycate inhibits activation of human inflammatory cells in vitro," J Allergy Clin Immunol, 80(1): 1-8 (1987).
Keizman D. et al. Low-grade systemic inflammation in patients with amyotrophic lateral sclerosis. Acta Neurol Scand. (2009) 119:383-389.
Keller et al., "Have inadequate delivery systems hampered the clinical success of inhaled disodium cromoglycate? Time for reconsideration," Exp Opin Drug Deliv, 8(1):1-17 (2011).
Kelley et al., "The molecular role of mast cells in atherosclerotic cardiovascular disease," Mol Med Today, 6:304-308 (2000).

Kilpatrick et al., "Cromolyn inhibits assembly of the NADPH oxidase and superoxide anion generation by human neutrophils," The Journal of Immunology, 154(7): 3429-3436 (1995).
Knowles, "Donepezil in Alzheimer's disease: an evidence-based review of its impact on clinical and economic outcomes," Core Evid, 1(3):195-219 (2006).
Kohman et al., "Neurogenesis, inflammation and behavior," Brain Behav Immun, 27C:22-32 (2013).
Kondo et al., "iPSC-Based Compound Screening and In Vitro Trials Identify a Synergistic Anti-amyloid β Combination for Alzheimer's Disease," Cell Rep, 21: 2304-2312 (2017).
Koo et al., "Amyloid diseases: Abnormal protein aggregation in neurodegeneration," PNAS, 96:9989-9990 (1999).
Kotilinek et al., "Cyclooxygenase-2 inhibition improves amyloid-β-mediated suppression of memory and synaptic plasticity," Brain, 131(3):651-664 (2008).
Koudstaal et al., "Secondary Stroke Prevention in Atrial Fibrillation: Indications, Risks, and Benefits," J Thromb Thrombolys, 7(1):61-65 (1999).
Krstic et al., "Deciphering the mechanism underlying late-onset Alzheimer disease," Nat Rev Neurol, 9:25-34(2013).
Krueger, M. et al., "Blood-brain barrier breakdown involves four distinct stages of vascular damage in various models of experimental focal cerebral ischemia," J. Cereb. Blood Flow Metab. (2015), 35, 292-303.
Kuhle, J. et al., Increased levels of inflammatory chemokines in amyotrophic lateral sclerosis, Eur J Neurol. (2009) 16:771-774.
Kumon et al., "Application and Mechanism of Inhalation Profile Improvement of DPI Formulations by Mechanofusion with Magnesium Stearate," Chemical and Pharmaceutical Bulletin, 56(5): 617-625 (2008).
Kwong et al., "Comparison of Nebulized Particle Size Distribution with Malvern Laser Diffraction Analyzer Versus Andersen Cascade Impactor and Low-Flow Marple Personal Cascade Impactor," J Aerosol Med, 13(4): 303-314 (2000).
Lalancette-Hébert, M. et al., "Selective ablation of proliferating microglial cells exacerbates ischemic injury in the brain," J Neurosci (2007) 27, 2596-2605.
Lanz et al., "The γ-Secretase Inhibitor N-[N-(3,5-Difluorophenacetyl)-L-alanyl]-S-phenylglycine t-butyl Ester Reduces Aβ Levels in Vivo in Plasma and Cerebrospinal Fluid in Young (Plaque-Free) and Aged (Plaque-Bearing) Tg2576 Mice," The Journal of Pharmacology and Experimental Therapeutics, 305(3):864-871 (2003).
Lasiene, J and Yamanaka, K., "Glial cells in amyotrophic lateral sclerosis," Neurol Res Int. (2011) 2011: Article ID 718987.
Lee, P.H. et al, "Circulating beta amyloid protein is elevated in patients with acute ischemic stroke". J. Neural. Transm. (Vienna). (2005) 112, 1371-9.
Lehman, L.L. and Rivkin, M.J., "Perinatal arterial ischemic stroke: Presentation, risk factors, evaluation, and outcome". Pediatr. Neurol. (2014) 51, 760-768.
Lewis et al., "Quantification of Alzheimer pathology in aging and dementia: age-related accumulation of amyloid-β (42) peptide in vascular dementia," Neuropathology and Applied Neurobiology, 32(2): 103-118 (2006).
Li et al., "TREM2 regulates innate immunity in Alzheimer's disease," J Neuroinflammation, 15: 107 (7 pages) (2018).
Libby, "Inflammation in atherosclerosis," Nature, 420(6917):868-874 (2002).
Lim et al., "Ibuprofen Suppresses Plaque Pathology and Inflammation in a Mouse Model of Alzheimer's Disease," The Journal of Neuroscience 20(15):5709-5714 (2000).
Liu et al., "Elevated Levels of IFN-γ in CSF and Serum of Patients with Amyotrophic Lateral Sclerosis," Plos One, 10(9): 11 pages (2015).
Liu, Y.H. et al, "Aβ is predictive for short-term neurological deficits after acute ischemic stroke". Neurotox Res. (2015) 27, 292-299.
Lobo-Silva et al., "Balancing the immune response in the brain: IL-10 and its regulation," J Neuroinflammation, 13: 297 (10 pages) (2016).
Loeb et al., "A randomized, controlled trial of doxycycline and rifampin for patients with Alzheimer's disease," J Am Geriatr Soc, 52(3): 381-7 (2004).

(56) References Cited

OTHER PUBLICATIONS

Mackenzie et al., "Nonsteroidal anti-inflammatory drug use and Alzheimer-type pathology in aging," Neurology, 50(4):986-990 (1998).
Madureira, S. et al, "Dementia and cognitive impairment three months after stroke". *Eur J Neurol* (2001) 8, 621-627.
Mandel, "CERE-110, an adeno-associated virus-based gene delivery vector expressing human nerve growth factor for the treatment of Alzheimer's disease," Curr Opin Mol Ther, 12(2): 240-247 (2010).
Marinkovic et al., "Evolution of Intracerebral Hemorrhage after Intravenous Tpa: Reversal of Harmful Effects with Mast Cell Stabilization," J Cerebr Blood F Met, 34(1):176-181 (2014).
Mash et al., "Loss of M2 muscarine receptors in the cerebral cortex in Alzheimer's disease and experimental cholinergic denervation," Science, 228(4703):1115-1117 (1985).
Material Safety Data Sheet Cromolyn Sodium: Retrieved online at<https://www.biobasic.com/amfilerating/file/download/file_id/24861/http://www.alli.wnyric.org/District/Documents/msds/files/cjx/cjxjy.html>: 5 pages (2017).
Mattson, M.P. et al, "Cellular signaling roles of TGFβ, TNF α and β APP in brain injury responses and Alzheimer's disease". *Brain Res. Brain Res. Rev.* (1997) 23, 47-61.
McArthur et al., "Annexin A1: a central player in the anti-inflammatory and neuroprotective role of microglia," J Immunol 185: 6317-6328 (2010).
McGeer et al. "Targeting microglia for the treatment of Alzheimer's disease," Expert Opin Ther Targets 19: 497-506 (2015).
McKittrick et al., "Mast Cells Promote Blood Brain Barrier Breakdown and Neutrophil Infiltration in a Mouse Model of Focal Cerebral Ischemia," J Cerebr Blood F Met, 35(4):638-647 (2015).
McLaurin et al., "Cyclohexanehexol inhibitors of Aβ aggregation prevent and reverse Alzheimer phenotype in a mouse model," Nat Med, 12(7):801-808 (2006).
Mitchell et al., "Aerodynamic Particle Size Analysis of Aerosols from Pressurized Metered-Dose Inhalers: Comparison of Andersen 8-Stage Cascade Impactor, Next Generation Pharmaceutical Impactor, and Model 3321 Aerodynamic Particle Sizer Aerosol Spectrometer," AAPS PharmSciTech, 4(4): Article 54 (2003).
Mohammed et al., "Effect of Sampling Volume on Dry Powder Inhaler (DPI)-Emitted Aerosol Aerodynamic Particle Size Distributions (APSDs) Measured by the Next-Generation Pharmaceutical Impactor (NGI) and the Andersen Eight-Stage Cascade Impactor (ACI)," APPS PharmSciTech, 13(3): 875-882 (2012).
Mor et al., "Mast cells and atherosclerosis," Israel Med Assoc J, 3:216-221 (2001).
Moreau C. et al. Elevated IL-6 and TNF-alpha levels in patients with ALS: inflammation or hypoxia. Neurology. (2005) 65:1958-1960.
Morihara et al., "Ibuprofen Suppresses Interleukin-1β Induction of Pro-Amyloidogenic α₁-Antichymotrypsin to Ameliorate β-Amyloid (Aβ) Pathology in Alzheimer's Models," Neuropsychopharmacology 30:1111-1120 (2005).
Moss et al., "The absorption and clearance of disodium cromoglycate from the lung in rat, rabbit, and monkey," Toxicol Appl Pharmacol, 17(3):699-707 (1970).
Murphy, "Cromolyn sodium: basic mechanisms and clinical usage," Pediatric Asthma, Allergy, and Immunology, 2(4):237-254 (1988).
Müller et al., "Fluorine in Pharmaceuticals: Looking Beyond Intuition," Science, 317: 1881 (2007).
Nagamoto-Combs et al., "Microglial phenotype is regulated by activity of the transcription factor, NFAT (nuclear factor of activated T cells)," J Neurosci, 30(28): 9641-9646 (2010).
Nagoshi, N. et al., "Riluzole as a neuroprotective drug for spinal cord injury: from bench to bedside," *Molecules*. (2015) 20(5):7775-7789.
Nakajima, K. and Kohsaka, S., "Microglia: activation and their significance in the central nervous system," *J Biochem* (2001) 130, 169-175.

Neale et al., "The pharmacokinetics of sodium cromoglycate in man after intravenous and inhalation administration," Br J Clin Pharmacol, 22:373-382 (1986).
Netzer et al., "The actual role of sodium cromoglycate in the treatment of asthma—a critical review," Sleep Breath, 16:1027-1032 (2012).
Newman et al., "Therapeutic Aerosols 1—Physical and Practical Considerations," Thorax, 38(12): 881-886 (1983).
Nihashi, T. et al., "Expression and distribution of beta amyloid precursor protein and beta amyloid peptide in reactive astrocytes after transient middle cerebral artery occlusion," *Acta Neurochir (Wien)*. (2001) 143, 287-295.
Noristani et al., "RNA-Seq Analysis of Microglia Reveals Time-Dependent Activation of Specific Genetic Programs following Spinal Cord Injury," Front Mol Neurosci, 10: 90 (16 pages) (2017).
Nys, G.M. et al., "Restrictions of the Mini-Mental State Examination in acute stroke." *Arch Clin Neuropsychol* (2005) 20, 623-629.
Obici et al., "AA amyloidosis: basic knowledge, unmet needs and future treatments," Swiss Medical Weekly, 142:w13580 (2012).
Omer et al., "Comparison between the next generation impactor and the twin glass impinge as model pulmonary drug delivery devices," Zanco J. Med. Sci., 23(1): 74-80 (2019).
Onderdijk et al., "IL-4 Downregulates IL-1β and IL-6 and Induces GATA3 in Psoriatic Epidermal Cells: Route of Action of a Th2 Cytokine," J Immunol, 195: 1744-1752 (2015).
Ono et al., "Push-pull benzothiazole derivatives as probes for detecting β-amyloid plaques in Alzheimer's brains," Bioorg Med Chem, 17(18):7002-7007 (2009).
Orr et al., "A Brief Overview of Tauopathy: Causes, Consequences, and Therapeutic Strategies," Trends in Pharmacological Sciences, 38(7): 637-648 (2017).
Package Insert Intal® (Label 2003): Retrieved online at http://www.accessdata.fda.gov/drugsatfda_docs/label/2004/18887slr020_intal_lbl.pdf.
Palacios et al., "The pharmacological assessment of RS 86 (2-ethyl-8-methyl-2,8-diazaspiro-[4,5]-decan-1,3-dion hydrobromide). A potent, specific muscarinic acetylcholine receptor agonist," Eur J Pharmacol, 125(1):45-62 (1986).
Panza et al., "Emerging drugs to reduce abnormal [beta]-amyloid protein in Alzheimer's disease patients," Expert Opin Emerging Drugs, 21(4): 377-391 (2016).
Panza et al., "Immunotherapy for Alzheimer's Disease: From anti-β-amyloid to tau-based Immunization strategies," Immunotherapy, 4(2):213-238 (2012).
Parajuli et al., "CCL11 enhances excitotoxic neuronal death by producing reactive oxygen species in microglia," Glia, 63: 2274-2284 (2015).
Parameswaran et al., "Tumor necrosis factor-α signaling in macrophages," Crit Rev Eukaryot Gene Expr, 20(2): 87-103 (2010).
Parepally et al., "Brain uptake of nonsteroidal anti-inflammatory drugs: ibuprofen, flurbiprofen, and indomethacin," Pharm Res, 23(5):873-881 (2006).
Park, J.H. et al, "Pathogenesis of cerebral microbleeds: In vivo imaging of amyloid and subcortical ischemic small vessel disease in 226 individuals with cognitive impairment". *Ann. Neurol.* (2013) 73, 584-593.
Parrella, E. et al., "The Role of Mast Cells in Stroke," *Cells* 8.5 (2019), 437 (22 pages).
Patkai, J. et al., "Deleterious effects of IL-9-activated mast cells and neuroprotection by antihistamine drugs in the developing mouse brain," *Pediatr. Res.* (2001) 50, 222-230.
Petersen et al., "Vitamin E and donepezil for the treatment of mild cognitive impairment," N Engl J Med, 352(23):2379-2388 (2005).
Philips T. and Robberecht W. "Neuroinflammation in amyotrophic lateral sclerosis: role of glial activation in motor neuron disease". *Lancet Neurol*. (2011) 10(3):253-263.
Pluta, R. et al., "Brain ischemia activates β- and γ-secretase cleavage of amyloid precursor protein: significance in sporadic Alzheimer's disease," *Mol Neurobiol*. (2013) 47, 425-434.
Pratico, "Alzheimer's disease and non-steroidal anti-inflammatory drugs: Old therapeutic tools with novel mechanisms of action?" Current Medicinal Chemistry—Central Nervous System Agents 5(2):111-117 (2005).

(56) References Cited

OTHER PUBLICATIONS

PubChem CID: 27503, "Cromolyn sodium", Created Jun. 24, 2005. Retreived from the Internet < URL: https://pubchem.ncbi.nlm.nih.gov/compound/Cromolyn-sodium>.

PubChem CID:204318, "Diethyl Cromoglycate," Created Aug. 9, 2005. Retrieved from the Internet <URL:https://pubchem.ncbi.nlm.nih.gov/compound/204318>.

Péhourcq et al., "Diffusion of arylpropionate non-steroidal anti-inflammatory drugs into the cerebrospinal fluid: a quantitative structure-activity relationship approach," Fundamental and Clinical Pharmacology, 18(1):65-70 (2004).

Radicava (edaravone) US Prescribing Information. Jersey City, New Jersey: MT Pharma America, Inc; May 2017.

Raivich, G. et al, "Neuroglial activation repertoire in the injured brain: graded response, molecular mechanisms and cues to physiological function". *Brain Res. Brain Res. Rev.* (1999) 30, 77-105.

Reagan-Shaw et al., "Dose Translation from Animal to Human Studies Revisited," The FASEB, 22: 659-661 (2007).

Renton. A.E.et al., "State of play in amyotrophic lateral sclerosis genetics," *Nat. Neurosci.* (2014) 17:17-23.

Reverchon et al., "Production of Cromolyn Sodium Microparticles for Aerosol Delivery by Supercritical Assisted Atomization," AAPS PharmSciTech 8(4), Article 114 (2007).

Richards et al., "Absorption and disposition kinetics of cromolyn sodium and the influence of inhalation technique," J Pharmacol Exp Ther, 241(3):1028-1032 (1987).

Richards et al., "Neurodegenerative diseases have genetic hallmarks of autoinflammatory disease," Hum Mol Genet, 27(R2): R108-R118 (2018).

Rilutek (riluzole) Tablets: US prescribing information. Cary, NC, USA: Covis Pharmaceuticals, Inc; 1995. (Revised Apr. 2016).

Roberts et al., "Next Generation Pharmaceutical Impactor (A New Impactor for Pharmaceutical Inhaler Testing). Part I: Design," Journal of Aerosol Medicine, 16(3): 283-299 (2003).

Romanin. C., et al., "Immunologically activated chloride channels involved in degranulation of rat mucosal mast cells," *EMBO J.* (1991) 10(12):3603-3608.

Rosen et al., "Mutations in Cu/Zn superoxide dismutase gene are associated with familial amyotrophic lateral sclerosis," *Nature*, 362: 59-62 (1993).

Rothwell, N. et al., "The role of interleukin 1 in acute neurodegeneration and stroke: pathophysiological and therapeutic implications," *J Clin Invest* (1997) 100, 2648-2652.

Rousselet et al., "Mouse Model of Intraluminal MCAO: Cerebral Infarct Evaluation by Cresyl Violet Staining," J Vis Exp, 69:e4038 (2012).

Sabbagh et al., "Latrepirdine, a potential novel treatment for Alzheimer's disease and Huntington's chorea," Curr Opin Investig Drugs, 11(1): 80-91 (2010).

Saleh I.A. et al. Evaluation of humoral immune response in adaptive immunity in ALS patients during disease progression. *J Neuroimmunol.* (2009) 215:96-101.

Sandoval, K.E., and Witt, K.A., "Blood-brain barrier tight junction permeability and ischemic stroke". *Neurobiology of Disease* (2008) 32, 200-219.

Sawada et al., "Induction of functional interleukin-2 receptor in mouse microglia," J Neurochem, 64: 1973-1979 (1995).

Schilling, M. et al, "Microglial activation precedes and predominates over macrophage infiltration in transient focal cerebral ischemia: a study in green fluorescent protein transgenic bone marrow chimeric mice". *Exp Neurol* (2003) 183, 25-33.

Schnabel, J. "Early Results of Alzheimer's Passive Vaccine Trial Mixed," http://www.dana.org/News/Details.aspx?id=42815 printed Jan. 19, 2017, pp. 1-3 (2008).

Schneider et al., "Current Alzheimer's disease clinical trials: methods and placebo outcomes," Alzheimers Dement, 5(5):388-397 (2009).

Selkoe, D.J., "Alzheimer's disease: genes, proteins, and therapy," *Physiol Rev.* (2001) 81, 741-766.

Shah et al., "The role of fluorine in medicinal chemistry," J Enzyme Inhib Med Chem, 22(5): 527-540 (2007).

Sheng et al., "Tumor necrosis factor alpha upregulates human microglial cell production of interleukin-10 in vitro," Clin Diagn Lab Immunol, 2(5): 604-608 (1995).

Shin et al., "Interpretation of Animal Dose and Human Equivalent Dose for Drug Development," Journal of Korean Oriental Medicine, 31(3):1-7 (2010).

Shoup et al., "Fluorinated Cromolyn Derivatives for Potential Alzheimer's Disease Treatment," J Nucl Med 60, 114 (2019).

Silverstein, F.S. et al, "Cytokines and perinatal brain injury". *Neurochem Int* (1997)30,375-383.

Sinniah et al., "The Anti-allergic Cromones: Past, Present, and Future," Front Pharmacol, 8:827 (10 pages) (2017).

Sousa et al., "Cellular and Molecular Characterization of Microglia: A Unique Immune Cell Population," Front Immunol, 8(198): 1-18 (2017).

STN database CAS RN: 16110-51-3 (Nov. 16, 1984).

Strbian et al., "Cerebral mast cells regulate early ischemic brain swelling and neutrophil accumulation," *J. Cereb. Blood Flow Metab.* 26:605-612 (2006).

Strbian et al., "Mast Cell Stabilization Reduces Hemorrhage Formation and Mortality After Administration of Thrombolytics in Experimental Ischemic Stroke," Circulation, 116(4):411-418 (2007).

Strbian, D. et al., "An emerging role of mast cells in cerebral ischemia and hemorrhage," *Ann Med* (2009) 41, 438-450.

Strbian, D. et al., "Mast cell blocking reduces brain edema and hematoma volume and improves outcome after experimental intracerebral hemorrhage," *J. Cereb. Blood Flow Metab.* (2007) 27, 795-802.

Strejan et al., "Suppression of chronic-relapsing experimental allergic encephalomyelitis in strain-13 guinea pigs by administration of liposome-associated myelin basic protein," J Neuroimmunol, 7(1):27-41 (1984).

Subramaniam et al., "Targeting Microglial Activation States as a Therapeutic Avenue in Parkinson's Disease," Front Aging Neurosci, 9(176): 1-18 (2017).

Sun et al., "Fluorinated molecules as drugs and imaging agents in the CNS," Curr Top Med Chem, 6(14): 1457-1464 (2006).

Sun et al., "Mast cells promote atherosclerosis by releasing proinflammatory cytokines," Nat Med, 13(6):719-724 (2007).

Sun et al., "Synthesis of *scyllo*-inositol derivatives and their effects on amyloid beta peptide aggregation," Bioorganic & Medicinal Chemistry 16:7177-7184 (2008).

Sun, J.H. et al., "Post-stroke cognitive impairment: epidemiology, mechanisms and management," *Ann Transl Med* (2014) 2(8): 80 (16 pages).

Szabo, K. et al, "Hippocampal lesion patterns in acute posterior cerebral artery stroke: clinical and MRI findings," *Stroke* (2009) 40, 2042-2045.

Tanaka, R. et al., "Migration of enhanced green fluorescent protein expressing bone marrow-derived microglia/macrophage into the mouse brain following permanent focal ischemia," *Neuroscience* (2003) 117, 531-539.

Taverni et al., "Donepezil medicated memory improvement in traumatic brain injury during post acute rehabilitation," Brain Inj, 12(1):77-80 (1998).

Thal et al., "A randomized, double-blind, study of rofecoxib in patients with mild cognitive impairment," Neuropsychopharmacology, 30:1204-1215 (2005).

Thériault et al., "The dynamics of monocytes and microglia in Alzheimer's disease," Alzheimer's Res Ther, 7:41 (10 pages) (2015).

Tiglutik (riluzole) oral suspension: US prescribing information. Berwyn, PA, USA: ITF Pharma, Inc; 1995 (Revised Sep. 2018).

Trias et al., "Phenotypic transition of microglia into astrocyte-like cells associated with disease onset in a model of inherited ALS," Front Cell Neurosci, 7: 274 (8 pages) (2013).

Trias, E., et al., "Significance of aberrant glial cell phenotypes in pathophysiology of amyotrophic lateral sclerosis," *Neurosci. Lett.* (2017) 636: 27-31.

(56) References Cited

OTHER PUBLICATIONS

Tronde et al., "Pulmonary absorption rate and bioavailability of drugs in vivo in rats: structure-absorption relationships and physicochemical profiling of inhaled drugs," J Pharm Sci, 92(6):1216-1233 (2003).
Upadhyaya, P. et al, "Therapy of Alzheimer's disease: An update," African Journal of Pharmacy and Pharmacology 4(6):408-421 (2010).
US FDA Guidance for Industry Suicidal Ideation and Behavior: Prospective Assessment of Occurrence in Clinical Trials (2012).
Veld et al., "Nonsteroidal antiinflammatory drugs and the risk of Alzheimer's disease," N Engl J Med, 345(21):1515-1521 (2001).
Vu et al., "Fluid-Based Biomarkers for Amyotrophic Lateral Sclerosis," Neurotherapeutics, 14: 119-134 (2017).
Wake et al., "Resting Microglia Directly Monitor the Functional State of Synapses In Vivo and Determine the Fate of Ischemic Terminals," J Neurosci, 29(13): 3974-3980 (2009).
Walker et al., "Immune phenotypes of microglia in human neurodegenerative disease: challenges to detecting microglial polarization in human brains," Alzheimer's Res Ther, 7:56 (9 pages) (2015).
Wang et al. "Allopregnanolone reverses neurogenic and cognitive deficits in mouse model of Alzheimer's disease," PNAS, 107(14): 6498-6503 (2010).
Weggen et al., "A subset of NSAIDs lower amyloidogenic Aβ42 independently of cyclooxygenase activity," Nature, 414(6860):212-216 (2001).
Wen, Y. et al., "Increased beta-secretase activity and expression in rats following transient cerebral ischemia," Brain Res. (2004) 1009, 1-8.
Wettstein et al., "Clinical trials with the cholinergic drug RS 86 in Alzheimer's disease (AD) and senile dementia of the Alzheimer type (SDAT)," Psychopharmacology, 84(4):572-573 (1984).
Wikipedia, "Cromoglicic acid", Aug. 22, 2017 (Aug. 22, 2017), retrieved on Sep. 3, 2019 from https://en.wikipedia.org/w/index.php?title=Cromoglicic_acid&oldid=796733877.
Wilcock et al., "Changing Perspective on the Role of Neuroinflammation in Alzheimer's Disease," Int J Alzheimers Dis, 2012: 495243 (7 pages) (2012).
Wilhelmsson et al., "Injury Leads to the Appearance of Cells with Characteristics of Both Microglia and Astrocytes in Mouse and Human Brain," Cereb Cortex, 27(6): 3360-3377 (2017).
Wisniewski et al., "Immunotherapeutic Approaches for Alzheimer's Disease," Neuron, 85(6): 1162-1176 (2015).
Yan et al., "Anti-inflammatory drug therapy alters β-amyloid processing and deposition in an animal model of Alzheimer's disease," J Neurosci, 23:7504-7509 (2003).
Yan, S.D. et al., "RAGE-Aβ interactions in the pathophysiology of Alzheimer's disease," Restor Neurol Neurosci. (1998) 12, 167-173.
Yang et al., "Increased levels of MIP-1α in CSF and serum of ALS," Acta Neurologica Scandinavica, 134(2): 94-100 (2016).
Yilmaz, G. et al., "Role of T lymphocytes and interferon-γ in ischemic stroke," Circulation (2006) 113, 2105-2112.
Yokota et al., "Roles of mast cells in the pathogenesis of inflammatory myopathy," Arthritis Research Therapy, 16(R72): 13 pages (2014).
Zekry, D. et al., "The vascular lesions in vascular and mixed dementia: the weight of functional neuroanatomy," Neurobiol Aging (2003) 24, 213-219.
Zhang et al., "Mast cell tryptase induces microglia activation via protease-activated receptor 2 signaling," Cellular Physiology and Biochemistry, 29: 931-940 (2012).
Zhang et al., "Cromolyn Reduces Levels of the Alzheimer's Disease-Associated Amyloid β-Protein by Promoting Microglial Phagocytosis," Sci Rep, 18; 8(1):1144 (2018).
Zhang et al., "Cromolyn Reduces Levels of the Alzheimer's Disease-Associated Amyloid β-Protein by Promoting Microglial Phagocytosis," Sci Rep, 8:1144 (9 pages) (2018).
Zhang, R. et al., "Evidence for systemic immune system alterations in sporadic amyotrophic lateral sclerosis (sALS)," J Neuroimmunol. (2005) 159(1-2): 215-224.
Zhang, S. et al., "Cerebral mast cells contribute to postoperative cognitive dysfunction by promoting blood brain barrier disruption," Behavioural Brain Research (2016) 298, 158-166.
Zhang, X. et al., "Activated brain mast cells contribute to postoperative cognitive dysfunction by evoking microglia activation and neuronal apoptosis," Journal of Neuroinflammation (2016) 13:127 (15 pages).
Zhang, X. et al., "Cerebral mast cells participate in postoperative cognitive dysfunction by promoting astrocyte activation," Cellular Physiology and Biochemistry (2016) 40, 104-116.
Zhao et al., "Microglia-targeting nanotherapeutics for neurodegenerative diseases," APL Bioeng, 4:030902 (17 pages) (2020).
Zhou et al., "Drug-lactose binding aspects in adhesive mixtures: controlling performance in dry powder inhaler formulations by altering lactose carrier surfaces," Adv Drug Deliv Rev, 64(3):275-284 (2012).
Zhu et al., "Pharmacy," Fourth Military Medical University Press, 309, (2007).
Zlokovic, "Neurovascular pathways to neurodegeneration in Alzheimer's disease and other disorders," Nat Rev Neurosci, 12(12):723-738 (2011).
Andreasen et al. "Sensitivity, specificity, and stability of CSF-tau in AD in a community-based patient sample," Neurology. (1999) 53: 1488-94 (19 pages).
Arnáiz et al., "Neuropsychological features of mild cognitive impairment and preclinical Alzheimer's disease," Acta Neurol Scand Suppl. (2003) 179: 34-41.
Baig et al., "Use of Peptides for the Management of Alzheimer's Disease: Diagnosis and Inhibition," Frontiers in Aging Neuroscience, 10: 1-6 (2018).
Blennow K., "Biomarkers in Alzheimer's disease drug development," Nat Med. (2010) 16: 1218-22.
Buchhave et al., "Cerebrospinal fluid levels of β-amyloid 1-42, but not of tau, are fully changed already 5 to 10 years before the onset of Alzheimer dementia," Arch Gen Psychiatry. (2012) 69: 98-106.
Bäckman et al., "Multiple Cognitive Deficits During the Transition to Alzheimer's Disease," Journal of Internal Medicine, (2004) 256(3): 195-204.
Carlesimo et al., "Memory Deficits in Alzheimer's Patients: A Comprehensive Review," Neuropsychol Rev. (1992) 3(2): 119-169.
Chow et al., "Investigation of Electrostatic Behavior of a Lactose Carrier for Dry Powder Inhalers," Pharmaceutical Research, 25(12): 2822-2834 (2008).
Dickson et al., "Diffuse Lewy body disease," Acta Neuropathol (Berl), 75: 8-15 (1987).
Extended European Search Report for EP Application No. 19786110.7 dated Mar. 7, 2022.
Extended European Search Report for EP Application No. 19830061.8 dated Mar. 11, 2022.
Grundman et al., "Mild cognitive impairment can be distinguished from Alzheimer disease and normal aging for clinical trials," Arch. Neurol. (2004) 61(1): 59-66.
International Search Report and Written Opinion for International Application No. PCT/US2021/065200 dated Mar. 24, 2022.
Lanari, et al., "Cerebrospinal fluid biomarkers and prediction of conversion in patients with mild cognitive impairment: 4-year follow-up in a routine clinical setting," Scientific World Journal. (2009) 9: 961-6.
Monge-Argilés et al. "Biomarkers of Alzheimer's disease in the cerebrospinal fluid of Spanish patients with mild cognitive impairment," Neurochem Res. (2011) 36: 986-993.
Mrak et al., Common Inflammatory Mechanisms in Lewy Body Disease and Alzheimer Disease, J Neuropathol Exp Neurol, 66(8): 683-686 (2007).
Newman et al., "Evolution of dry powder inhaler design, formulation, and performance," Respiratory Medicine, 96(5): 293-304 (2002).
Partial European Search Report for EP Application No. 19786110.7 dated Dec. 2, 2021.
Petersen et al., "Neuropathologic features of amnestic mild cognitive impairment," Arch. Neurol. (2006) 63 (5): 665-672.

(56) References Cited

OTHER PUBLICATIONS

Petersen R.C., "The Current Status of Mild Cognitive Impairment—What Do We Tell Our Patients?" Nat. Clin. Pract. Neurol., (2007) 3(2): 60-61.
Petersen, et al., "Mild cognitive impairment: clinical characterization and outcome," Arch. Neurol., (1999) 56 (3): 303-308.
Shalash et al., "The Relationship Between the Permeability and the Performance of Carrier-Based Dry Powder Inhalation Mixtures: New Insights and Practical Guidance," AAPS PharmSciTech, 19(2): 912-922 (2017).
Shoup et al., "Evaluation of fluorinated cromolyn derivatives as potential therapeutics for Alzheimer's Disease," Journal of Alzheimer's Disease, 80(2): 775-786 (2021).
Shur et al., "From single excipients to dual excipient platforms in dry powder inhaler products," International Journal of Pharmaceutics, 514: 374-383 (2016).
Steckel et al., "In-situ-micronization of disodium cromoglycate for pulmonary delivery," European Journal of Pharmaceutics and Biopharmaceutics, 55: 173-180 (2003).
Sunderland et al., "Decreased beta-amyloid1-42 and increased tau levels in cerebrospinal fluid of patients with Alzheimer disease," JAMA. (2003) 289: 2094-103.
Tabert, et al., "Neuropsychological prediction of conversion to Alzheimer disease in patients with mild cognitive impairment," Arch Gen Psychiatry. (2006) 63(8): 916-924.
Thal et al., "A Randomized, Double-Blind, Study of Rofecoxib in Patients with Mild Cognitive Impairment," Neuropsychopharmacology (2005) 30: 1204-1215.
Vidgren et al., "Effect of powder inhaler design on drug deposition in the respiratory tract," International Journal of Pharmaceutics, 42: 211-216 (1988).
Waldemar G., "Recommendations for the Diagnosis and Management of Alzheimer's Disease and Other Disorders Associated with Dementia: EFNS Guideline," Eur J Neurol. (2007) 14(1): e1-26.
Wang et al., "Pharmaceutical stabilization of mast cells attenuates experimental atherogenesis in low-density lipoprotein receptor-deficient mice," Atherosclerosis, 229: 304-309 (2013).
Young et al., "Lactose Composite Carriers for Respiratory Delivery," Pharmaceutical Research, 26(4): 802-810 (2008).
Zheng et al., "Cerebral Atherosclerosis is Associated with Cystic Infarcts and Microinfarcts, but not Alzheimer Pathologic Changes," Stroke, 44(10): 2835-2841 (2013).
Extended European Search Report for EP Application No. 19895399.4 dated Oct. 27, 2022.
Garringer et al., "Modeling familial British and Danish dementia", Brain Struct Funct 214(2-3): 235-244 (2010).
Thal et al., "Frontotemporal lobar degeneration FTLD-tau: Preclinical lesions, vascular and Alzheimer-related co-pathologies", J Neural Transm (Vienna), 122(7): 1007-1018 (2015).
Wikipedia, "Familial Amyloidosis, Finnish Type", Oct. 30, 2022, Retrieved online from "https://en.wikipedia.org/w/index.php?title=Familial_Amyloidosis,_Finnish_Type&oldid=1119142865".
Wikipedia, "Majority", Sep. 1, 2022, Retrieved online from "https://en.wikipedia.org/w/index.php?title=Majority&oldid=1107851583".
Extended European Search Report for EP Application No. 19857627.4 dated Aug. 8, 2022.
Han et al., "The therapeutic effects of sodium cromoglycate against influenza A virus H5N1 in mice," Influenza and Other Respiratory Viruses, 10(1): 57-66 (2015).
Partial European Search Report for EP Application No. 19857627.4 dated May 2, 2022.
Partial European Search Report for EP Application No. 19895399.4 dated Jul. 26, 2022.
Pasqualetti et al., "The Role of Neuroinflammation in Dementias" Current Neurology and Neuroscience, 15(4): 1-11 (2015).
Ramos et al., "Mast Cell Stabilization Improves Survival by Preventing Apoptosis in Sepsis," The Journal of Immunology, 185: 709-716 (2010).
Takano et al., "OSF4-J-2 Disodium cromoglicate inhibits gene expression of inflammation-related cytokines in lungs of septic mice," Journal of Pharmacological Sciences; Joint Symposium of the Japanese Society of Clinical Pharmacology and Therapeutics and The Japanese Pharmacological Society, 115(Supp.1): 102P (2011).
Wang et al., "Preventative effect of OMZ-SPT on lipopolysaccharide-induced acute lung injury and inflammation via nuclear factor-kappa B signaling in mice," Biochemical and Biophysical Research Communications, 485(2): 284-289 (2017).
Xiao et al., "Design, synthesis, and structure-activity relationships of 2-benzylidene-1-indanone derivatives as anti-inflammatory agents for treatment of acute lung injury," Drug Design, Development and Therapy, 12: 887-899 (2018).
Zazgornik et al., "Citric acid inhibits growth of Helicobacter pylori in vitro: a new strategy for eradication," Wein Klin Wochenschr, 123: 38-40 (2011).

MACROPHAGES/MICROGLIA IN NEURO-INFLAMMATION ASSOCIATED WITH NEURODEGENERATIVE DISEASES

RELATED APPLICATIONS

This application is a continuation of U.S. patent application Ser. No. 16/328,956, filed Feb. 27, 2019, which is the U.S. National Stage of International Patent Application No. PCT/US2017/049702, filed Aug. 31, 2017, which claims the benefit of priority to U.S. Provisional Patent Application Ser. No. 62/382,192, filed Aug. 31, 2016, the contents of each of which are hereby incorporated by reference in their entirety.

FIELD

The invention encompasses methods of treating a neuron inflammation condition comprising administered a therapeutically effective amount to a patient in need thereof of at least one compound having the following formula:

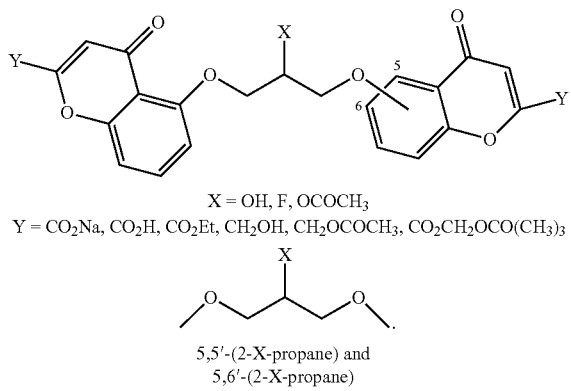

X = OH, F, OCOCH$_3$
Y = CO$_2$Na, CO$_2$H, CO$_2$Et, CH$_2$OH, CH$_2$OCOCH$_3$, CO$_2$CH$_2$OCO(CH$_3$)$_3$ 5,5′-(2-X-propane) and
5,6′-(2-X-propane)

BACKGROUND

Strategies to modulate monocyte and microglial activity have been studied, especially those that can protect against microglia-mediated neurotoxicity. (See, Zhao et al., "Protective effects of an anti-inflammatory cytokine, interleukin-4, on motoneuron toxicity induced by activated microglia," *J. Neurochem.* 2006, 99:1176-1187; Heneka et al., "NLRP3 is activated in Alzheimer's disease and contributes to pathology in APP/PS1 mice," *Nature,* 2013, 493(7434):674-8; Theeriault, et al., "The dynamics of monocytes and microglia in Alzheimer's disease," *Alzheimers Res Ther.,* 2015, 7:41; Nau et al., "Strategies to increase the activity of microglia as efficient protectors of the brain against infections," *Front Cell Neurosci.,* 2014, 8:138.) Overall, it is clear that more focused studies are needed to better establish how each inflammatory state can modulate the pathology of neurodegenerative diseases such as Alzheimer's Disease (AD) and Amyotrophic Lateral Sclerosis (ALS). Early activation of monocytes and microglia has potential to decelerate neurodegenerative progression by modulating immune responses to increase the intrinsic phagocytic capacity of monocytes and microglia without triggering secretion of pro-inflammatory cytokines that could worsen neurodegeneration.

The role of the neuro-inflammatory response in the presence of amyloid plaques and neurofibrillary tangles in the brain and its associated neuronal loss in the pathology of AD is well established and extensively studied. See, Walker et al., "Immune phenotypes of microglia in human neurodegenerative disease: challenges to detecting microglial polarization in human brains," *Alzheimers Res Ther.,* 2015, 7:56; Theerialut et al., 2015; Wilcock, D M, "A Changing Perspective on the Role of Neuroinflammation in Alzheimer's Disease," *International Journal of Alzheimer's Disease,* 2012, Article ID 495243; McGeer et al., "Targeting microglia for the treatment of Alzheimer's disease," *Expert Opin Ther Targets,* 2015, 19(4):497-506). Numerous studies show that microglial-mediated inflammation contributes to the progression of AD and that microglial cells are found in close association with amyloid-β (Aβ) deposits. (See, Mandrekar, et al., "Microglia and Inflammation in Alzheimer's Disease," *CNS Neurol Disord Drug Targets,* 2010, 9(2): 156-167).

It is known that the changes in properties of microglia—the brain-resident macrophages-depend on their response to different stimuli in their microenvironment (e.g. cytokines), resulting in a range of phenotypes. Based on the changes in expression of cytokines, receptors, and other markers, monocyte and macrophage states have been defined as: classical activation (M1), alternative activation (M2a), type II alternative activation (M2b), and acquired deactivation (M2c). (See, Walker et al., 2015; Martinez et al., "Alternative activation of macrophages: an immunologic functional perspective," *Annu Rev Immunol.* 2009, 27:451-83; Mantovani et al., "The chemokine system in diverse forms of macrophage activation and polarization," *Trends Immunol.,* 2004, 25:677-686; Sternberg, E M., "Neural regulation of innate immunity: a coordinated nonspecific host response to pathogens," *Nat Rev Immunol.,* 2006, 6(4):318-28). Recently, a number of studies have attempted to elucidate the role of these phenotypes in the AD brain and determine the mechanisms through which these cells contribute to AD-related neuro-inflammation. (See, Mandrekar et al. 2012; McGeer et al., 2015; and Wilcock, 2012).

Interaction of microglia with fibrillar Aβ leads to their phenotypic activation, and has recently been suggested to play a role in neuroprotection. (See Zhao et al., 2006; Figueiredo et al., "Neuron-microglia crosstalk up-regulates neuronal FGF-2 expression which mediates neuroprotection against excitotoxicity via JNK1/2," *J. Neurochem.,* 2008 October, 107(1):73-85). It has been shown in numerous studies, in both mice and humans, that glial cells respond to the presence of AD pathological lesions (plaques and tangles) by changing their morphological characteristics, expressing numerous cell surface receptors, and surrounding the lesions. (See, Perlmutter et al., "Morphologic association between microglia and senile plaque amyloid in Alzheimer's disease," *Neurosci Lett.,* 1990, 119:1, 32-36; Combs, et al., "Identification of microglial signal transduction pathways mediating a neurotoxic response to amyloidogenic fragments of β-amyloid and prion proteins," *J. Neurosci.,* 1999, 19:3, 928-939). On the other hand, macrophage and microglial activation in response to cellular debris in the AD brain, and the subsequent release of pro-inflammatory cytokines, leads to accelerated neurodegeneration. This, in turn, creates more cellular debris and accelerates disease progression. (See, Rubio-Perez et al., "A Review: Inflammatory Process in Alzheimer's Disease, Role of Cytokines," *Scientific World Journal,* 2012, 756357; McGeer, et al., "The importance of inflammatory mechanisms in Alzheimer disease," *Exp. Gerontol.* 1998, 33:5, 371-378; Akiyama, et al., "Inflammation and Alzheimer's disease," *Neurobiol Aging,* 2000, 21(3), 383-421; Liu, et al., "TLR2 is a primary receptor for Alzheimer's amyloid β peptide to trigger neuroinflammatory activation," *J. Immunol.* 2012, 188(3):1098-107).

Several studies have focused on microglial activation and its role in the clearance of AD lesions leading to the reduction of amyloid deposits in the brain. (See, DiCarlo, et al., "Intrahippocampal LPS injections reduce Aβ load in APP+PS1 transgenic mice," *Neurobiol of Aging*, 2001, 22:6, 1007-1012; Herber, et al., "Time-dependent reduction in Aβ levels after intracranial LPS administration in APP transgenic mice," *Exp. Neurol.*, 2004, 190(1):245-53; Liu, et al., 2012). While resident microglial cells surrounding Aβ plaques are not as efficacious in degrading Aβ as newly infiltrated macrophages or monocytes (See, Thériault, et al., 2015; Varnum, et al., "The classification of microglial activation phenotypes on neurodegeneration and regeneration in Alzheimer's disease brain," *Arch. Immunol. Ther. Exp.* (Warsz), 2012, 60(4):251-66), it has been shown that microglia are indeed capable of internalizing fibrillar and soluble Aβ, but are unable to process these peptides. (See Chung, et al., "Uptake, degradation, and release of fibrillar and soluble forms of Alzheimer's amyloid beta-peptide by microglial cells," *J. Biol. Chem.*, 1999, 274:32301-8).

Further, it has been postulated that microglia undergo a switch from an M2- to an M1-skewed activation phenotype during aging. (See, Heneka et al., 2013; Varnum, et al., 2012; Gratchev, et al., "Mphi1 and Mphi2 can be re-polarized by Th2 or Th1 cytokines, respectively, and respond to exogenous danger signals," *Immunobiology*, 2006, 211(6-8):473-486; Colton, et al., "Expression profiles for macrophage alternative activation genes in AD and in mouse models of AD," *J. Neuroinflammation*, 2006, 3:27). However, how the immune response in the brain is driven in AD is still a matter of debate, especially whether neuroinflammation can be triggered by age-related systemic inflammation. (See, Thériault, et al., 2015). It has been shown that stimulation of microglia could enhance their intrinsic phagocytic capacity to degrade Aβ more efficaciously; a number of strategies to modulate microglial response have been proposed. (See, Mandrekar, 2010; Kiyota, et al., "CNS expression of anti-inflammatory cytokine interleukin-4 attenuates Alzheimer's disease-like pathogenesis in APP+PS1 bigenic mice," *FASEB J.* 2010, 24:3093-3102; He, et al., "Deletion of tumor necrosis factor death receptor inhibits amyloid beta generation and prevents learning and memory deficits in Alzheimer's mice," *J. Cell Biol.*, 2007, 178:829-841; Varnum, et al., 2012).

It has been shown that microglia are activated by extracellularly deposited Aβ peptide (Lotz, et al., "Amyloid beta peptide 1-40 enhances the action of Toll-like receptor-2 and -4 agonists but antagonizes Toll-like receptor-9-induced inflammation in primary mouse microglial cell cultures," *J. Neurochem.*, 2005, 94:289-298; Reed-Geaghan, et al., "CD14 and toll-like receptors 2 and 4 are required for fibrillar Aβ-stimulated microglial activation," *J. Neurosci.*, 2009, 29:11982-11992). This is similar to microglial activation in response to the presence of interferon-γ (IFNγ), tumor necrosis factor alpha (TNFα) from T cells, or antigen-presenting cells. M1 activated microglia can produce reactive oxygen species and result in increased production of pro-inflammatory cytokines such as TNFα and interleukin (IL)-1β.

The M1-type response of microglial cells has been shown to lower amyloid load but exacerbate neurofibrillary tangle pathology. Shaftel et al. (Shaftel, et al., "Sustained hippocampal IL-1β overexpression mediates chronic neuroinflammation and ameliorates Alzheimer plaque pathology," *J. Clin. Invest.*, 2007, 117(6):1595-604) have shown that IL-1β expression may underlie a beneficial neuroinflammatory response in AD, and that IL-1β overexpression in the hippocampus of APP/PS1 transgenic mice results in decreased amyloid burden. The authors suggest that IL-1β-mediated activation of microglia is the mechanism for the reductions in amyloid deposition. Further, Montgomery et al. (Montgomery, et al., "Ablation of TNF-RI/RII expression in Alzheimer's disease mice leads to an unexpected enhancement of pathology: implications for chronic pan-TNF-α suppressive therapeutic strategies in the brain," *Am. J. Pathol.*, 2011, 179(4):2053-70) have shown that intact TNF-receptor signaling is critical for microglial-mediated uptake of extracellular amyloid-peptide. While M1 inflammatory phenotypes appear to improve the amyloid pathology in numerous studies, induction of M1 phenotypes in tau transgenic mice or cell culture results in the exacerbation of tau pathology. (See, Kitazawa, et al., "Lipopolysaccharide-induced inflammation exacerbates tau pathology by a cyclin-dependent kinase 5-mediated pathway in a transgenic model of Alzheimer's disease," *J. Neurosci.*, 2005, 28; 25(39): 8843-53.; Li, et al., "Interleukin-1 mediates pathological effects of microglia on tau phosphorylation and on synaptophysin synthesis in cortical neurons through a p38-MAPK pathway," *J. Neurosci.*, 2003, 1; 23(5):1605-11).

Macrophage M2 activation is associated with mediators that are known to contribute to the anti-inflammatory actions and reorganization of extracellular matrix (Zhu, et al., "Acidic mammalian chitinase in asthmatic Th2 inflammation and IL-13 pathway activation", *Science*, 2004, 304 (5677):1678-82; Walker, et al., 2015; Wilcock, et al., 2012). Microglia with M2a phenotypes have increased phagocytosis and produce growth factors such as insulin-like growth factor-1 and anti-inflammatory cytokines such as IL-10. Stimulation of macrophages by IL-4 and/or IL-13 results in an M2a state, sometimes called a wound-healing macrophage (Edwards, et al., "Biochemical and functional characterization of three activated macrophage populations," *J. Leukoc Biol.*, 2006, 80(6):1298-307) and it is generally characterized by low production of pro-inflammatory cytokines (IL-1, TNF and IL-6). The M2a responses are primarily observed in allergic responses, extracellular matrix deposition, and remodeling.

M2b macrophages are unique in that they express high levels of pro-inflammatory cytokines, characteristic of M1 activation, but also express high levels of the anti-inflammatory cytokine IL-10. (See, Moser D M., "The many faces of macrophage activation," *J. Leukoc Biol.*, 2003, 73(2): 209-12).

Finally, the M2c macrophage state is stimulated by IL-10 and is sometimes referred to as a regulatory macrophage. M2c macrophages have anti-inflammatory activity that plays a role in the phagocytosis of cellular debris without the classical pro-inflammatory response (See, Moser D M., 2003). These cells express TGFβ and high IL-10 as well as matrix proteins. (See, Mantovani, et al., "The chemokine system in diverse forms of macrophage activation and polarization," *Trends Immunol.*, 2004, 25:677-686; Wilcock, et al., 2012). Plunkett et al. (Plunkett, et al., "Effects of interleukin-10 (IL-10) on pain behavior and gene expression following excitotoxic spinal cord injury in the rat," *Exp. Neurol.*, 2001; 168:144-154) reported that IL-10 mediated anti-inflammatory responses including decreasing glial activation and production of pro-inflammatory cytokines.

However, the mechanism of M2 microglial activation and role it plays in AD and plaque pathology is still not well understood. (See, Mandrekar, et al., 2010). Further, a number of studies suggested that there is a switch in microglial activation status in response to disease progression (Colton, et al., 2006; Jimenez, et al., "Inflammatory response in the hippocampus of PS1M146L/APP751SL mouse model of Alzheimer's disease: age-dependent switch in the microglial phenotype from alternative to classic," *J. Neurosci.*, 2008, 28:11650-11661). It has been reported in animal studies that microglial activation phenotypes switch from M2 to M1 during disease progression (Jimenez, et al., 2008; Nolan, et al., "Role of interleukin-4 in regulation of age-related inflammatory changes in the hippocampus," *J. Biol. Chem.*, 2005; 280:9354-9362; Maher, et al., "Downregulation of IL-4-induced signalling in hippocampus contributes to deficits in LTP in the aged rat," *Neurobiol. Aging*, 2005, 26:717-728), suggesting an increased classical activation phenotype over the alternative phenotype with age. It is generally agreed that microglia activated by extracellularly deposited Aβ protect neurons by triggering anti-inflammatory/neurotrophic M2 activation and by clearing Aβ via phagocytosis. This is a potential avenue for new therapeutic targets. (See, He, et al., 2007; Yamamoto, et al., "Interferon-gamma and tumor necrosis factor-alpha regulate amyloid-beta plaque deposition and beta-secretase expression in Swedish mutant APP transgenic mice," *Am. J. Pathol.*, 2007, 170:680-692; Yamamoto, et al., "Cytokine-mediated inhibition of fibrillar amyloid-beta peptide degradation by human mononuclear phagocytes," *J. Immunol.*, 2008, 181:3877-3886).

Mantovani et al. (Mantovani, et al., 2004) studied the effect of IL-4 as an important modulator of M2a microglial activation. It has been shown that gene delivery of IL-4 into APP+PS1 mice partially suppressed glial accumulation in the hippocampus, directly enhanced neurogenesis, restored impaired spatial learning, and also reduced Aβ deposition (Kiyota, et al., 2010).

Yamamoto et al. (Yamamoto, et al., 2007, 2008) examined macrophage-mediated Aβ degradation using pro- and anti-inflammatory cytokines in primary cultured human monocyte-derived macrophages (MDM) and microglia. These studies showed that anti-inflammatory and regulatory cytokines lead to an increase in M2a or M2c activation and enhanced Aβ clearance. Kiyota et al. (Kiyota et al., 2011) have shown sustained expression of IL-4 reduced astro/microgliosis, amyloid-β peptide (Aβ) oligomerization and deposition, and enhanced neurogenesis.

Several approaches have been proposed to modulate microglial activation as potential targets for AD treatment. (See, Thériault, et al., 2015; Cherry, et al., "Neuroinflammation and M2 microglia: the good, the bad, and the inflamed," *J. Neuroinflammation*, 2014, 11:98; Mandrekar, et al., 2010; Vernum, et al., 2012). It has been suggested that use of anti-inflammatory drugs, like non-steroidal anti-inflammatory drugs (NSAIDs), to halt the progression of AD could be suppressing both pro-inflammatory and anti-inflammatory activation by endogenous molecules, inactivating the beneficial effect of M2 microglial functions and endogenous mechanisms of plaque clearance. (See, Wilcock, et al., 2012, Cherry, et al., 2014; Theeriault, et al., 2015).

Research has focused primarily on two areas: anti-inflammatory agents to temper toxic effect of pro-inflammatory cytokines; and converting microglia from this M1 state to an M2 state in which the toxic effects are reduced and their phagocytic activity toward Aβ is enhanced. It was suggested (McGreer, et al., 2012) that potential treatments should be administered early in the disease progression.

Strategies that modulate monocyte and microglial activity have been studied, especially those that can protect against microglia-mediated neurotoxicity (Zhao, et al., 2006; Heneka, et al., 2013; Therlaut, et al., 2015; Nau, et al., 2014). Overall, it is clear that more focused studies need to be performed to better establish how each inflammatory state can modulate the pathologies of AD. It is generally accepted that early activation of monocytes and microglia has potential to decelerate AD progression by modulating immune responses to increase the intrinsic phagocytic capacity of monocytes and microglia without triggering secretion of pro inflammatory cytokines that could worsen AD.

SUMMARY

In certain embodiments, the invention encompasses methods of treating a neuron inflammation condition comprising administering a therapeutically effective amount to a patient in need thereof of at least one compound having the following formula:

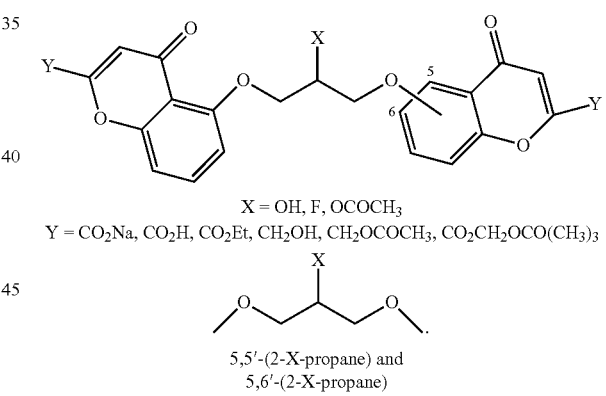

X = OH, F, OCOCH$_3$
Y = CO$_2$Na, CO$_2$H, CO$_2$Et, CH$_2$OH, CH$_2$OCOCH$_3$, CO$_2$CH$_2$OCO(CH$_3$)$_3$ 5,5'-(2-X-propane) and
5,6'-(2-X-propane)

In other embodiments, the method uses the following compounds:

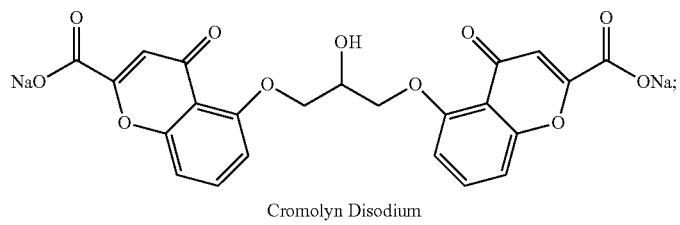

Cromolyn Disodium

-continued
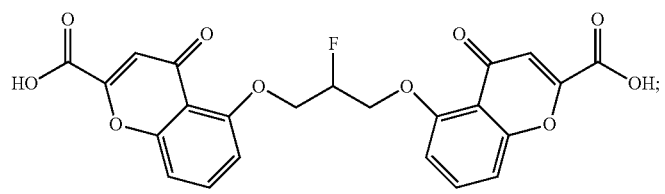
F-Cromolyn Diacid
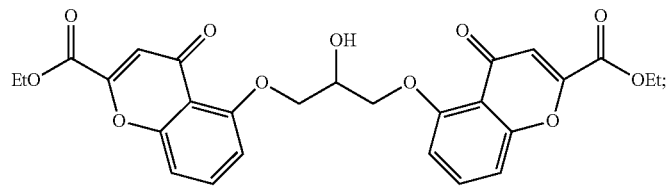
ET-Cromolyn
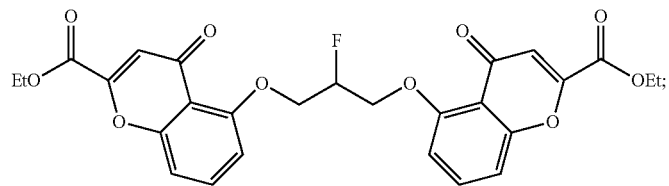
F-ET-Cromolyn
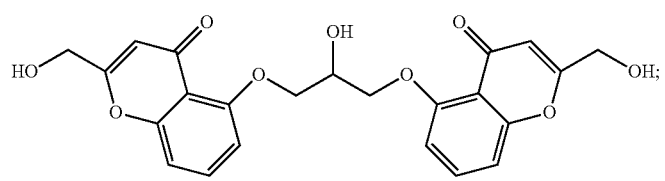
Triol-Cromolyn
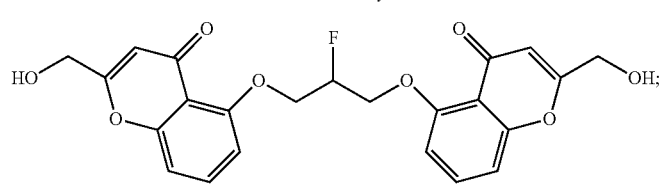
F-Triol-Cromolyn
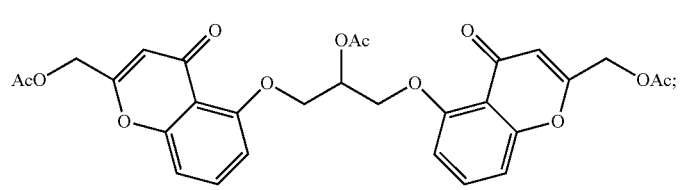
Ac-Triol-Cromolyn
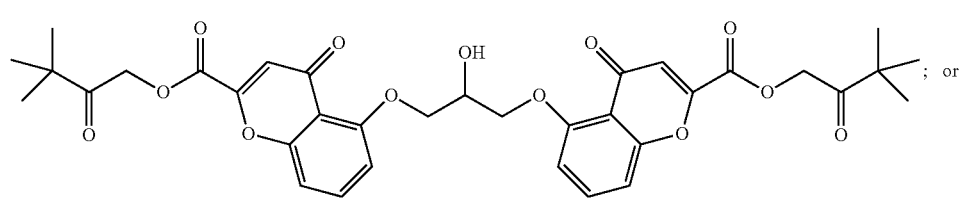
POM-Cromolyn -continued

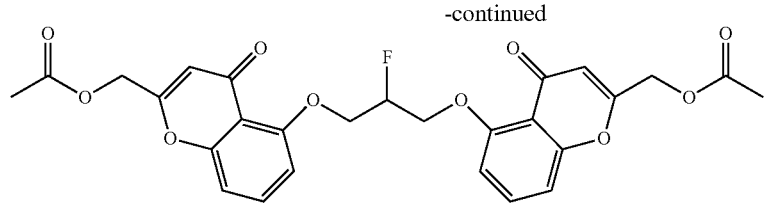

C₂₇H₂₃FO₁₀
Mol. Wt.: 526.46

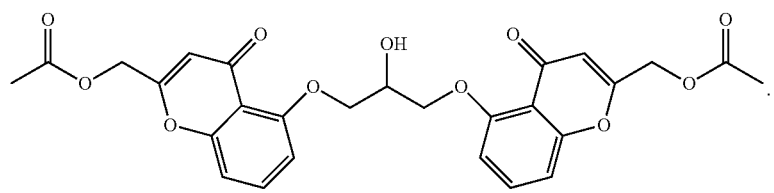

C₂₇H₂₄O₁₁
Mol. Wt.: 524.47

In yet other embodiments, the neuron inflammation condition is at least one of ALS, AD, ischemic stroke, or prion disease. In one embodiment, the compounds may be administered intraperitoneally (IP) and/or intravenously (IV). The compounds may be administered at a dose between about 1 mg and about 1000 mg per day. The method of administration may be transdermally or by inhalation.

In another embodiment, the method is a method of treating ALS further comprising co-administering CD4+; siRNA; miRNA that ameliorate ALS; glial morphology modifier; SOD1 control; Riluzole; or another M1; M2 conversion active drug that controls neuroinflammation.

In certain embodiments, the invention relates to any of the methods described herein, provided the compound is not cromolyn disodium. In certain embodiments, the invention relates to any of the methods described herein, provided the compound is not cromolyn disodium, F-cromolyn disodium, ET-cromolyn, or F-ET-cromolyn when the neuron inflammation condition is AD.

In certain embodiments, the invention relates to any one of the following compounds:

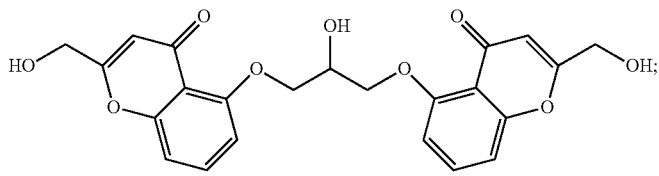

Triol-Cromolyn

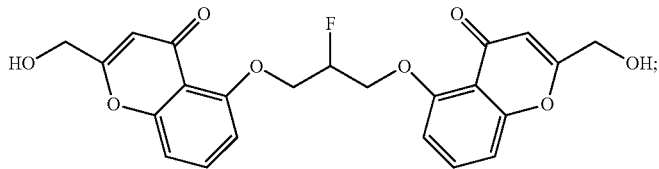

F-Triol-Cromolyn

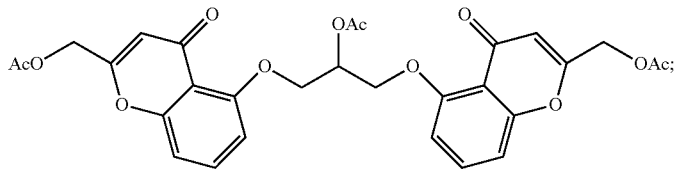

Ac-Triol-Cromolyn

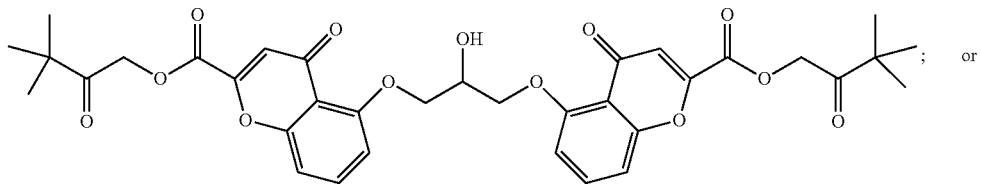

; or

POM-Cromolyn

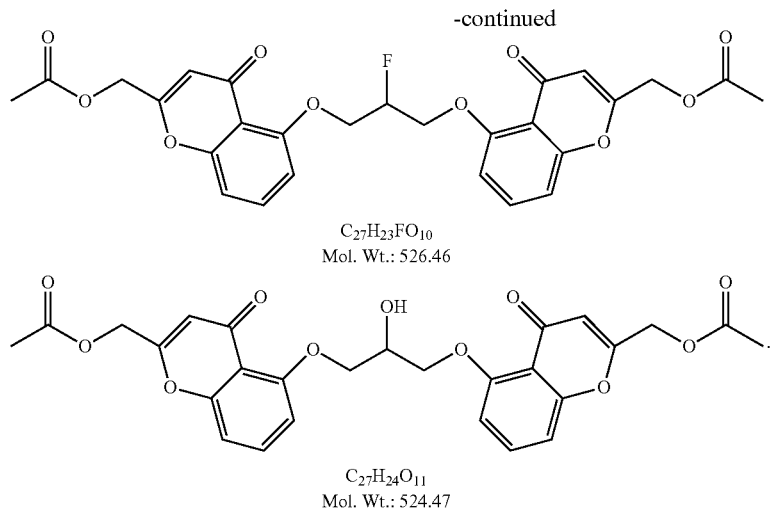

C$_{27}$H$_{23}$FO$_{10}$
Mol. Wt.: 526.46

C$_{27}$H$_{24}$O$_{11}$
Mol. Wt.: 524.47

Afterwards, cells were incubated with DMSO or cromolyn derivatives in the presence of the Aβ42 peptide for additional 2 hours. Cell lysates were analyzed for intracellular levels of Aβ42 using an Aβ42-specific ELISA kit. Treatment with the cromolyn derivative C4 at 75 μM led to increased uptake of Aβ42 in BV2-CD33$^{WT}$ cells in comparison to DMSO treatment and displayed a dose-dependent effect at 50 μM.

Figure 11:
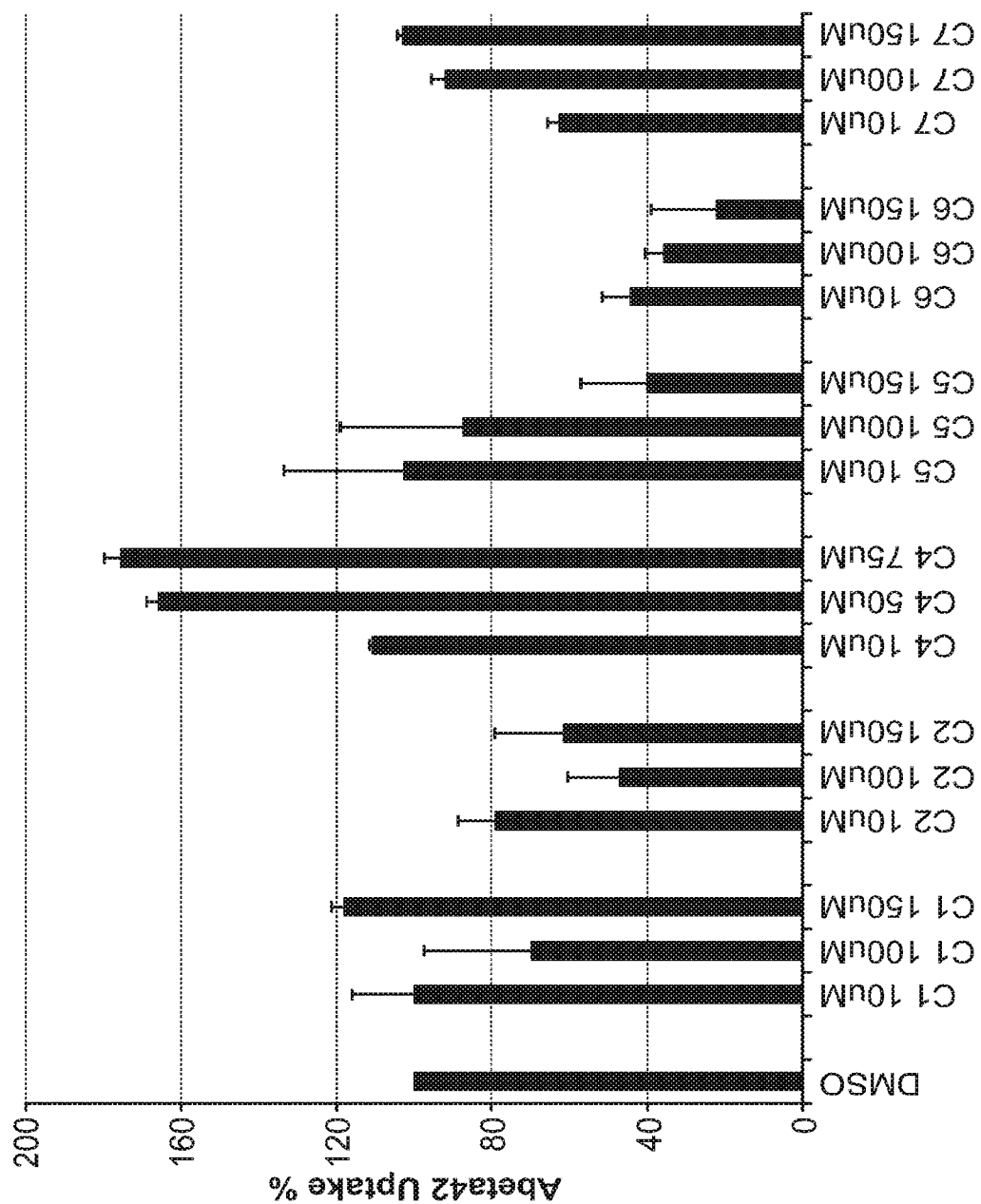

FIG. 11 graphically illustrates that compound C4 promotes Aβ42 uptake in BV2-CD33$^{WT}$ cells. BV2-CD33$^{WT}$ cells were treated with DMSO (vehicle) or cromolyn derivatives (C1, C2, and C4-7) at different concentrations for 3 hours. Afterwards, cells were treated with DMSO or cromolyn derivatives and soluble Aβ42 peptide for 2 hours. Cell lysates were analyzed using Aβ42-specific ELISA kit and intracellular Aβ42 levels were quantified. The cromolyn derivative C4 effectively induced Aβ42 uptake at 50 and 75 μM in BV2-CD33$^{WT}$ cells in comparison to cells treated with DMSO.

DETAILED DESCRIPTION

Ischemic stroke, Alzheimer's Disease (AD), Amyotrophic Lateral Sclerosis (ALS or Lou Gehrig's disease), Prion and other neurodegenerative disorders are associated with microglial activation and mast cell migration, as well as with monocytes and other cell types that produce a barrage of toxic cytokines and debris that enhance inflammation. In certain embodiments, the invention encompasses anti-inflammatory compounds to reduce the toxic effect of pro-inflammatory cytokines by converting microglia from a pro-inflammatory M1 state to an M2 state in which the toxic effects are reduced and their phagocytic activity toward amyloidosis, tauopathies and other cytotoxic events is enhanced. In certain embodiments, the invention also encompasses the use of the compounds to affect therapy early in the disease process.

Many drugs used as anti-inflammatory agents showed no efficacy in the conversion of microglia from M1 to M2, nor do they enhance the modulation of microglia from M1 to M2. To the best of applicant's knowledge, the compounds described herein are the only effective, non-cytokine (e.g. IL-10) compounds exhibiting M1-to-M2 activity. Thus, in certain embodiments, the invention encompasses the compounds and the methods of treating neuron inflammation conditions by administration of a therapeutic effective amount of at least one of the compounds.

In certain embodiments, compounds of the invention include those having the following formula and their analogs and isomers:

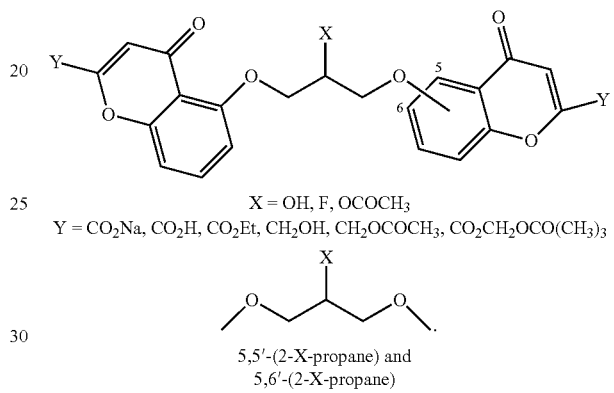

X = OH, F, OCOCH$_3$
Y = CO$_2$Na, CO$_2$H, CO$_2$Et, CH$_2$OH, CH$_2$OCOCH$_3$, CO$_2$CH$_2$OCO(CH$_3$)$_3$ 5,5'-(2-X-propane) and
5,6'-(2-X-propane)

In addition, X may include, but is not limited to, halides, and OCO(C$_1$-C$_8$ alkyls). Alkyl groups include, but are not limited to, methyl, ethyl, propyl, isopropyl, butyl, isobutyl, tert-butyl, and pentyl. Halides include fluoro, chloro, bromo, and iodo. Y may include, but is not limited to, —CH$_2$OH, —CH$_2$OAc, or —CH$_2$OMe. Preferably, the compounds of the invention include those compounds attached at the 5 position.

Specific compounds with the scope of the invention include:

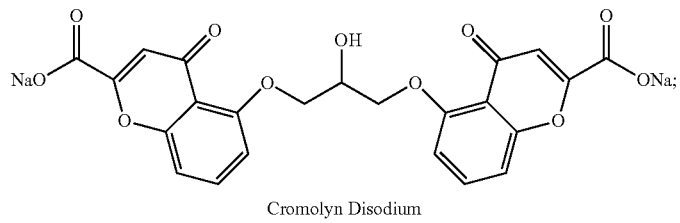

Cromolyn Disodium

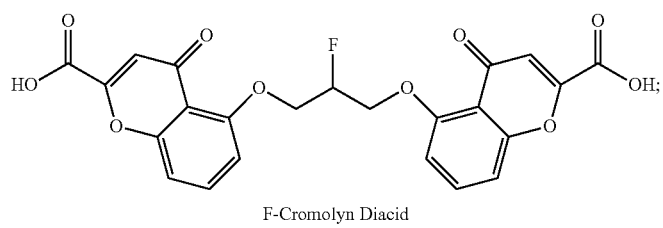

F-Cromolyn Diacid

-continued
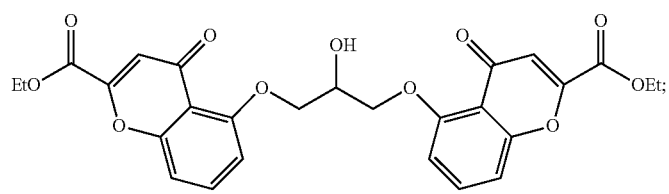
ET-Cromolyn
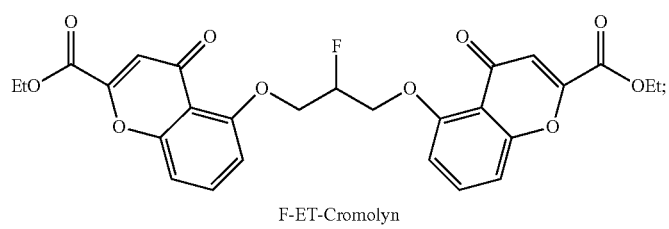
F-ET-Cromolyn
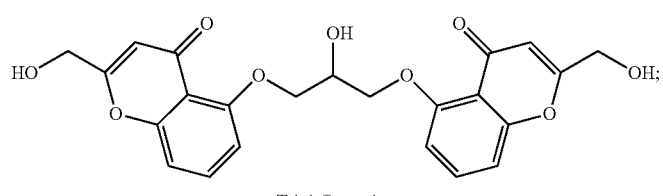
Triol-Cromolyn
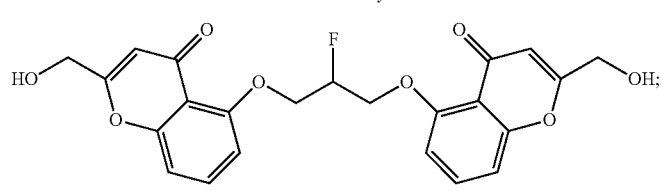
F-Triol-Cromolyn
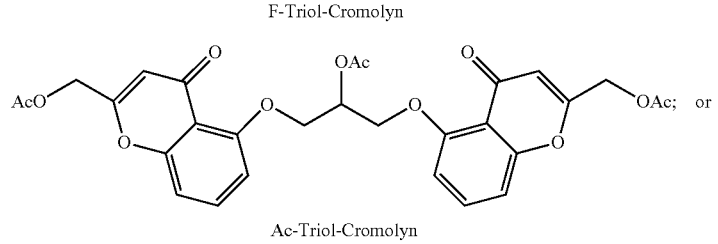
Ac-Triol-Cromolyn
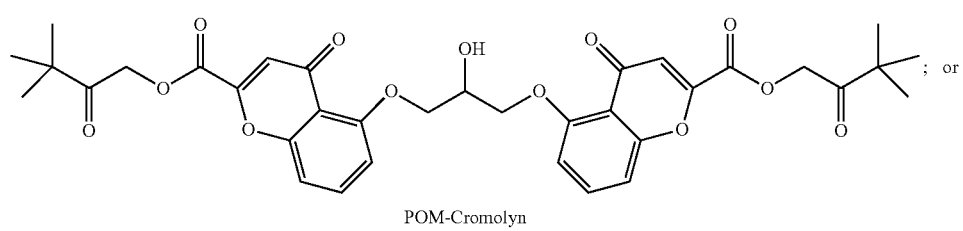
POM-Cromolyn
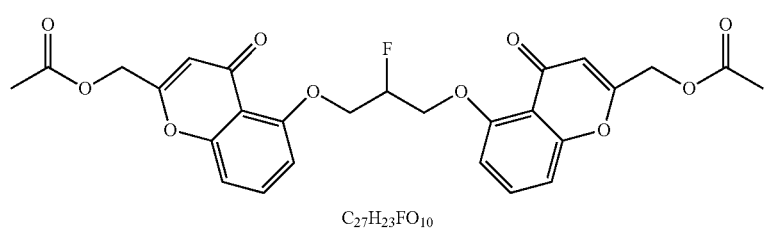
$C_{27}H_{23}FO_{10}$
Mol. Wt.: 526.46

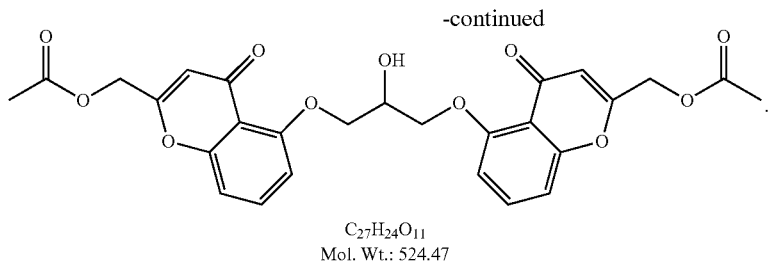

C₂₇H₂₄O₁₁
Mol. Wt.: 524.47

In certain embodiments, compounds also include 5-[3-(2-carboxy-4-oxochromen-5-yl)oxy-2-hydroxypropoxy]-4-oxochromene-2-carboxylic acid derivatives and isomeric forms.

In certain embodiments, the invention encompasses methods of treating a variety of neuron inflammation conditions. Neuron inflammation conditions include, but are not limited to, diseases such as ALS, autism spectrum disorder (ASD), ischemic stroke, and prion disease. In certain embodiments, the compounds may be used to treat ALS including, but not limited to, slowing down or halting the progression of the disease. In certain embodiments, the compounds may be administered in combination with other anti-inflammatory agents to control the spread of the progressive and fatal effect of ALS.

In certain embodiments, the invention encompasses a combination treatment for ALS of M1, M2 conversion active drugs that control neuroinflammation, such as the drugs in the above formulas, with other immune targeting therapies such as CD4+, siRNA, miRNA that ameliorates ALS, glial morphology modifiers, SOD1 controls, or Riluzole, the only approved drug for ALS.

In other embodiments, the compounds will slow down or halt neuron damage for neurons located in the brain stem and/or the spinal cord, neurons, or motor neurons that affect voluntary body muscles.

In certain embodiments, the compounds may be administered using known methods for the administration of drugs, for example, IP, IV, transdermally, by inhalation. In certain embodiments, the invention relates to methods of treating or slowing down the aggressive progression of a neurological disease, such as AD, Ischemic Stroke, ALS, or Prion, and the compound is administered by infusion or intraperitoneal administration.

In certain embodiments, the invention also provides pharmaceutical compositions comprising one or more compounds described herein in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds may be incorporated into transdermal patches designed to deliver the appropriate amount of the drug in a continuous fashion.

For preparing solid compositions such as powders and tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture. When referring to these preformulation compositions as homogeneous, it is meant that the active ingredient is dispersed evenly throughout the composition so that the composition may be easily subdivided into equally effective unit dosage forms.

In some embodiments, a dry powder composition is micronized for inhalation to the lungs. See for example, U.S. Patent Application publication 2016/0263257, expressly incorporated herein by reference in its entirety, and in particular regarding the dry powder cromolyn formulations described therein. In other embodiments, the dry powder composition further comprises at least one excipient. In certain embodiments, the at least one excipient comprises Lactose monohydrate and/or Magnesium stearate.

In certain embodiments, the compounds may be administered in doses that treat the particular indication. In particular, the dose is specifically tailored to lead to blood, brain, and CSF concentrations that allow the drugs to act as M1-to-M2 modifiers. Such doses may include from about 1 mg to about 1000 mg per day.

The dosage of the active agents will generally be dependent upon a number of factors, including the pharmacodynamic characteristics of the compound, mode and route of administration of the compound, the health of the patient being treated, the extent of treatment desired, the nature and kind of concurrent therapy, if any, and the frequency of treatment and the nature of the effect desired. In general, dosage ranges of the compound often range from about 0.001 to about 250 mg/kg body weight per day. For a normal adult having a body weight of about 70 kg, a dosage may range from about 0.1 to about 25 mg/kg body weight.

However, some variability in this general dosage range may be required depending on the age and weight of the subject being treated, the intended route of administration, the particular agent being administered, and the like. Importantly, the determination of dosage ranges and optimal dosages for a particular mammal is also well within the ability of one of ordinary skill in the art having the benefit of the instant disclosure.

Dosages for compounds may be as low as 5 ng/d. In certain embodiments, about 10 ng/day, about 15 ng/day, about 20 ng/day, about 25 ng/day, about 30 ng/day, about 35 ng/day, about 40 ng/day, about 45 ng/day, about 50 ng/day, about 60 ng/day, about 70 ng/day, about 80 ng/day, about 90 ng/day, about 100 ng/day, about 200 ng/day, about 300 ng/day, about 400 ng/day, about 500 ng/day, about 600 ng/day, about 700 ng/day, about 800 ng/day, about 900 ng/day, about 1 µg/day, about 2 µg/day, about 3 µg/day, about 4 µg/day, about 5 µg/day, about 10 µg/day, about 15 µg/day, about 20 µg/day, about 30 µg/day, about g/day, about 50 µg/day, about 60 µg/day, about 70 µg/day, about 80 µg/day, about 90 µg/day, about 100 µg/day, about 200 µg/day, about 300 µg/day, about 400 µg/day about 500 µg/day, about 600 µg/day, about 700 µg/day, about 800

µg/day, about 900 µg/day, about 1 mg/day, about 2 mg/day, about 3 mg/day, about 4 mg/day, about 5 mg/day, about 10 mg/day, about 15 mg/day, about 20 mg/day, about 30 mg/day, about 40 mg/day or about 50 mg/day of the compound is administered.

Dosage ranges for active agents may be from 5 ng/d to 100 mg/day. In certain embodiments, dosage ranges for active agents may be from about 5 ng/day to about 10 ng/day, about 15 ng/day, about 20 ng/day, about 25 ng/day, about 30 ng/day, about 35 ng/day, about 40 ng/day, about 45 ng/day, about 50 ng/day, about 60 ng/day, about 70 ng/day, about 80 ng/day, about 90 ng/day, about 100 ng/day, about 200 ng/day, about 300 ng/day, about 400 ng/day, about 500 ng/day, about 600 ng/day, about 700 ng/day, about 800 ng/day, or about 900 ng/day. In certain embodiments, dosage ranges for compounds may be from about 1 µg/day to about 2 µg/day, about 3 µg/day, about 4 µg/day, about 5 jig/day, about 10 µg/day, about 15 µg/day, about 20 µg/day, about 30 µg/day, about 40 µg/day, about 50 µg/day, about 60 µg/day, about 70 µg/day, about 80 µg/day, about 90 µg/day, about 100 µg/day, about 200 µg/day, about 300 µg/day, about 400 µg/day about 500 µg/day, about 600 µg/day, about 700 µg/day, about 800 µg/day, or about 900 µg/day. In certain embodiments, dosage ranges for active agents may be from about 1 mg/day to about 2 mg/day, about 3 mg/day, about 4 mg/day, about 5 mg/day, about 10 mg/day, about 15 mg/day, about 20 mg/day, about 30 mg/day, about 40 mg/day, about 50 mg/day, about 60 mg/day, about 70 mg/day, about 80 mg/day, about 90 mg/day, about 100 mg/day, about 200 mg/day, about 300 mg/day, about 400 mg/day, about 500 mg/day, about 600 mg/day, about 700 mg/day, about 800 mg/day, or about 900 mg/day.

In certain embodiments, the compounds are administered in pM or nM concentrations. In certain embodiments, the compounds are administered in about 1 pM, about 2 pM, about 3 pM, about 4 pM, about 5 pM, about 6 pM, about 7 pM, about 8 pM, about 9 pM, about 10 pM, about 20 pM, about 30 pM, about 40 pM, about 50 pM, about 60 pM, about 70 pM, about 80 pM, about 90 pM, about 100 pM, about 200 pM, about 300 pM, about 400 pM, about 500 pM, about 600 pM, about 700 pM, about 800 pM, about 900 pM, about 1 nM, about 2 nM, about 3 nM, about 4 nM, about 5 nM, about 6 nM, about 7 nM, about 8 nM, about 9 nM, about 10 nM, about 20 nM, about 30 nM, about 40 nM, about 50 nM, about 60 nM, about 70 nM, about 80 nM, about 90 nM, about 100 nM, about 300 nM, about 400 nM, about 500 nM, about 600 nM, about 700 nM, about 800 nM, or about 900 nM, concentrations.

In certain embodiments, the dosage form is a solid dosage form, and the size of the compound in the dosage form is important. In certain embodiments, the compound is less than about 3 µm, less than about 2 µm, or less than about 1 µm in diameter. In certain embodiments, the active agent is about 0.1 µm to about 3.0 µm in diameter. In certain embodiments, the active agent is from about 0.5 µm to about 1.5 µm in diameter. In certain embodiments, the active agent is about 0.2 µm, about 0.3 µm, about 0.4 µm, about 0.5 µm, about 0.6 µm, about 0.7 µm, about 0.8 µm, about 0.9 µm, about 1.0 µm, about 1.1 µm, about 1.2 µm, about 1.3 µm, about 1.4 µm, or about 1.5 µm in diameter.

For example, a formulation intended for oral administration to humans may contain from about 0.1 mg to about 5 g of the active agent (or compound) compounded with an appropriate and convenient carrier material varying from about 5% to about 95% of the total composition. Unit dosages will generally contain between about 0.5 mg to about 1500 mg of the active agent. The dosage may be about: 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg 25 mg, 26 mg, 27 mg, 28 mg, 29 mg, 30 mg, 31 mg, 32 mg, 33 mg, 34 mg 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 55 mg, 60 mg, 65, mg, 70 mg, 75 mg, 80 mg, 85 mg, 90 mg, 95 mg, 100 mg, 200 mg, 300 mg, 400 mg, 500 mg, 600 mg, 800 mg, or 100 mg, etc., up to about 1500 mg of the compound.

In certain embodiments, the invention relates to combination of two active agents. In certain embodiments, it may be advantageous for the pharmaceutical combination to be comprised of a relatively large amount of the first component compared to a second component. In certain instances, the ratio of the first active agent to the second active agent is about: 200:1, 190:1, 180:1, 170:1, 160:1, 150:1, 140:1, 130:1, 120:1, 110:1, 100:1, 90:1, 80:1, 70:1, 60:1, 50:1, 40:1, 30:1, 20:1, 15:1, 10:1, 9:1, 8:1, 7:1, 6:1, or 5:1. It further may be preferable to have a more equal distribution of pharmaceutical agents. In certain instances, the ratio of the first active agent to the second active agent is about: 4:1, 3:1, 2:1, 1:1, 1:2, 1:3, or 1:4. It may also be advantageous for the pharmaceutical combination to have a relatively large amount of the second component compared to the first component. In certain instances, the ratio of the second active agent to the first active agent is about 200:1, 190:1, 180:1, 170:1, 160:1, 150:1, 140:1, 130:1, 120:1, 110:1, 100:1, 90:1, 80:1, 70:1, 60:1, 50:1, 40:1, 30:1, 20:1, 15:1, 10:1, 9:1, 8:1, 7:1, 6:1, or 5:1. A composition comprising any of the above identified combinations of the first therapeutic agent and second therapeutic agent may be administered in divided doses about 1, 2, 3, 4, 5, 6, or more times per day or in a form that will provide a rate of release effective to attain the desired results. The dosage form may contain both the first and second active agents. The dosage form may be administered one time per day if it contains both the first and second active agents.

For example, a formulation intended for oral administration to humans may contain from about 0.1 mg to about 5 g of the first therapeutic agent and about 0.1 to about 5 g of the second therapeutic agent, both of which are compounded with an appropriate and convenient about of carrier material varying from about 5% to about 95% of the total composition. Unit dosages will generally contain between about 0.5 mg to about 1500 mg of the first therapeutic agent and 0.5 mg to 1500 mg of the second therapeutic agent. The dosage may be about: 25 mg, 50 mg, 100 mg, 200 mg, 300 mg, 400 mg, 500 mg, 600 mg, 800 mg, or 100 mg, etc., up to about 1500 mg of the first therapeutic agent. The dosage may be about: 25 mg, 50 mg, 100 mg, 200 mg, 300 mg, 400 mg, 500 mg, 600 mg, 800 mg, or 100 mg, etc., up to about 1500 mg of the second therapeutic agent.

In certain embodiments, the inventions relates to a method of treating a Alzheimer's disease comprising administering by inhalation a micronized, dry powder comprising about 1 mg to 100 mg of Cromolyn Disodium per day to a patient in need thereof.

EXAMPLES

Example 1

Our studies in PS1/PSS animal model showed that Cromolyn sodium impacted the interaction of microglial cells with amyloid deposits and eventually affected Aβ clearance by microglia. We first performed a double immunostaining between Aβ and the microglial marker Iba1 in brain sections of mice treated with PBS or the highest dose of Cromolyn sodium (3.15 mg/kg). A systematic analysis of the overlap between both stainings revealed that animals that received Cromolyn Sodium showed a higher percentage of Iba1 immunoreactivity overlapping with amyloid (FIG. 1B), which may indicate a modest increased recruitment of microglia around plaques induced by the compound.

To go further in our understanding of these mechanisms, and considering that evaluating change in microglial function is challenging in vivo, we used an additional in vitro system of Aβ microglial uptake. Synthetic $A\beta_{40}$ and $A\beta_{42}$ peptides were applied to microglia in culture in the presence or absence of Cromolyn Sodium.

Figure 1A:
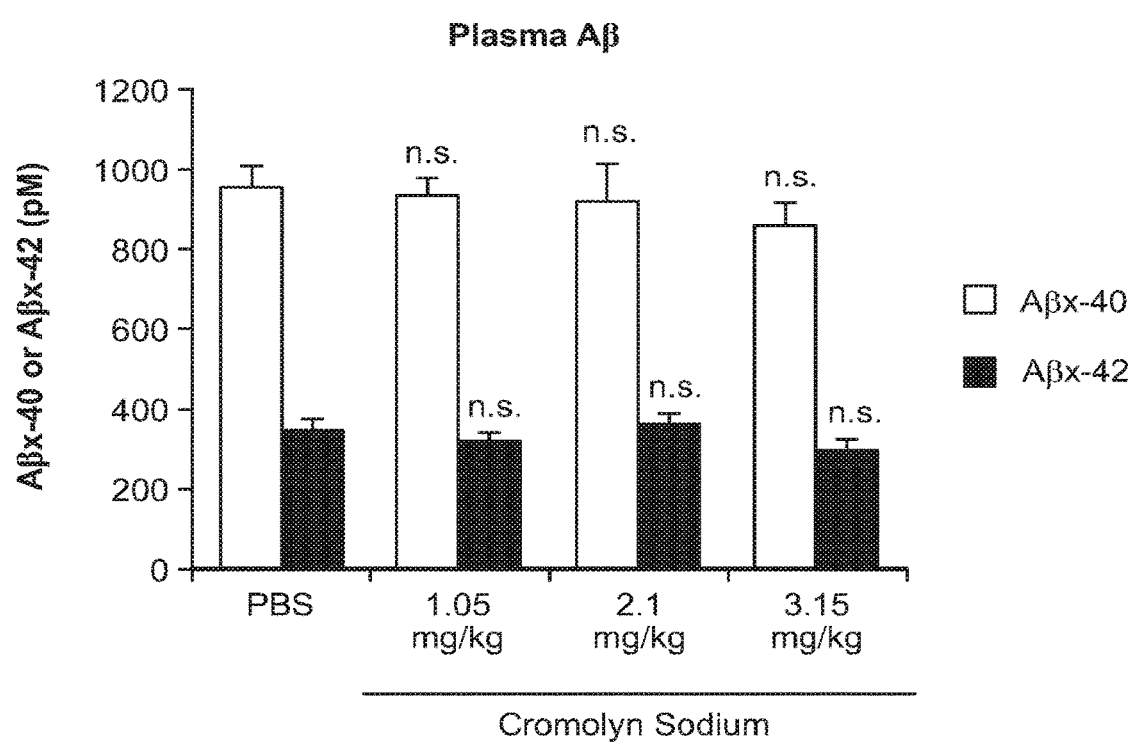
FIG. 1A illustrates the quantification of the plasmatic levels of Aβ$_{x-40}$ and Aβ$_{x-42}$ one week after treatment with PBS or escalating doses of Cromolyn Sodium (n=3-5 mice/group).
Figure 1B:
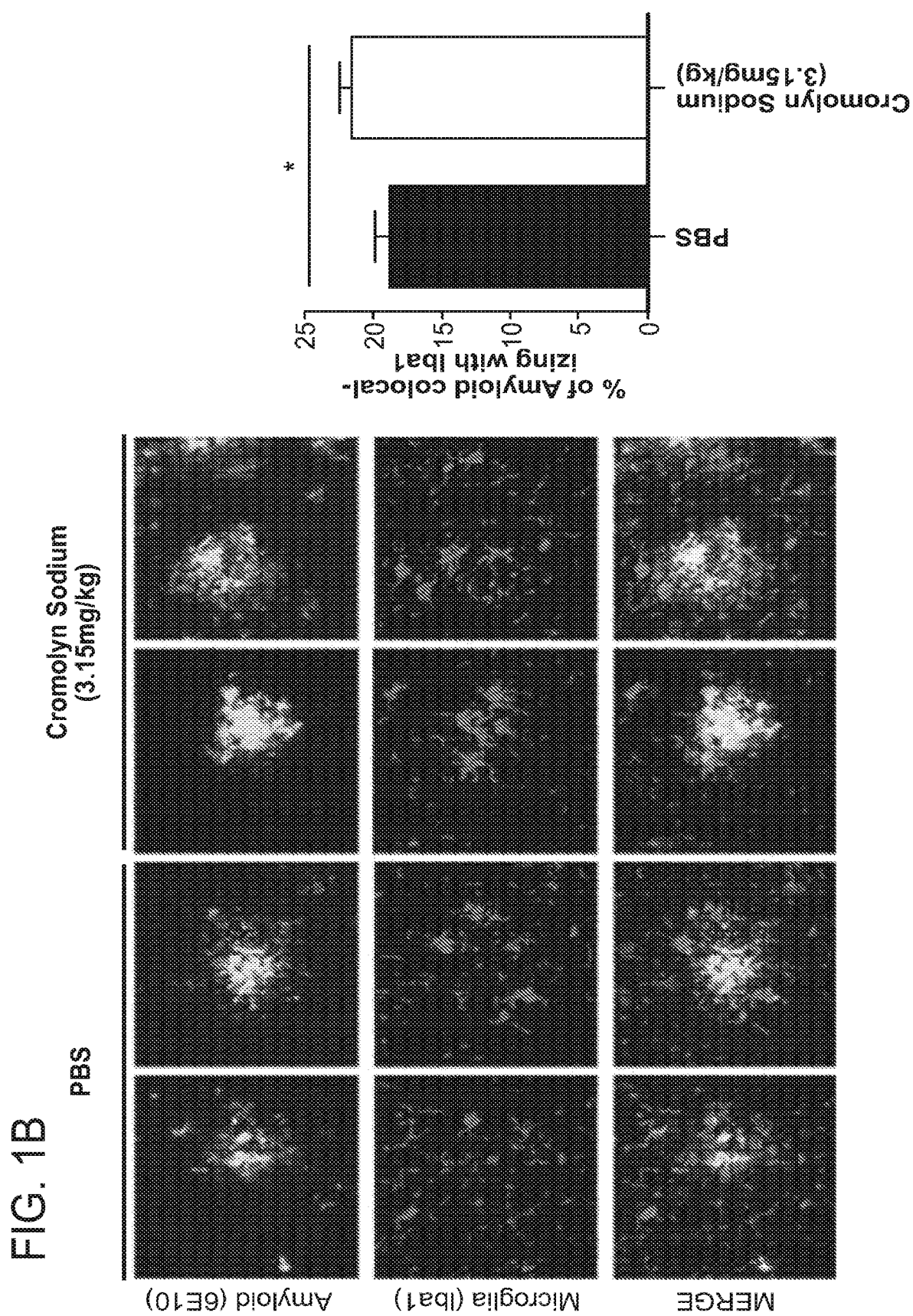
FIG. 1B illustrates representative images of localization of amyloid deposits (6E10) and microglia (Iba1) in mice treated with Cromolyn Sodium (3.15 mg/kg) or PBS daily for seven days. The bar figure illustrates the results from analyzing plaques for each animal. Scale bar=10 μm.
Figure 1C:
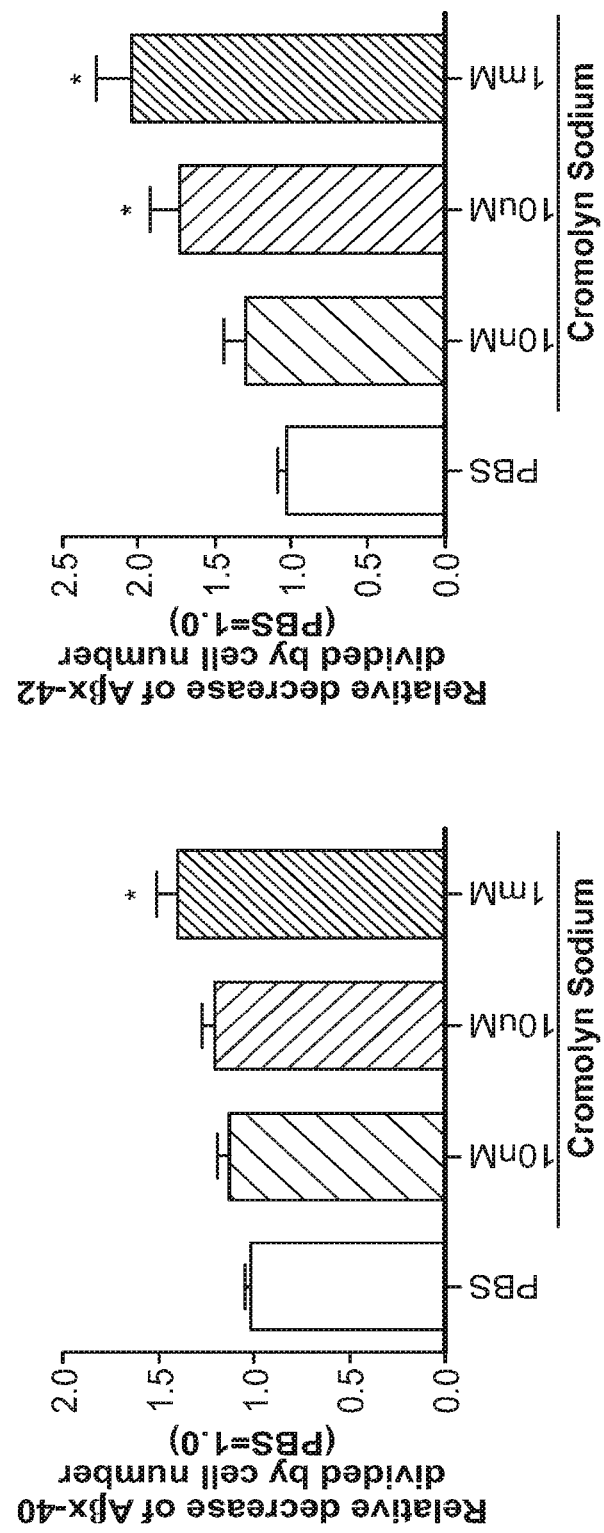
FIG. 1C illustrates the effect of Cromolyn Sodium on microglial Aβ uptake in vitro, where after the incubation, the concentrations of Aβ$_{x-40}$ (FIG. 1C left) Aβ$_{x-42}$ (FIG. 1C, right) in media were measured using Aβ ELISA.

After 16 hours of incubation, we observed a dose dependent decrease of $A\beta_{40}$ and $A\beta_{42}$ levels in presence of Cromolyn Sodium, indicating that the impact of Cromolyn Sodium on Aβ aggregation mechanisms may promote Aβ clearance by microglial uptake (FIG. 1C). The combination of those in vivo and in vitro results may suggest that, in addition to inhibiting Aβ fibrillization, Cromolyn Sodium affected microglial activation and Aβ clearance.

Cromolyn Sodium does not affect the levels of Aβ in the plasma but promotes microglial Aβ clearance. FIG. 1A illustrates the quantification of the plasmatic levels of $A\beta_{x-40}$ and $A\beta_{x-42}$ one week after treatment with PBS or escalating doses of Cromolyn Sodium (n=3-5 mice/group). FIG. 1B illustrates representative images of localization of amyloid deposits (6E10) and microglia (Iba1) in mice treated with Cromolyn Sodium (3.15 mg/kg) or PBS daily for seven days. The percentage of amyloid occupied by Iba1 positive processes was calculated for each deposit and showed an increased overlap between Aβ and Iba1 after treatment with Cromolyn Sodium (n=3 mice for PBS and n=5 mice for Cromolyn Sodium). Between 20 to 20 plaques were evaluated for each animal). Scale bar=10 µm. FIG. 1C illustrates the effect of Cromolyn Sodium on microglial Aβ uptake in vitro. Microglial cells were cultured and incubated with 50 nM of synthetic $A\beta_{40}$ or $A\beta_{42}$ and 0, 10 nM, 10 µM or 1 mM of Cromolyn Sodium for 16 hours. After the incubation, the concentrations of $A\beta_{x-40}$ (FIG. 1C left) $A\beta_{x-42}$ (FIG. 1C, right) in media were measured using Aβ ELISA and normalized with microglia cell number and according to the PBS control condition. (n=3 experiments; *, P<0.05, **, P<0.01)

Example 2

Figure 2:
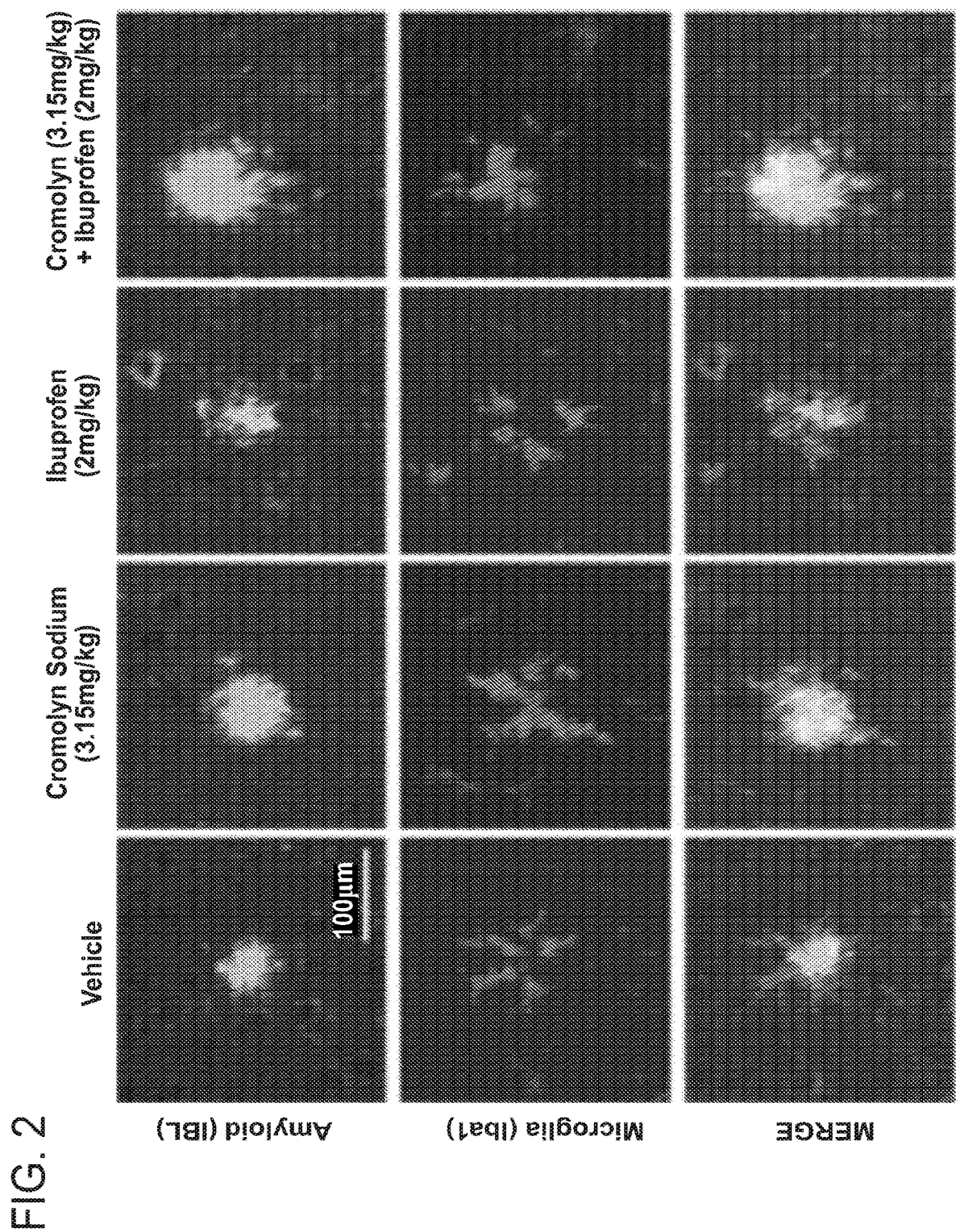
FIG. 2 illustrates the plaques and the microglial cells surrounding those deposits in Tg-2576 mice of the study of Example 2. The figure shows representative pictures of amyloid deposits and Iba-1 positive microglia.

In other animal studies of microglia activation and M1, M2 conversion showed that cromolyn is the only of many drugs tested that effected this change and exhibited phagocytic activity. FIG. 2 illustrates representative plaques of all the plaques and the microglial cells surrounding those deposits in Tg-2576 mice of the study. An image analysis looking at the percentage of Iba-1 positive processes colocalizing with the amyloid staining versus the total amount of Iba-1 signal surrounding the plaque demonstrated that there was more Iba-1/Amyloid colocalization when the mice were treated with Cromolyn Sodium as opposed to any other groups. This result correlates with our results in Example 1 and our in vitro data.

Figure 3:
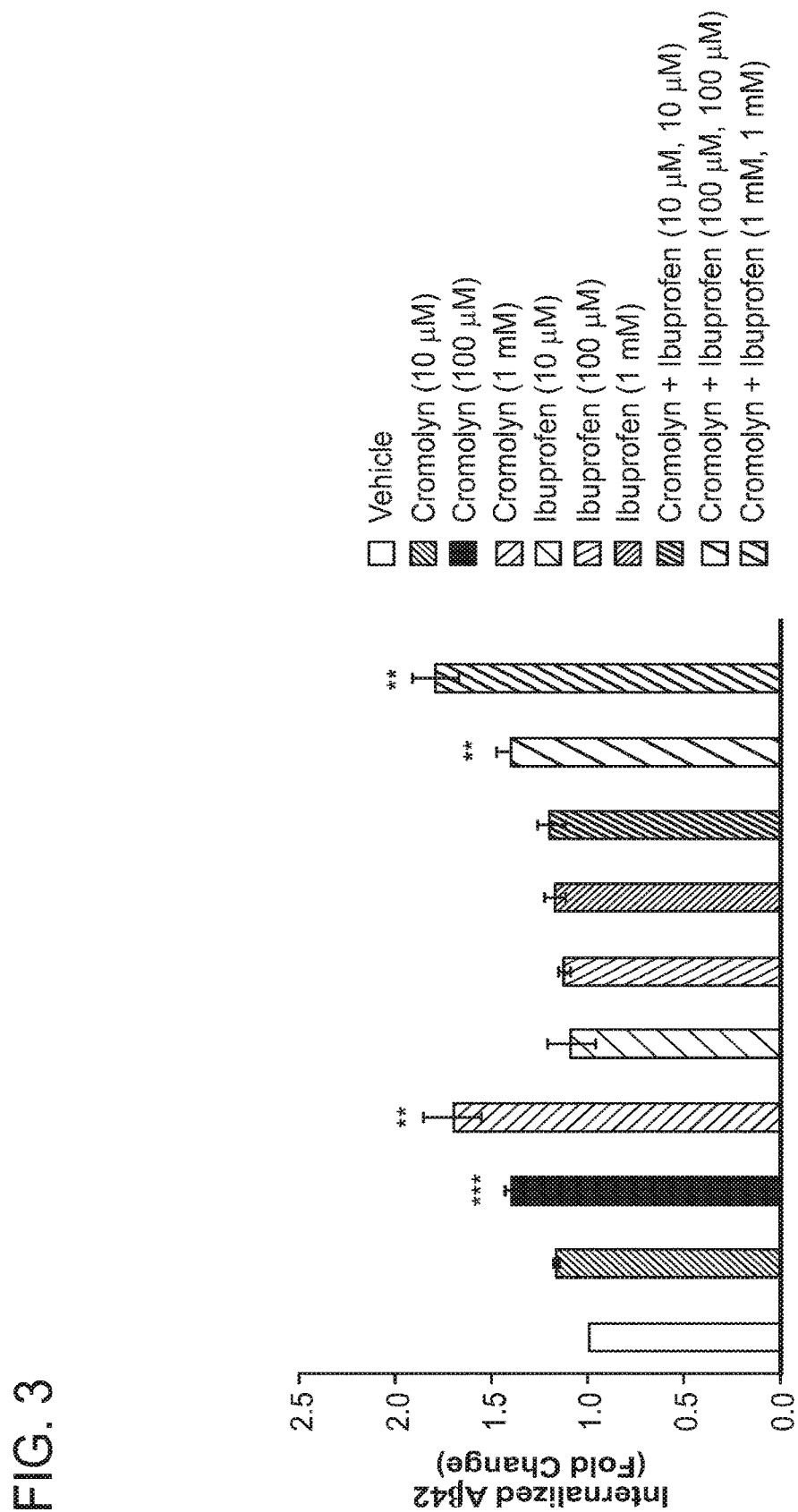
FIG. 3 illustrates the results of BV2 microglial cells treated with cromolyn, and with cromolyn and ibuprofen exhibit increased Aβ$_{42}$ uptake levels relative to BV2 microglia treated with the vehicle.

Cromolyn, but not ibuprofen promotes microglial $A\beta_{42}$ uptake, their combination improved uptake over either ibuprofen or cromolyn alone. BV2 microglial cell cultures were treated with cromolyn and/or ibuprofen (10 µM, 100 µM, 1 mM) for 16 hours. Afterwards, cells were incubated with soluble $A\beta_{42}$ and the compounds for 3 hours. After incubation, cells were collected for ELISA analysis. BV2 microglial cells treated with cromolyn (100 µM, 1 mM), and with cromolyn and ibuprofen (100 µM, 1 mM for each compound) exhibit increased $A\beta_{42}$ uptake levels relative to BV2 microglia treated with the vehicle. Results were derived from three independent experiments; p<0.01, *p<0.001, one-way ANOVA, Tukey's test). Data are represented as mean±SEM. FIG. 3 graphically illustrates the results of BV2 microglial cells treated with cromolyn, and with cromolyn and ibuprofen exhibit increased Aβ42 uptake levels relative to BV2 microglia treated with the vehicle.

Example 3: Compound Synthesis 5,5'-[(2-Hydroxy-1,3-propanediyl)bis(oxy)]bis[4-oxo-4H-1-benzopyran-2-carboxylic acid diethyl ester

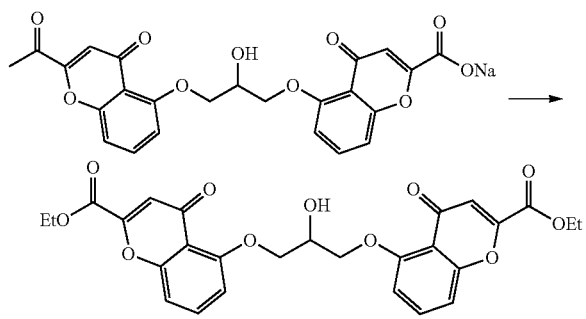

A suspension of cromolyn sodium salt (1.0 g, 2 mmol) in EtOH (100 mL) and con. HCl (1 mL) was heated in a sealed reactor tube for 24 h at 100° C. The white solid was dissolved to give a clear colorless solution while hot. It was allowed to cool to room temperature and $NaHCO_3$ (1.0 g) was added. After stirring for 30 min at 25° C., solvent was removed by roto-evaporation. Chromatography on silica gel of the crude material using 5:95 methanol/methylene chloride yielded the diethyl ester (0.8 g, 76% yield); mp 154-156° C.; $^1$H NMR ($CDCl_3$, 300 MHz) δ 1.42 (t, 3H, J=7.1 Hz, $CH_3$), 2.73 (br s, 1H, OH), 4.44 (q, 4H, J=7.1 Hz, $2OCH_2CH_3$), 4.32-4.59 (m, 5H, CHOH, $2OCH_2$), 6.80 (s, 2H, 2 vinyl-H), 6.99 (d, 2H, J=8.24 Hz, 2Aro-H), 7.12 (d, 2H, J=8.24 Hz, 2Aro-H), 7.17 (d, 2H, J=8.24 Hz, 2Aro-H), 7.71 (t, 2H, J=8.24 2Aro-H).

5,5'-[(2-Fluoro-1,3-propanediyl)bis(oxy)]bis[4-oxo-4H-1-benzopyran-2-carboxylic acid diethyl ester

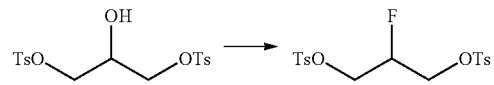 [SMILES: Cc1ccc(S(=O)(=O)OCC(O)COS(=O)(=O)c2ccc(C)cc2)cc1 ; Cc1ccc(S(=O)(=O)OCC(F)COS(=O)(=O)c2ccc(C)cc2)cc1]

3-Bis(4-methylbezenesulfonate)-2-fluoropropanediol

A solution of 1,3-bis(4-methylbezenesulfonate propanetriol (2.7 g, 6.78 mmol) in methylene chloride (20 mL) at 0-5° C. was treated with DAST (2.18 g, 13.6 mmol). The mixture was stirred at 0-5° C. for 30 then allowed to warm to 25° C. and stirred for 16 hr. The mixture was poured into a sat'd sodium bicarbonate solution (30 mL) and layers separated. The methylene chloride layer dried (sodium sulfate). After solvent removal, the crude material was chromatographed on silica gel (methylene chloride) to yield 0.82 g (30%) of a solid; mp 99-102° C.; ¹H NMR (CDCl₃), δ 2.5 (s, 6H, CH₃), 4.15 (dd, 4H, J=12.3, 4.6 Hz, CH₂), 4.8 (dq, 1H, J=47, 4.6, CHF), 7.45 (d, 4H, J=8.1 Hz, Aro-H), 7.75 (d, 4H, J=8.4 Hz, Aro-H).

5,5'-(2-fluoropropane-1,3-diyl)bis(oxy)bis(4-oxo-4H-chromene-2-carboxylic acid)

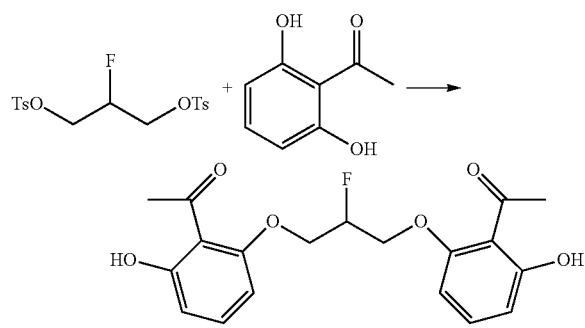

1,3-Bis(2-acetyl-3-hydroxyphenoxy)-2-fluoropropane

A mixture of 3-bis(4-methylbezenesulfonate)-2-fluoropropanediol (1.0, 2.5 mmol), 2,6-dihydroxyacetophenone (0.76 g, 5.0 mmol) and potassium carbonate (0.69 g) in acetonitrile (40 mL) was heated under reflux for 16 hr. The mixture was filtered and the filtrate was evaporated. The crude material was chromatographed on silica gel (acetonitrile/methylene chloride 5:95) to yield 0.57 g (40%) of product; mp 162-165° C.; ¹H NMR (d6-DMSO), δ 2.5 (s, 6H, 2CH₃), 4.38 (m, 4H, 2CH₂), 5.22 (br d 1H, J=49 Hz, CHF), 6.45 (m, 4H, 4Aro-H), 7.28 (t, 2H, J=4.55 Hz, 2Aro-H).

5,5'-[(2-Fluoro-1,3-propanediyl)bis(oxy)]bis[4-oxo-4H-1-benzopyran-2-carboxylic acid diethyl ester

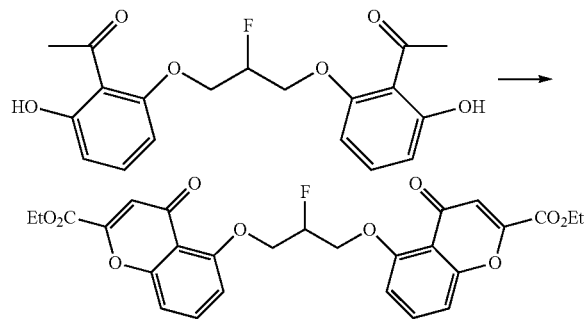

A mixture of 1,3-bis(2-acety-3-hydroxyphenoxy)-2-fluoropropane (200 mg, 0.52 mmol) and ethyl oxalate (2 mL) was added to a solution of sodium ethoxide (87 mg Na) in ethanol (10 mL) and benzene (10 mL). The mixture was heated at reflux for 16 hr, cooled and diluted with ether (50 mL). The precipitated sodium salt was filtered, washed with ether and dried. It was then dissolved in water and acidified with 10% HCl to obtain a sticky solid. The solid was refluxed in ethanol (20 mL) with a catalytic amount of 36% HCL for 1 hr. The mixture was poured into 50 mL of water and extracted twice with methylene chloride (50 mL). The extracts were combined and dried. After solvent removal, the crude material was chromatographed on silica gel (acetonitrile/methylene chloride 10:90) to yield 0.12 g (45%) of product; mp 166-170° C.; ¹H NMR (CDCl₃), δ 1.42 (t, 6H, J=7.14 Hz, 2CH₃), 4.58 (q, 4H, J=7.14 Hz 2CH₂), 4.65 (m, 4H, 2CH₂), 5.35 (dq, 1H, J=46 Hz, J=4.4 HZ, CHF), 6.90 (s, 2H, vinyl-H), 6.95 (d, 2H, J=8.24 Hz, 2Aro-H), 7.13 (d, 2H, J=8.24 Hz, 2Aro-H), 7.17 (d, 2H, J=8.24 Hz, 2Aro-H) 7.6 (t, 2H, J=8.24 2Aro-H).

5,5'-[(2-Fluoro-1,3-propanediyl)bis(oxy)]bis[4-oxo-4H-1-benzopyran-2-carboxylic acid

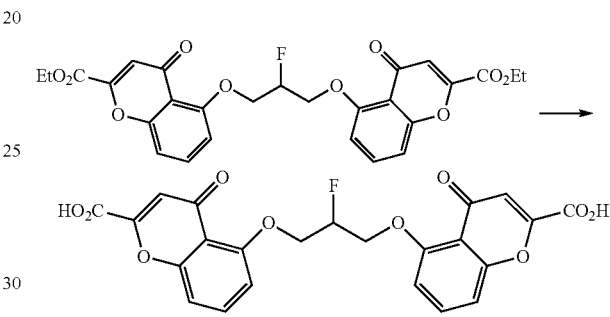

A suspension of 5,5'-[(2-fluoro-1,3-propanediyl)bis(oxy)] bis[4-oxo-4H-1-benzopyran-2-carboxylic acid diethyl ester (100 mg, 0.19 mmol) in methanol (20 mL) and 1 M sodium hydroxide (2 mL) was heated at 80° C. for 1 hr. The solution was acidified with 10% HCl and volatiles were removed. A solution of methanol/methylene chloride (50:50) was added to the solid and the mixture was filtered. Evaporation afforded 76 mg (85%) of product; ¹H NMR (d6-DMSO), δ 4.65 (m, 4H, 2CH₂), 5.32 (br d, 1H, J=46 Hz, CHF), 6.80 (s, 2H, 2vinyl-H), 7.2 (d, 2H, J=8.24 Hz, 2Aro-H), 7.71 (t, 2H, J=8.24 2Aro-H).

5,5'-[(2-Hydroxy-1,3-propanediyl)bis(oxy)]bis[4-oxo-4H-1-benzopyran-2-ethanol

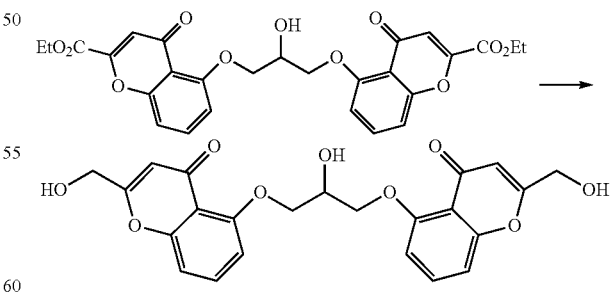

To a suspension of 5,5'-(2-hydroxytrimethylenedioxy)bis (4-oxochromene-2-carboxylic acid) diethyl ester (1.0 g, 1.86 mmol) in methanol (60 ml) and methylene chloride (40 mL) NaBH₄ (0.14 g, 3.72 mmol) was added in portions over a 1 h period. The mixture was stirred at 25° C. until it was clear (approx. 5 h) at which time the solution was quenched by dropwise addition of 1M HCl until acidic. Solvent was evaporated and the residue was extracted with methylene chloride. The combined organic extracts were washed with water and dried over anhydrous sodium sulfate. After evaporation, the residue was purified by column chromatography (5:95 methanol/methylene chloride) to yield 0.5 g (50%) of the triol; $^1$H NMR (DMSO-$d_6$, 300 MHz) δ 2.73 (s, 3H, OH), 4.25-4.36 (m, 9H, 2OCH$_2$, CH—O), 6.13 (s, 2H, 2 vinyl H), 7.04 (d, 2H, J=8.4 Hz, aromatic H), 7.07 (d, 2H, J=8.4 Hz, aromatic H), 7.63 (t, 2H, J=8.2 Hz, aromatic H).

5,5'-[(2-Fluoro-1,3-Propanediyl)Bis(Oxy)]Bis[4-Oxo-4H-1-Benzopyran-2-Ethanol

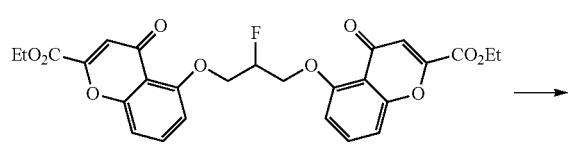

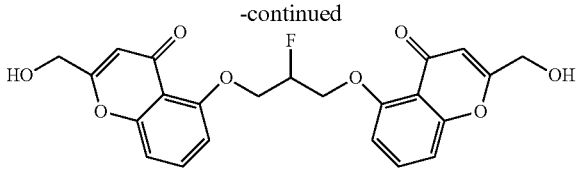

The above procedure for 5,5'-(2-hydroxytrimethylenedioxy)bis(4-oxochromene-2-ethanol) was used. $^1$H NMR (DMSO-$d_6$, 300 MHz) δ 2.73 (s, 3H, OH), 4.25-4.36 (m, 8H, 2OCH$_2$, CH—O), 5.35 (br d, 1H, J=46 Hz, CHF), 6.13 (s, 2H, 2 vinyl H), 7.04 (d, 2H, J=8.4 Hz, aromatic H), 7.07 (d, 2H, J=8.4 Hz, aromatic H), 7.63 (t, 2H, J=8.2 Hz, aromatic H).

5,5'-[(2-Hydroxy-1,3-propanediyl)bis(oxy)]bis[4-oxo-4H-1-benzopyran-2-carboxylic acid bis[(2,2-dimethyl-1-oxopropoxy)methyl] ester

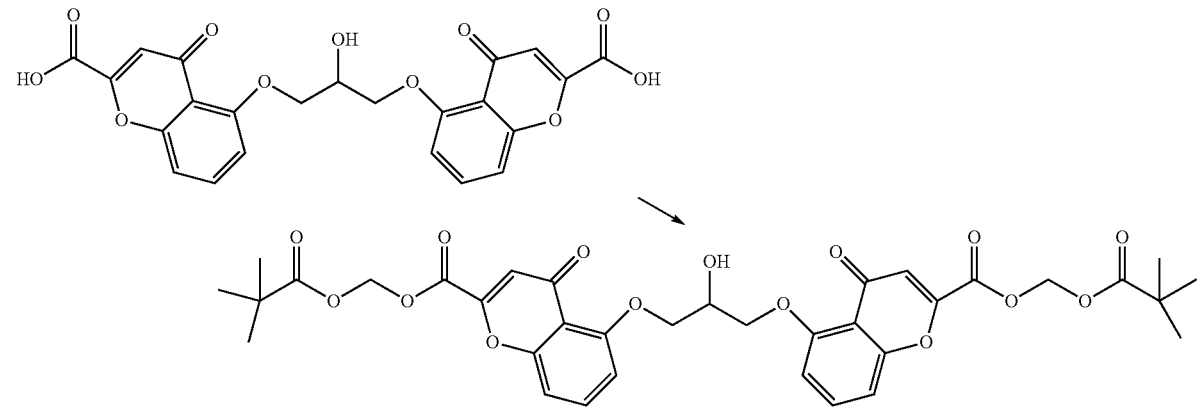

To a stirred solution of cromolyn diacid (1.0 g, 2.7 mm) in 20 mL of DMF was added diisopropylamine (0.7 mL) and 1.0 g (6.5 mmol) chloromethylpivalate. The reaction mixture was stirred at 60° C. for 4 hr, water was added and the mixture was extracted with separated, dried (MgSO$_4$) and the solvent removed in vacuo. The solvent was removed and the residue was chromatographed on silica 4% methanol in methylene chloride to give 1.2 g (65%) of the pivalate compound; mp 135-140° C.; H$^1$ NMR (CDCl), δ 1.24 (s, 18H, CH$_3$), 4.36 (m, 2H, OCH$_2$), 4.49 (m, 1H, CHOH), 4.51 (m, 2H, OCH$_2$), 6.00 (s, 4H, CH—O—CO), 6.98 (m, 4H, 2vinyl-H, 2Aro-H), 7.13 (d, 2H, J=8.24 Hz, 2Aro-H), 7.61 (t, 2H, J=8.24 2Aro-H).

5,5'-[(2-Fluoro-1,3-propanediyl)bis(oxy)]bis[4-oxo-4H-1-benzopyran-2-carboxylic acid bis[(2,2-dimethyl-1-oxopropoxy)methyl] ester

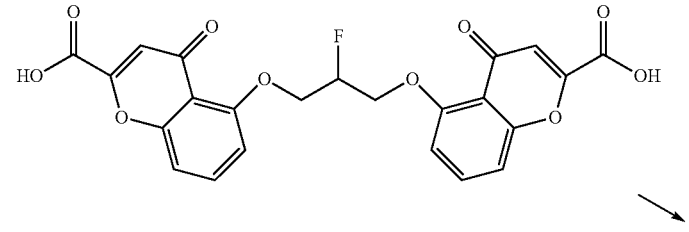

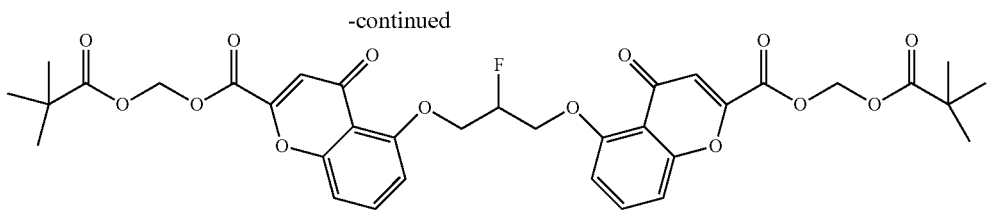

To a stirred solution of 5,5'-[(2-fluoro-1,3-propanediyl) bis(oxy)]bis[4-oxo-4H-1-benzopyran-2-carboxylic acid (1.0 g, 2.1 mmol) in 20 mL of DMF was added iisopropylamine (0.7 mL) and 1.0 g (6.5 mmol) chloromethylpivalate. The reaction mixture was stirred at 60° C. for 4 hr, water was added and the mixture was extracted with separated, dried ($MgSO_4$) and the solvent removed in vacuo. The solvent was removed and the residue was chromatographed on silica using 2% methanol in methylene chloride to give 1.0 g (70%) of the pivalate compound; mp 130-133° C.; δ 1.21 (s, 18H, $CH_3$), 4.36 (m, 4 m, $2OCH_2$), 4.49 (br d, 1H, J=46 Hz, CHF), 6.00 (s, 4H, CH—O—CO), 6.98 (m, 4H, 2vinyl-H, 2Aro-H), 7.13 (d, 2H, J=8.24 Hz, 2Aro-H), 7.61 (t, 2H, J=8.24 2Aro-H).

Triacetate of 5,5'-[(2-hydroxy-1,3-propanediyl)bis (oxy)]bis[4-oxo-4H-1-benzopyran-2-ethanol

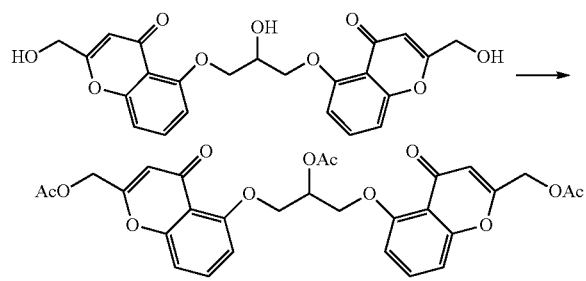

Acetic anhydride (0.5 g, 4.6 mmol)) was slowly added to a mixture of 5,5'-[(2-hydroxy-1,3-propanediyl)bis(oxy)]bis [4-oxo-4H-1-benzopyran-2-ethanol (0.5 g, 1.14 mmol) in pyridine (20 mL) cooled to 0-5° C. The mixture was stirred for 3 hr at 0-5° C. and then allowed to warm to room temperature. TLC indicted the reaction was complete. Methylene chloride was added and the mixture was washed with 10% HCl until the aqueous phase was acidic. The methylene chloride layer was dried over anhydrous sodium sulfate and solvent was evaporated. Chromatography on silica using 3% methanol in methylene chloride gave 0.45 g (72%) of the triacetate compound; mp 122-125° C.; $H^1$ NMR ($CDCl_3$), S 2.16 (s, 9H, $CH_3$), 4.58 (m, 2H, $CH_2OH$), 4.66 (m, 2H, $CH_2OH$), 4.94 (s, 4H, $CH_2OH$), 5.66 (m, 1H, CHOH), 6.15 (s, 2H, 2vinyl-H), 6.94 (d, 2H, 2Aro-H), 6.97 (d, 2H, J=8.24 Hz, 2Aro-H), 7.52 (t, 2H, J=8.24, 2Aro-H).

Example 4: Aβ Aggregation Inhibition Assay

Experimental design. 3-month old Tg2576 mice were acclimatized for 2 months, and then randomly assigned to different treatment groups. They included the control group (n=10) with vehicle treatment, the cromolyn low dose group and cromolyn high dose group. The treatments were conducted through IP injection with PBS based on 0.1 mL/30 g body weight, 3 times per week for 3 additional months. All mice were sacrificed at 8-month old. Tissues were harvested and processed for postmortem analysis.

Figure 4:
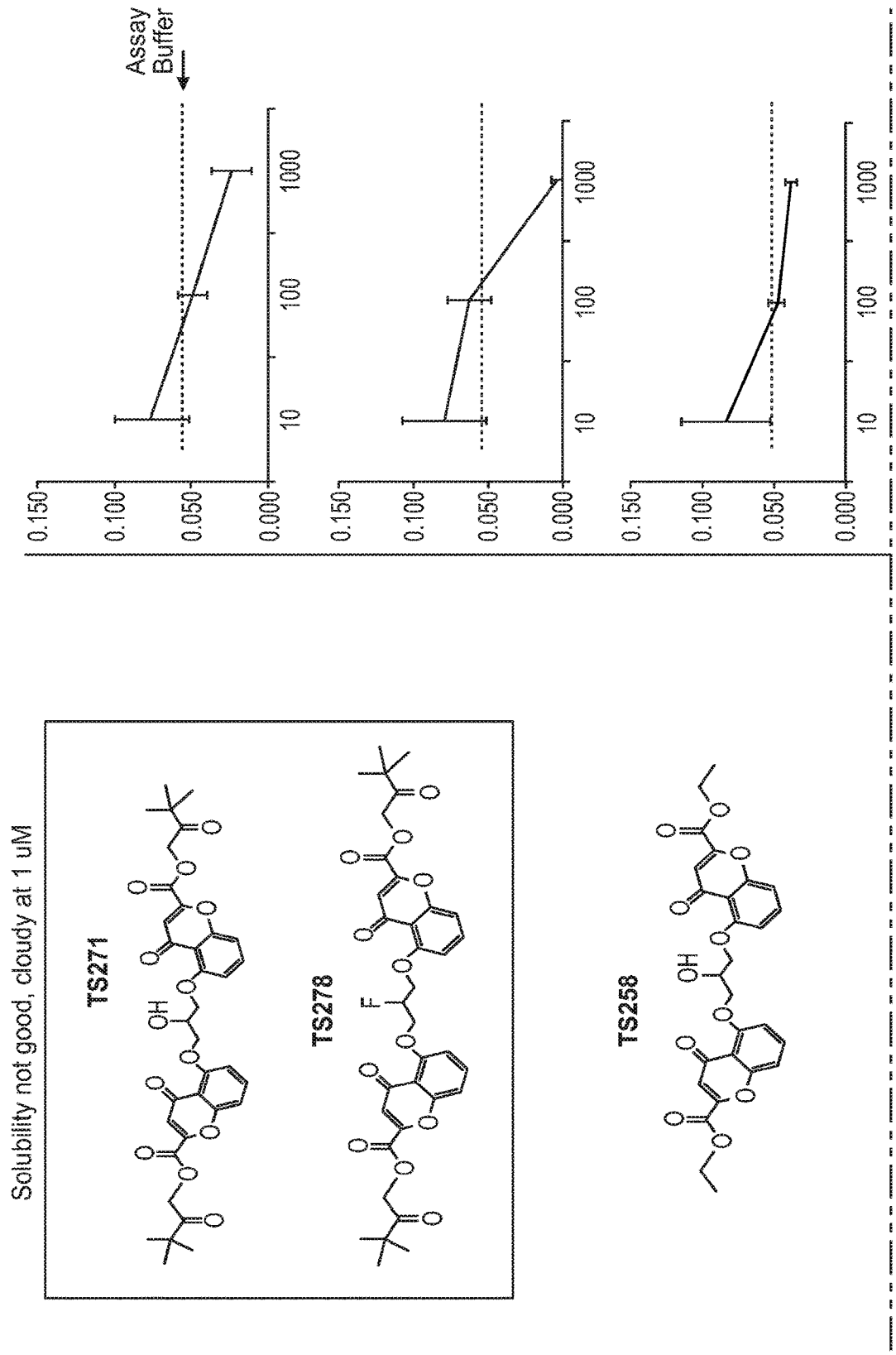
FIG. 4 illustrates the results of an Aβ aggregation inhibition assay using various compounds described herein.
Figure 4:
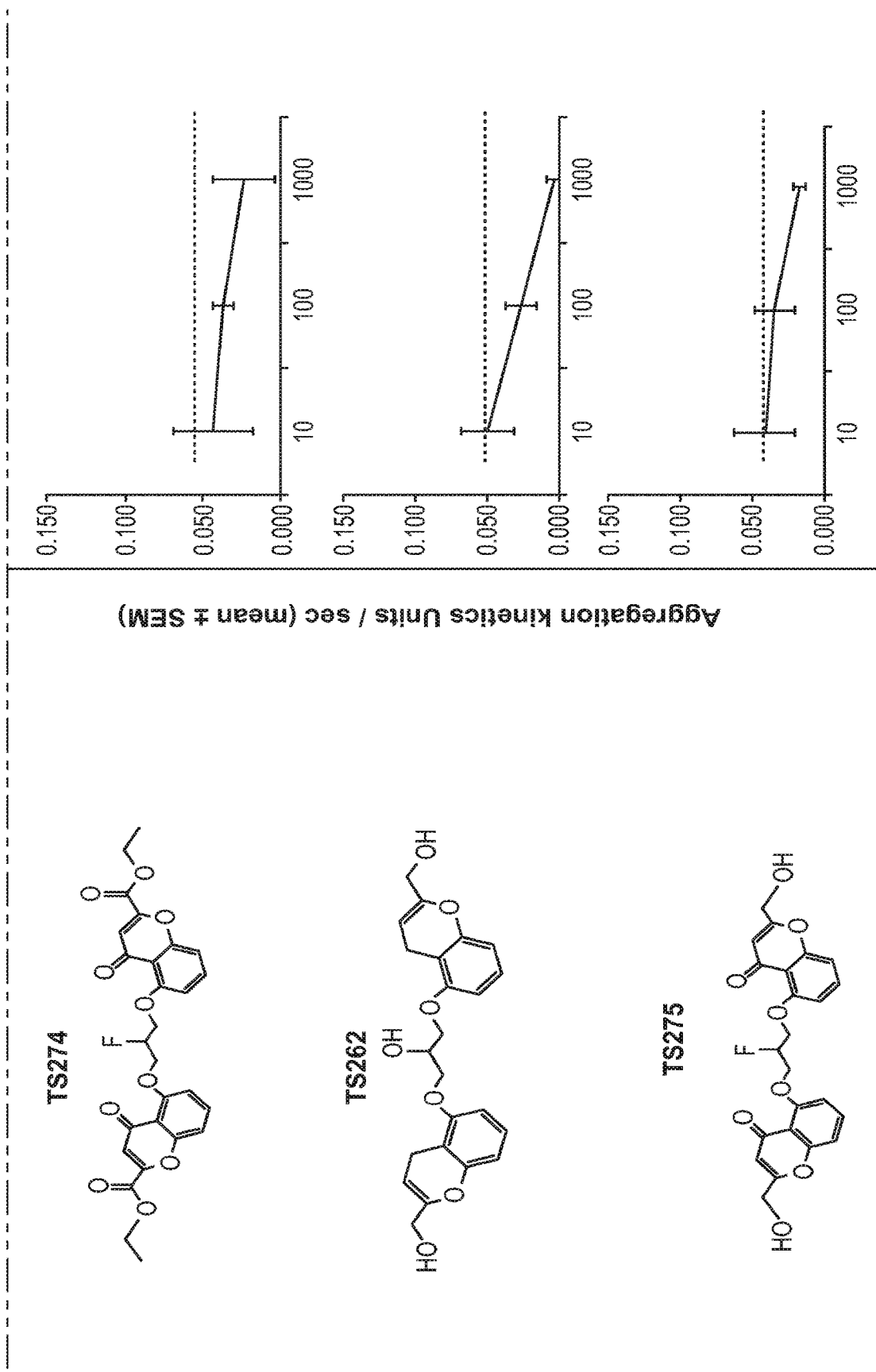
Figure 4:
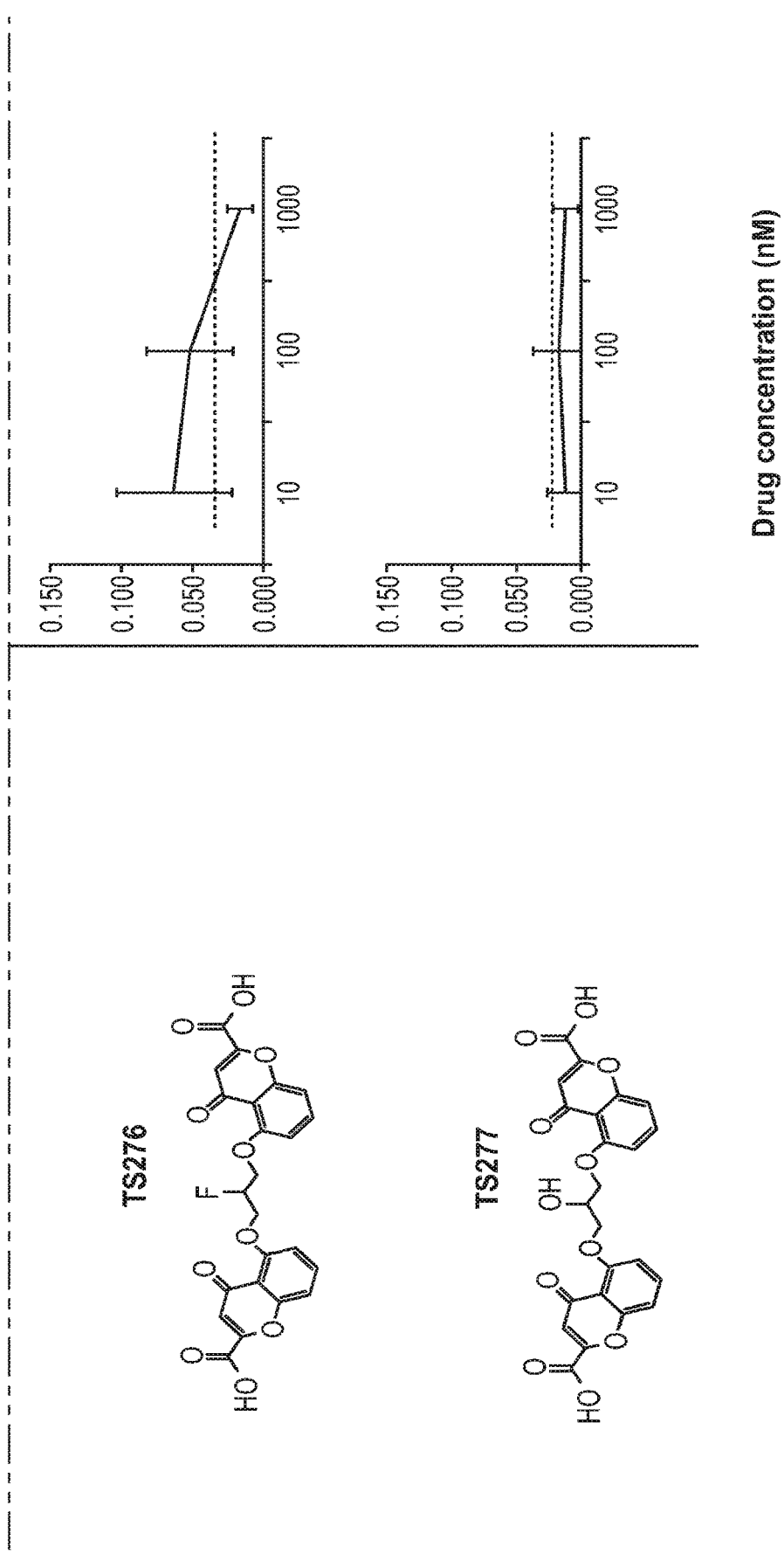

Synthetic $Aβ_{42}$ in final 5 uM was incubated with 10, 100, 1,000 nM of test compounds for 1 hour. The aggregation was initiated with heparin at 0.5 mg/ml in final concentration. The assay buffer consisted of 125 mM NaCl, 2.5 mM KCl, 1 mM $MgCl_2$, 1.25 mM $Na_2H_2PO_4$, 2 mM $CaCl_2$), 25 mM Glucose, and $NaHCO_3$ to adjust pH to 7.4. The assay buffer was used as a control. The aggregation was measured by intensity of Thioflavin T binding, which was detected by fluorescent excitation/emission at 450 nm/480 nm (Spectra Max M3 plate reader, Molecular Devices) in a kinetic mode. Aggregation was recorded as the kinetics was calculated as Vmax by the plate reader's software. The assay was performed in triplicate and expressed as standard mean±SD. Blue dotted line indicate the assay buffer control. FIG. 4 illustrates the results of the assay.

Example 5

Figure 5:
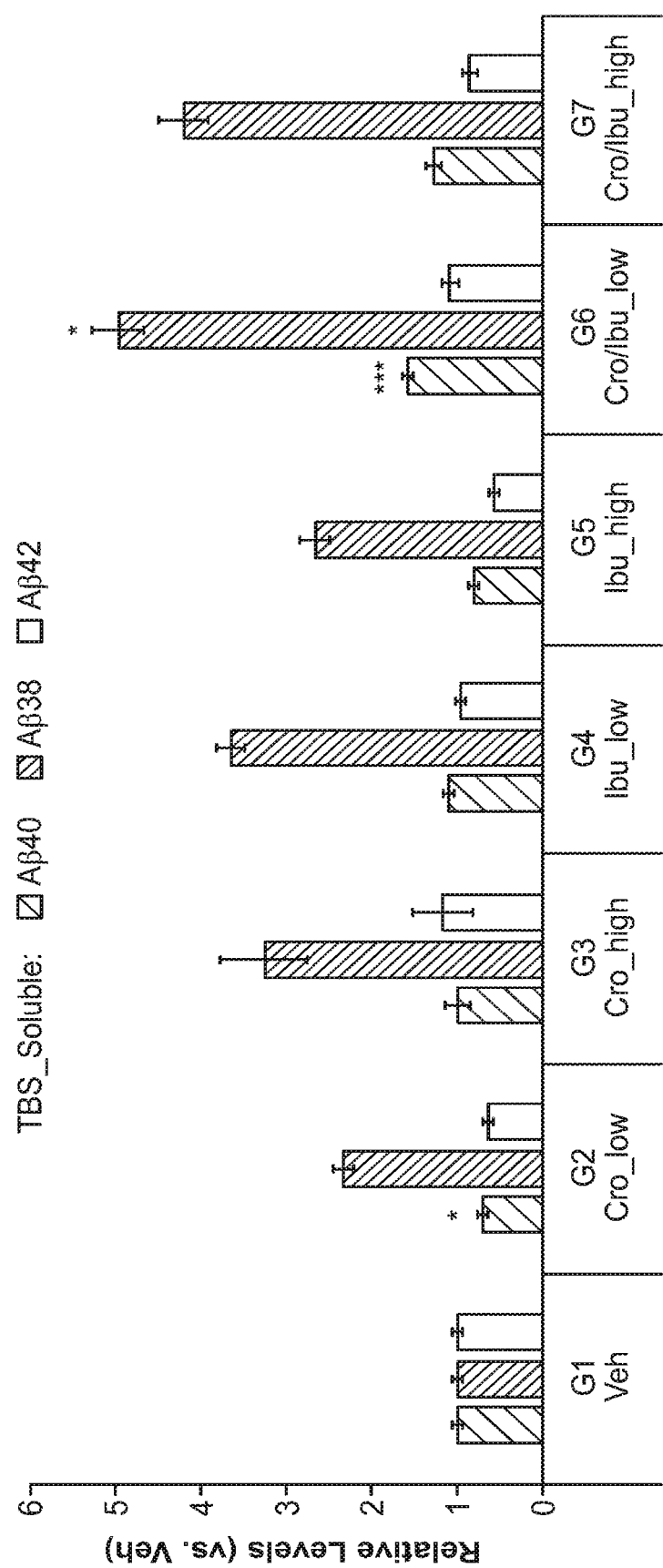
FIG. 5 graphically illustrates that Cromolyn significantly affects the levels of brain TBS soluble Aβ and the ratios of Aβ (42:40).
Figures 6A, 6B, 6C, 6D:
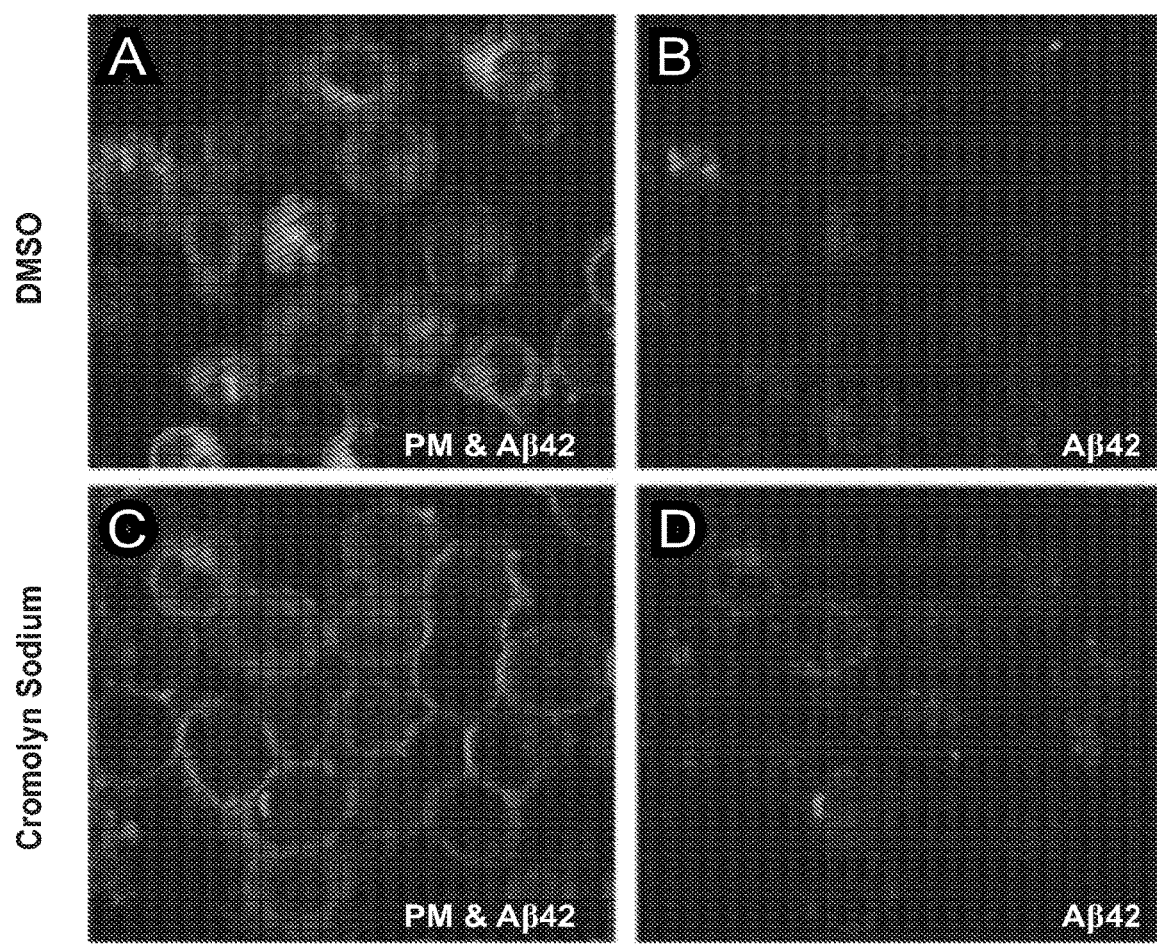
FIG. 6A shows naïve BV2 microglial cells treated with DMSO (control) for 16 h. Afterwards, cells were incubated with fluorescently-labeled Aβ42 and DMSO or cromolyn sodium for 2 hours. After incubation, cells were labeled with a plasma membrane dye (PM) and imaged.
FIG. 6B shows naïve BV2 microglial cells treated with DMSO (control) for 16 h. Afterwards, cells were incubated with fluorescently-labeled Aβ42 and DMSO or cromolyn sodium for 2 hours.
FIG. 6C shows naïve BV2 microglial cells treated with cromolyn sodium (500 μM) for 16 hours. Afterwards, cells were incubated with fluorescently-labeled Aβ42 and DMSO or cromolyn sodium for 2 hours. After incubation, cells were labeled with a plasma membrane dye (PM) and imaged.
FIG. 6D shows naïve BV2 microglial cells treated with cromolyn sodium (500 μM) for 16 hours. Afterwards, cells were incubated with fluorescently-labeled Aβ42 and DMSO or cromolyn sodium for 2 hours.

Cromolyn significantly affected the levels of brain TBS soluble Aβ and the ratios of Aβ (42:40). A-B. MSD (mess scale to measure Aβ 42,40, and 38) Aβ analyses were apply to brain TBS soluble samples. Differences in the Aβ levels and the ratios of Aβ (42:40) comparing the various treatment groups were analyzed. * $p<0.05$; $p<0.01$, *$p<0.001$, one-way ANOVA, Tukey's test; mean f SEM show that cromolyn and ibuprofen combination for the low and high dose higher relative level of Aβ 42/40 and ah higher Aβ 38 that is not implicated in plaque formation. FIG. 5 graphically illustrates the results of a one-way of the differences in the Aβ levels and the ratios of Aβ (42:40).

Example 6—Effect of Cromolyn Sodium on Aβ42 Uptake in Microglial Cells

Confocal microscopy and ELISA assays were used to assess the effect of cromolyn and its derivative compounds on Aβ42 uptake in microglial cells. The BV2 microglial cell line, which was previously found to efficiently take up and degrade exogenously-added Aβ42, was used (Jiang, Q., et al. (2008) Neuron 58, 681-693; Mandrekar et al., 2009 J. Neurosci. 29, 4252-4262). The compounds were tested in naïve BV2 microglial cells to investigate whether they modulate Aβ uptake. The effect of compounds in BV2 cells stably expressing full-length human CD33 (BV2-CD33w) was assessed to explore whether they reverse CD33-mediated inhibition of Aβ uptake (Griciuc et al., 2013 Neuron 78, 631-643).

The compound numbers, molecular weight and concentration of the stock solutions are summarized in Table 1. Cromolyn derivatives, C3 and C4, displayed lower solubility in DMSO in comparison to C1, C2, C5, C6, C7 and C8. Therefore, a 25 mM stock solutions for all the compounds except for C3 and C4 were prepared. The stock solutions for C3 and C4 were prepared at 5 mM and 7.5 mM, respectively. C1 is the parent compound—cromolyn disodium.

TABLE 1

Summary of compounds tested in microglial cells

| Compound Number | Compound Name | Stock Solution (mM) |
|---|---|---|
| C1 | Cromolyn Disodium | 25 |
| C2 | F-Cromolyn Diacid | 25 |
| C3 | ET-Cromolyn | 5 |
| C4 | F-ET-Cromolyn | 7.5 |
| C5 | Triol-Cromolyn | 25 |
| C6 | F-Triol-Cromolyn | 25 |
| C7 | Ac-Triol-Cromolyn | 25 |
| C8 | POM-Cromolyn | 25 |

To investigate the effect of cromolyn sodium on Aβ42 uptake in microglial cells, naïve BV2 cells were treated with DMSO (control) or cromolyn at 500 μM for 16 hours. Afterwards, cells were washed with PBS and treated with DMSO or cromolyn in the presence of the fluorescently-tagged Aβ42 peptide (400 nM, red) for 2 hours. At the end of the treatment, the cells were washed and labeled them with a plasma membrane dye (green).

Using confocal microscopy and the fluorescence signal in the red channel, the levels of intracellular Aβ42 peptide were quantified. All the quantifications were performed by a blind observer with the ImageJ software. Remarkably, cromolyn sodium led to increased uptake of Aβ42 in naïve BV2 microglial cells (FIG. 6A-FIG. 6D).

Furthermore, whether cromolyn sodium modulates Aβ42 uptake in naïve BV2 microglial cells was determined by using the ELISA assay. Additionally, whether cromolyn sodium leads to increased Aβ42 uptake levels in BV2 cells stably expressing full-length human CD33 (BV2-CD33$^{WT}$) was determined. To this purpose, both naïve BV2 and BV2-CD33$^{WT}$ cell lines were treated with DMSO (control) or cromolyn at different concentrations for 16 hours. Then, the cells were washed with PBS and treated with DMSO or cromolyn and soluble untagged Aβ42 peptide (400 nM) for 2 hours. The collected cell lysates were analyzed for Aβ42 uptake levels using the Aβ42-specific ELISA kit from Wako. The ELISA results were normalized to the protein concentration levels that were previously quantified using the BCA assay.

Figure 7A:
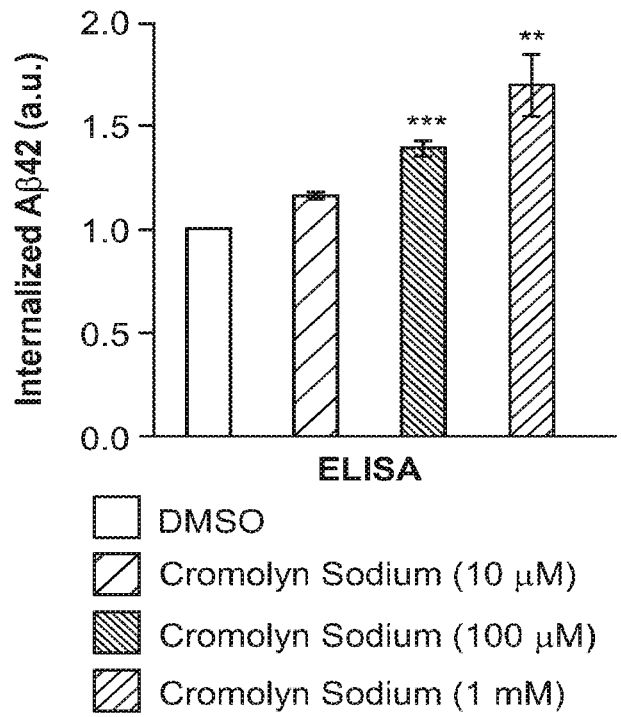
FIG. 7A graphically illustrates that cromolyn sodium promotes microglial Aβ42 uptake. BV2 microglial cells were treated with DMSO or different concentrations of cromolyn sodium for 16 hours. Then, cells were incubated with soluble untagged Aβ42 and DMSO or cromolyn sodium for 2 hours, and collected for ELISA analysis. Both naïve BV2 and BV2-CD33$^{WT}$ microglial cells treated with cromolyn sodium exhibited increased Aβ42 uptake levels in comparison to cells treated with the vehicle (DMSO).
Figure 7B:
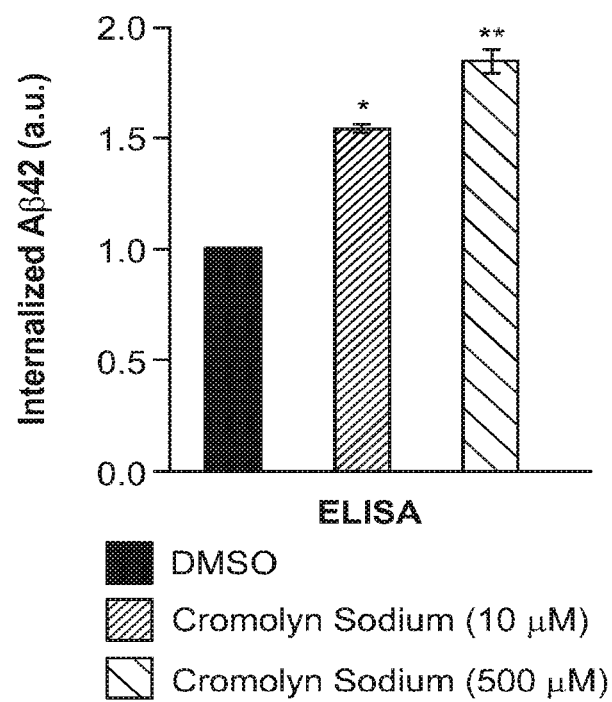
FIG. 7B graphically illustrates that cromolyn sodium promotes microglial Aβ42 uptake. BV2 cells stably expressing CD33 (BV2-CD33$^{WT}$) were treated with DMSO or different concentrations of cromolyn sodium for 16 hours. Then, cells were incubated with soluble untagged Aβ42 and DMSO or cromolyn sodium for 2 hours, and collected for ELISA analysis. Both naïve BV2 and BV2-CD33$^{WT}$ microglial cells treated with cromolyn sodium exhibited increased Aβ42 uptake levels in comparison to cells treated with the vehicle (DMSO).

Cromolyn sodium led to increased Aβ42 uptake at 100 μM and 1 mM in naïve BV2 microglial cells (FIG. 7A) and thus, confirmed the immunofluorescence results by ELISA assay. Cromolyn sodium also led to increased levels of internalized A$42 at 10 μM and 500 μM in BV2-CD33$^{WT}$ cells (FIG. 7B, ELISA assay) and reversed CD33-mediated inhibition of Aβ42 uptake in microglial cells. In conclusion, treatment with cromolyn sodium showed a dose-dependent effect in modulating Aβ42 uptake levels in naïve BV2 and BV2-CD33$^{WT}$ cell lines.

Example 7—Effect of Cromolyn Derivatives on Aβ42 Uptake in Microglial Cells

To investigate the effect of cromolyn derivatives on Aβ42 uptake in microglia, naïve BV2 or BV2-CD33$^{WT}$ cells were plated in proliferating media. On the following day, cells were treated with DMSO (control) or the compounds at different concentrations in proliferating media for 3 hours. C1, C2, C5, C6, C7 and C8 were tested at 10, 50, 100 and 150 μM, while C3 and C4 were assessed at 5, 25, 50 and 75 μM due to solubility limit in DMSO. Afterwards, cells were washed with PBS and treated with DMSO or compounds in the presence of the untagged Aβ42 peptide (400 nM) in DMEM media for 2 hours. Compound toxicity was assessed in the media collected at the end of the treatment with CytoTox-ONE™ lactate dehydrogenase (LDH) assay. The remaining cells in the plate were washed with cold PBS and lysed with RIPA buffer supplemented with protease and phosphatase inhibitors. Protein concentrations in the lysate supernatants were determined using the Pierce™ BCA protein assay kit and 2-3 μg/well of total protein from each lysate was analyzed for Aβ42 uptake using the Aβ42 ELISA kit from Wako. Toxic compound concentrations were excluded from further studies.

Figure 8:
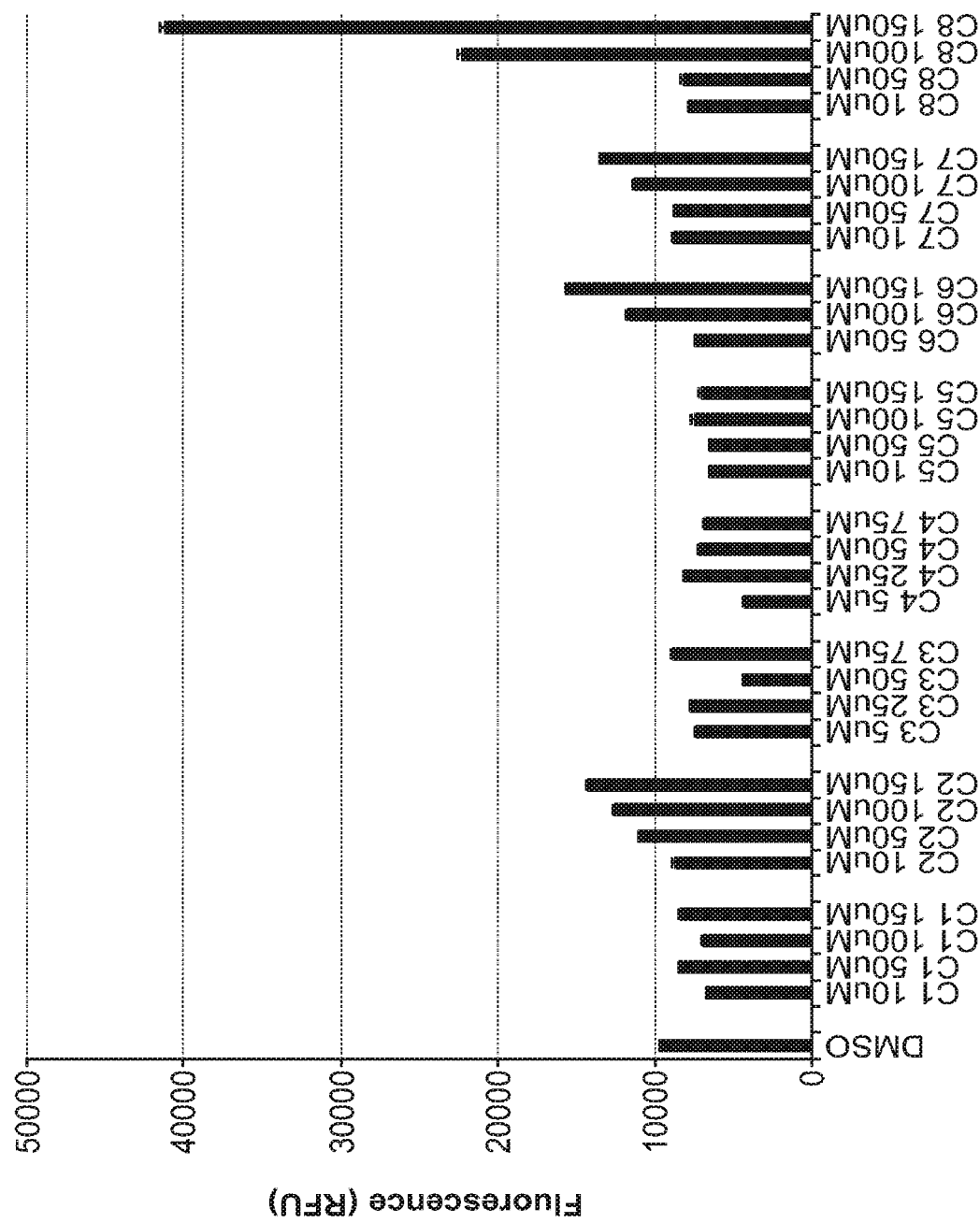
FIG. 8 graphically illustrates that compound C8 displays toxicity when tested at 100 μM or higher concentration in LDH assay. Naïve BV2 microglial cells were treated with DMSO or cromolyn derivatives for 3 hours at different concentrations. C1, C2, C5, C6, C7 and C8 were tested at 10, 50, 100 and 150 μM, while C3 and C4 were assessed at 5, 25, 50 and 75 μM due to solubility limit in DMSO. Afterwards, cells were incubated with soluble untagged Aβ42 peptide and DMSO or cromolyn derivatives for 2 hours. At the end of the treatment, cell media was collected and compound toxicity was assessed with the lactate dehydrogenase (LDH) assay. BV2 microglial cells treated with the cromolyn derivative C8 exhibited increased toxicity at 100 and 150 μM in comparison to cells treated with the vehicle (DMSO).

To investigate whether cromolyn derivatives induce cytotoxicity at higher doses, naïve BV2 microglial cells were incubated with DMSO (vehicle) or cromolyn derivatives at different concentrations for 3 hours. The cells were then washed and incubated with DMSO or compounds and soluble untagged Aβ42 for additional 2 hours. Afterwards, the cell media was collected and measured LDH released by the damaged cells to identify the compounds that induce cytolysis. The LDH assay showed that the cromolyn derivative C8 is the only compound showing toxicity when tested at 100 and 150 μM (FIG. 8). Therefore, 100 and 150 μM concentrations for C8 were excluded from the Aβ42 uptake assays.

Example 8—Modulation of Aβ42 Uptake in Microglial Cells by Cromolyn Derivatives

Figure 9:
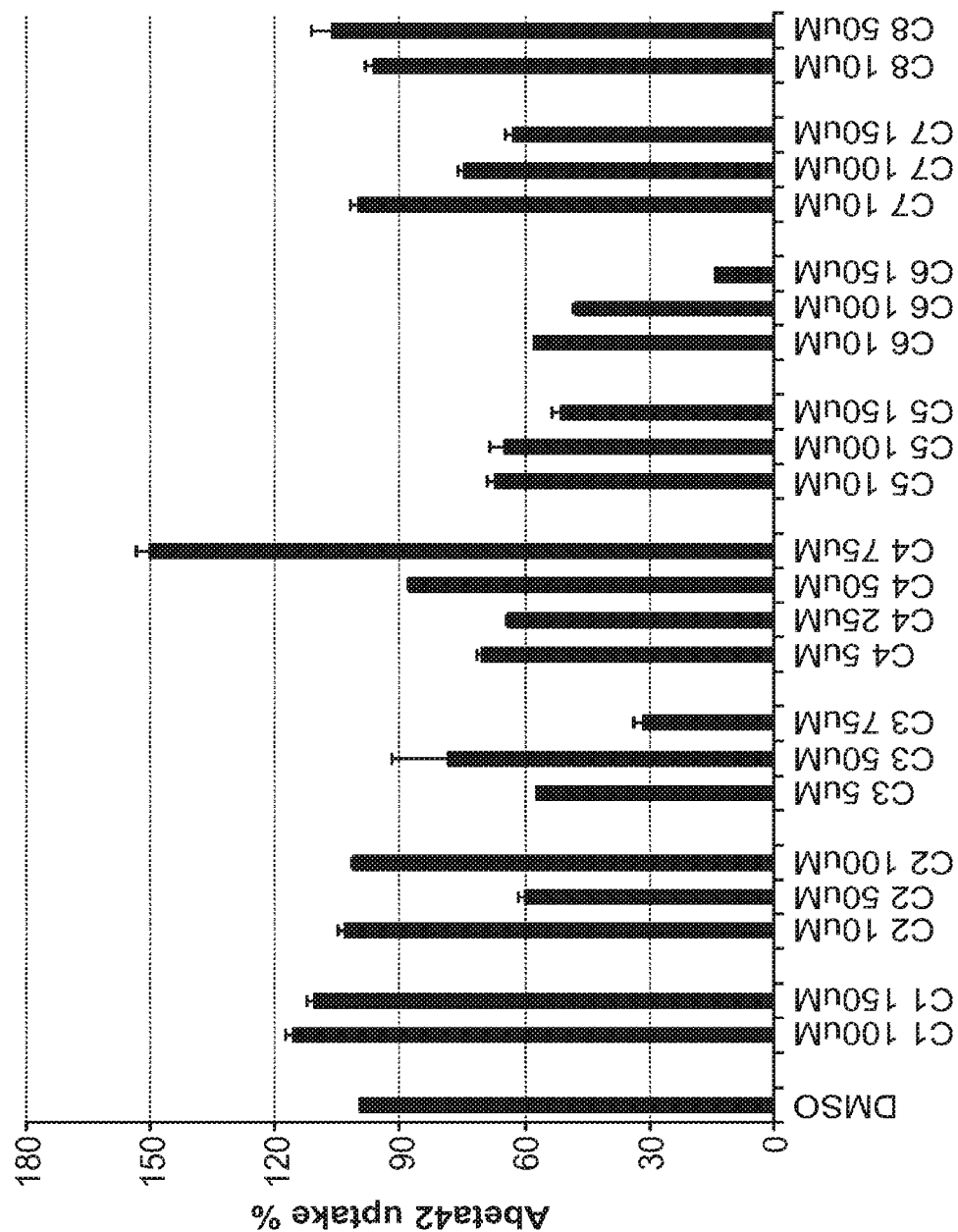
FIG. 9 graphically illustrates that compound C4 promotes Aβ42 uptake in naïve BV2 microglial cells. BV2 cells were treated with DMSO (vehicle) or cromolyn derivatives at different concentrations ranging from 5 to 150 μM for 3 hours. Then, cells were incubated with soluble untagged Aβ42 and DMSO or cromolyn derivatives for additional 2 hours and collected for ELISA analysis. BV2 microglial cells treated with the cromolyn derivative C4 at 75 μM exhibited significantly increased Aβ42 uptake levels in comparison to cells treated with the vehicle.

To test whether cromolyn derivatives modulate Aβ42 uptake, naïve BV2 microglial cells were treated with DMSO (control) or cromolyn derivative compounds at different concentrations for 3 hours. Afterwards, the cells were washed and treated with DMSO or compounds in the presence of untagged Aβ42 peptide for 2 hours. At the end of the treatment, the cell lysates were collected. The analysis for intracellular Aβ42 levels is performed using an Aβ42-specific ELISA kit. The parent compound C1 (cromolyn sodium) led to a modest increase of Aβ42 uptake at 100 and 150 μM in BV2 cells. The C1 aliquot received with the other cromolyn derivatives displayed lower solubility in DMSO than the C1 aliquot that was sent to us the first time (without the cromolyn derivatives). Interestingly, the compound C6 led to a robust inhibition of Aβ42 uptake in BV2 microglial cells. Remarkably, the cromolyn derivative C4 led to an increased uptake of Aβ42 peptide at 75 μM in naïve BV2 microglial cells (FIG. 9).

Further, whether cromolyn derivatives impact Aβ42 uptake and clearance in BV2-CD33$^{WT}$ cells was determined by two independent sets of experiments. BV2-CD33$^{WT}$ cells were treated with DMSO (control) or cromolyn derivatives at different concentrations ranging between 5 and 150 μM.

Figure 10:
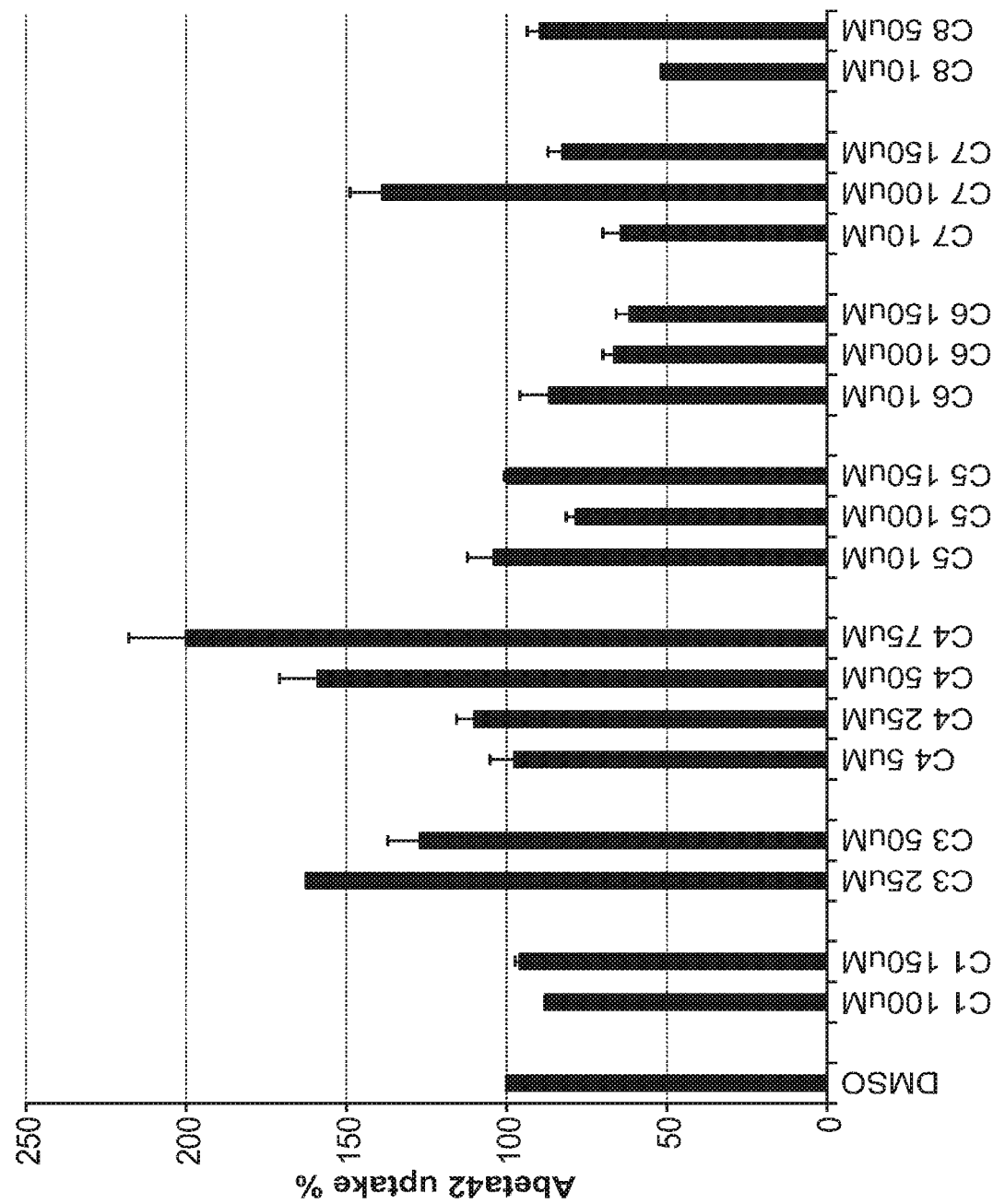
FIG. 10 graphically illustrates that compound C4 promotes Aβ42 uptake in microglial BV2-CD33$^{WT}$ cells. Microglial cells stably expressing CD33w were treated with DMSO as control or cromolyn derivatives (C1, C3-8) at different concentrations for 3 hours.

In the first set of experiments, the cromolyn derivatives C1 and C3-8 were tested. The compound C2 was tested with other cromolyn derivatives in the second set of experiments. Treatment with the compound C4 at 75 μM resulted in a two-fold increase in Aβ42 uptake in comparison to DMSO treatment and displayed a dose-dependent effect at 50 μM (FIG. 10). Using the GraphPad Prism 7 Software, the IC$_{50}$ for C4 was 54.7 μM in BV2-CD33$^{WT}$ cells. The compound C6 exhibits a dose-dependent effect in mediating inhibition of Aβ42 uptake in BV2-CD33$^{WT}$ cells when compared to DMSO treatment.

In the second set of experiments, the cromolyn derivatives C1, C2, and C4-7 in BV2-CD33$^{WT}$ cells was tested. These results confirmed prior results that the compound C4 was the most effective in increasing the Aβ42 uptake at 75 μM and displayed a dose-dependent effect at lower concentrations when compared to DMSO treatment (FIG. 11). Thus, these results suggest that the compound C4 led to increased A$42 uptake levels in BV2-CD33$^{WT}$ cells and reversed the CD33-mediated inhibition of Aβ uptake and clearance (FIGS. 10 and 11).

These results suggest that the cromolyn derivative C4 induced microglial uptake and clearance of Aβ42 and enhanced skewing of microglial cells from the neurotoxic/pro-inflammatory towards neuroprotective/pro-phagocytic activation phenotype.

The invention claimed is:

1. A method of treating a neuron inflammation condition in a patient in need thereof comprising administering to the patient a therapeutically effective amount of the compound having the following formula:

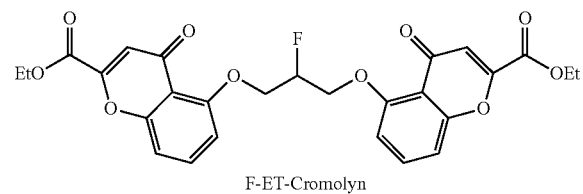 [SMILES: CCOC(=O)c1cc(=O)c2c(OCC(F)COc3cccc4oc(C(=O)OCC)cc(=O)c34)cccc2o1]

F-ET-Cromolyn wherein the neuron inflammation condition is amyotrophic lateral sclerosis (ALS), Huntington's Disease, Parkinson's disease (PD), ischemic stroke, or a condition associated with prion disease.

2. The method of claim 1, wherein the neuron inflammation condition is ALS.

3. The method of claim 1, wherein the neuron inflammation is Huntington's Disease.

4. The method of claim 1, wherein the neuron inflammation is Parkinson's disease.

5. The method of claim 1, wherein the neuron inflammation condition is ischemic stroke.

6. The method of claim 1, wherein the neuron inflammation condition is associated with prion disease.

7. The method of claim 2, wherein the compound is administered intraperitoneally and/or intravenously.

8. The method of claim 1, wherein the compound is administered transdermally.

9. The method of claim 1, wherein the compound is administered by inhalation.

10. The method of claim 1, wherein the compound is administered at a dose between about 1 mg and about 1000 mg per day.

11. The method of claim 1, where in the compound is administered at a dose of about 10, about 20, about 30, about 50, about 100, or about 500 mg per day.

12. The method of claim 2, further comprising co-administering a second compound selected from CD4+; siRNA; miRNA that ameliorates ALS; glial morphology modifier; SOD1 control; and Riluzole.

13. The method of claim 2, further comprising co-administering a second compound selected from an antibody targeting drug that ameliorates ALS and an anti-inflammatory targeting drug that ameliorates ALS.

14. The method of claim 1, further comprising co-administering a second compound selected from a targeting drug that ameliorates neurodegeneration associated with amyloidosis or tauopathies.

15. The method of claim 4, further comprising co-administering a second compound selected from an alpha synuclein targeting drug that ameliorates PD and a Parkinson's targeting drug that ameliorates PD.

16. The method of claim 1, wherein the compound is administered at a dose between about 1 mg and about 70 mg per day.

17. The method of claim 1, wherein the compound is administered orally.

* * * * *